United States Patent
Sugita et al.

[11] Patent Number: 6,143,732
[45] Date of Patent: Nov. 7, 2000

[54] SESQUITERPENE DERIVATIVES

[75] Inventors: Kenichi Sugita, Kyotanabe; Naohiko Hattori, Otsu, both of Japan

[73] Assignee: Shionogi & Co., Ltd., Osaka, Japan

[21] Appl. No.: 09/381,273

[22] PCT Filed: Mar. 11, 1998

[86] PCT No.: PCT/JP98/00992

§ 371 Date: Sep. 20, 1999

§ 102(e) Date: Sep. 20, 1999

[87] PCT Pub. No.: WO98/42714

PCT Pub. Date: Oct. 1, 1998

[30] Foreign Application Priority Data

Mar. 21, 1997 [JP] Japan ..................... 9-067165

[51] Int. Cl.[7] .................. A61K 31/407; C07D 491/052; C07D 491/153
[52] U.S. Cl. .................... 514/63; 514/382; 514/410; 548/251; 548/406; 548/417; 548/418
[58] Field of Search ................ 548/406, 251, 548/417, 418; 514/382, 410, 63

[56] References Cited

FOREIGN PATENT DOCUMENTS

| | | |
|---|---|---|
| 6-239869 | 8/1994 | Japan. |
| 6-256350 | 9/1994 | Japan. |
| 7-145161 | 6/1995 | Japan. |
| 97/11947 | 4/1997 | WIPO. |

*Primary Examiner*—Laura L. Stockton
*Attorney, Agent, or Firm*—Oblon, Spivak, McClelland, Maier & Neustadt, P.C.

[57] ABSTRACT

The Sesquiterpene derivatives are useful as antivirus agents, which are shown by the formula:

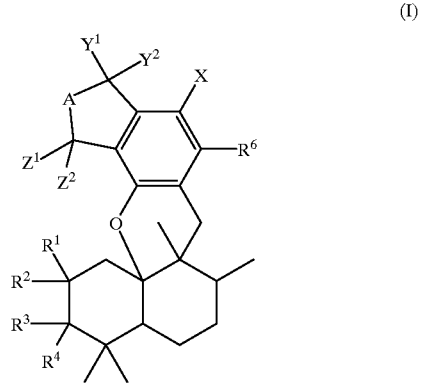

(I)

wherein
$R^1$ is hydrogen or halogen; and $R^2$ is hydrogen, halogen, —$OR^7$ (wherein $R^7$ is hydrogen etc.) or —$NHR^8$ (wherein $R^8$ is hydrogen etc.) etc., or $R^1$ and $R^2$ taken together may form oxo or =$NR^9$ (wherein $R^9$ is hydroxy etc.);
$R^3$ is hydrogen or halogen; $R^4$ is hydrogen, halogen, —$OR^{10}$ (wherein $R^{10}$ is hydrogen etc.), or —$NHR^{11}$ (wherein $R^{11}$ is hydrogen etc.), or $R^3$ and $R^4$ taken together may form oxo or =$NR^{12}$ (wherein $R^{12}$ is hydroxy etc.) or $R^2$ and $R^4$ taken together may form an unsaturated bond or —O—;
A is =$NR^5$ (wherein $R^5$ is hydrogen, lower alkyl etc.)
$R^6$ is hydrogen, cyano etc.,
X is hydrogen, cyano etc.,
$Y^1$ and $Y^2$ are both hydrogens, or taken together may form oxo;
$Z^1$ and $Z^2$ are both hydrogens, or taken together may form oxo, or $Z^1$ is hydrogen and $Z^2$ is hydroxy etc.

10 Claims, No Drawings

SESQUITERPENE DERIVATIVES

This application is a 371 of PCT/JP98/00992 filed Mar. 11, 1998.

TECHNICAL FIELD

The present invention relates to novel compounds having antiviral activities. In more detail, the invention relates to sesquiterpene derivatives having inhibitory activities against influenza A and B, and pharmaceutical compositions containing such derivatives.

BACKGROUND ART

There have been no established method for treating the commonest viral disease, influenza. Human influenza viruses are classified into types A, B and C, depending on their internal antigens, among which types A and B are known to cause intensive symptoms. Amantadine has been known for more than 20 years as a chemotherapeutic agent, though efficacy thereof has not been evaluated yet. Accordingly, there has been a strong demand for the development of novel and effective anti-influenza agents.

It has been known that microorganisms can produce various useful compounds. For example, Stachybotrys, a fungus is known to produce compounds having pyran fused ring [(1) Japanese Patent Publication (KOKAI) 176782/1993; (2) Japanese Patent Publication (KOKAI) 128266/1994; (3) Japanese Patent Publication (KOKAI) 239869/1994; (4) Japanese Patent Publication (KOKAI) 256350 1994; (5) J. Org. Chem. 57 6700–03 (1992)]. These references, however, merely describe that such compounds have nerve growth factor (NGF) activating effects and are useful for the treatment of Alzheimer's diesease (References 1–4) or that such compounds have antibacterial and antifungal effects (Reference 5). Thus, it has not been known that Stachybotrys produces compounds having antiviral activities.

Further, the following references describe compounds having spiro-type fused ring of tetrahydrofuran ring [(6) Japanese Patent Publication (KOKOKU) 11634/1982 (U.S. Pat. No. 4,229,466); (7) Japanese Patent Publication (KOKOKU) 32170/1987 (U.S. Pat. No. 4,831,053); (8) Japanese Patent Publication (KOKAI) 145161/1995; (9) WO 95/26344]. Among these references, References (6), (7) and (9) merely show that their compounds are useful for the treatment of nephritis, hepatitis, and depression/mania, and the like, and Reference (8) merely shows that the compounds have retrovirus protease inhibitory effects.

Further, it is described that terpenehydroquinone derivatives isolated from poriferan have antiviral effects (WO 91/12250), but which does not disclose the compounds of the present invention.

In addition, natural-type sesquiterpene derivatives producible from strains belonging to the Stachybotrys genus and the synthetic derivatives are described in the PCT application (PCT/JP96/02749, filing date: Sep. 25, 1996, applicant: Shionogi), but which does not describe the compounds of the present invention.

Therefore, the development of novel and effective antiviral agents, in particular, those effective against influenza virus has long been demanded.

DISCLOSURE OF THE INVENTION

The present inventors have found that, when cultivated in an appropriate medium, some strains belonging to the Stachybotrys genus produce a substance (SQ-02-S5 et al.) having a strong inhibitory activity against virus. Further at this opportunity, they have synthesized novel sesquiterpene derivatives through the chemical modification of such natural products and found that those derivatives have remarkable activity against virus, in particular, influenza A and B viruses.

Thus, the present invention provides a compound of the formula:

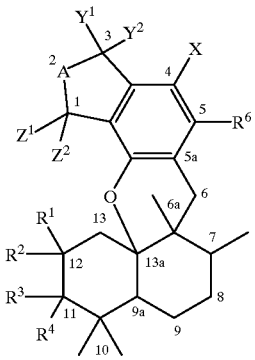

(I)

wherein $R^1$ is hydrogen or halogen; and $R^2$ is hydrogen, halogen, azido, an optionally substituted lower alkyl, an optionally substituted lower alkylcarbonyl, an optionally substituted arylcarbonyl, an optionally substituted heteroarylcarbonyl, —$OR^7$ (wherein $R^7$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfony, —$SO_3H$, an optionally substituted aryl, an optionally substituted aralkyl, an optionally substituted carbamoyl, or —$PO_3H_2$), $S(O)_nR^{13}$ (wherein $R^{13}$ is hydrogen, an optionally substituted lower alkyl, or an optionally substituted aryl, and n is 0, 1, or 2), or —$NHR^8$ (wherein $R^8$ is hydrogen, an optionally substituted lower alkyl, an optionally substituted lower alkylcarbonyl, an optionally substituted lower alkylsulfonyl, an optionally substituted arylcarbonyl, an optionally substituted heteroarylsulfonyl, or an optionally substituted carbamoyl); or $R^1$ and $R^2$ taken togethr may form oxo or =$NR^9$ (wherein $R^9$ is hydroxy, a lower alkoxy, an optionally substituted aralkyl, an optionally substituted arylsulfonylamino, or —$NHCONH_2$);

$R^3$ is hydrogen or halogen; and $R^4$ is hydrogen, halogen, —$OR^{10}$ (wherein $R^{10}$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfonyl, —$SO_3H$, or —$PO_3H_2$), $SR^{14}$ (wherein $R^{14}$ is hydrogen, an optionally substituted lower alkyl, or an optionally substituted aryl), or —$NHR^{11}$ (wherein $R^{11}$ is hydrogen, an optionally substituted lower alkyl, an optionally substituted lower alkylcarbonyl, an optionally substituted lower alkylsulfonyl, an optionally substituted arylsulfonyl, an optionally substituted heteroarylsulfonyl, or an optionally substituted carbamoyl); or $R^3$ and $R^4$ taken together may form oxo or =$NR^{12}$ (wherein $R^{12}$ is hydroxy, cyano, amino, an optionally substituted lower alkoxy, an optionally substituted aralkyl, an optionally substituted arylsulfonylamino, an optionally substituted aliphatic heterocyclic group, or —NHCONH$_2$); or R$^2$ and R$^4$ taken together may form an unsaturated bond or —O—;

a is =NR$^5$ (wherein R$^5$ is hydrogen, lower alkyl, lower alkylcarbonyl, or lower alkylsulfonyl; or R$^5$ and Z$^1$ taken together may form an unsaturated bond);

R$^6$ is hydrogen, cyano, nitro, amino, halogen, an optionally substituted carboxy, or an optionally substituted carbamoyl;

X is hydrogen, cyano, nitro, amino, halogen, hydroxy, lower alkoxy, an optionally substituted carboxy, an optionally substituted carbamoyl;

Y$^1$ and Y$^2$ are both hydrogen, or taken together may form oxo;

Z$^1$ and Z$^2$ are both hydrogens, or taken together may form oxo, or Z$^1$ is hydrogen and Z$^2$ is hydroxy, an optionally substituted lower alkyl, or an optionally substituted lower alkoxy, or an optionally substituted aryl), a pharmaceutically acceptable salt, or a hydrate thereof (those hereinafter referred to as "a compound of the present invention").

The present invention also provides a pharmaceutical composition containing a compound of the present invention, in particular, an antiviral agent.

Preferred embodiments of the present invention are exemplified bellow.

(2) a compound of the present invention, wherein A is =NH; Z$^1$ and Z$^2$ are both hydrogens; Y$^1$ and Y$^2$ taken together form oxo.

(3) a compound of the present invention, wherein R$^1$ is hydrogen; R$^2$ is hydrogen, halogen, amino, azido, or —OR$^7$ (R$^7$ is referred to as the same above); R$^3$ is hydrogen, R$^4$ is —OH.

(4) a compound of the present invention, wherein R$^1$ is hydrogen; R$^2$ is hydrogen, halogen, amino, azido, or —OR$^7$ (R$^7$ is referred to as the same above); R$^3$ and R$^4$ taken together form oxo.

(5) a compound of the present invention, wherein R$^1$ and R$^3$ are both hydrogens; R$^2$ and R$^4$ are both hydrogens or halogens or R$^2$ and R$^4$ taken together form an unsaturated bond or —O—.

(6) a compound of the present invention, wherein X is hydrogen, halogen, cyano, or methoxy.

(7) a compound of the present invention, wherein R$^6$ is hydrogen or cyano.

(8) a compound of the present invention, wherein A is =NH; Y$^1$ and Y$^2$ taken together form oxo; R$^1$, R$^3$, R$^6$, X, Z$^1$ and Z$^2$ are both hydrogens; R$^2$ and R$^4$ taken together form an unsaturated bond.

(9) a compound of the present invention, wherein A is =NH; Y$^1$ and Y$^2$ taken together form oxo; R$^1$, R$^2$, R$^3$, R$^4$, R$^6$, X, Z$^1$ and Z$^2$ are both hydrogens.

(10) a compound of the present invention which has antiviral effects.

(11) a compound of the present invention which is useful as an intermediate for preparing another compound of the present invention having antiviral effects.

(12) a pharmaceutical composition containing a compound of the present invention.

(13) an antiviral agent containing a compound of the present invention.

Terms used herein are explained below.

The term "lower alkyl" refers to a straight or branched alkyl group of 1–8 carbons, and includes, for example, methyl, ethyl, n-propyl, isopropyl, n-butyl, isobutyl, sec-butyl, tert-butyl, n-pentyl, isopentyl, neopentyl, tert-pentyl, hexyl, heptyl, octyl, and the like.

The term "lower alkoxy" refers to a straight or branched alkoxy group of 1–6 carbons, and includes, for example, methoxy, ethoxy, n-propoxy, isopropoxy, n-butoxy, isobutoxy, s-butoxy, n-pentyloxy, isopentyloxy, n-hexyloxy, isohexyloxy, and the like.

The term "aryl" includes for example, phenyl, naphthyl, or polycyclic aromatic hydrocarbon groups (e.g., phenanthryl).

The term "arylcarbonyl" refers to a carbonyl group which is substituted by the above aryl, and is exemplified by benzoyl, naphthylcarbonyl, or the like.

The term "heteroaryl" refers to a 5–6 membered aromatic ring which contains 1–4 heteroatom(s) selected from a group consisting of N, O and S, such as furan, thiophene, pyrrole, oxazole, thiazole, imidazole, pyrazole, triazole, pyridine, pyridazine, pyrimidine, pyrazine, triazine, among which a cyclic group containing N atom(s) such as pyridine or pyrazine is preferred.

The term "aralkyl" refers to a group in which one of the above lower alkyls is substituted by the above aryl, and is exemplified by benzyl, methylbenzyl, or naphthylmethyl.

The term "aralkyloxycarbonyl" refers to a carbonyl group to which the above aralkyl is attached through O atom and is exemplified by benzyloxycarbonyl, or the like.

The term "halogen" may include fluoro, chloro iodo, and bromo.

The terms "lower alkylcarbonyl", "arylcarbonyl" and "heteroarylcarbonyl" refer to carbonyl groups substituted by the above lower alkyl, aryl, or heteroaryl, respectively.

The terms "lower alkylsulfonyl", "arylsulfonyl", and "heteroarylsulfonyl" refer to carbonyl groups substituted by the above lower alkyl, aryl or heteroaryl, respectively.

The term "aliphatic heterocyclic group" refers to a 5–6 membered heterocyclic group containing 1–4 heteroatom(s) selected from a group consisting of N, O and S, and includes, for example, pyrrolidinyl, thiazolidinyl, oxazolidinyl, imidazolidinyl, piperidinyl, piperazinyl, morpholinyl, thiomorpholinyl, pyrrolyl, thiazoryl, and the like.

In the definitions of R$^2$, R$^7$ or R$^{13}$, the substituent(s) on the "optionally substituted lower alkyl", "optionally substituted lower alkylcarbonyl" or "optionally substituted lower alkylsulfonyl" may include a lower alkoxy group as described above, a carboxyl group, a hydroxy group, a halogen atom, an amino group, a substituted amino group (the substituent is e.g., lower alkyl, aryl), a cyano group, a nitro group, a lower alkoxycarbonyl group, a carbamoyl group, an aliphatic heterocyclic group optionally substituted by a lower alkyl (e.g., N-methylpiperidine, N-methylmorpholine, N-methylpiperazine, 1,2-dithiorane), and the like.

Similarly, examples of the substituent(s) on the "optionally substituted aryl", "optionally substituted aralkyl", "optionally substituted arylcarbonyl", "optionally substituted heteroarylcarbonyl", "optionally substituted arylsulfonyl", or "optionally substituted heteroarylsulfonyl" may include a lower alkyl group as described above, a lower alkoxy group as described above, a hydroxy group, a halogen atom, a haloalkyl group, an amino group, a substituted amino group, a cyano group, a nitro group, a carbamoyl group, and the like.

In the definition of R$^8$, the substituent(s) on the "optionally substituted lwoer alkyl", "optionally substituted lower alkylcarbonyl", or "optionally substituted lower alkylsulfonyl" may include a lower alkoxy group as described above, a carboxy group, a hydroxy group, a halogen atom, an amino group, a substituted amino group, a cyano group, a nitro group, a lower alkoxycarbonyl group, a carbamoyl group, an aliphatic heterocyclic group substituted by a lower alkyl (e.g., N-methylpiperidine, N-methylmorpholine, N-methylpiperazine), and the like.

Examples of the substituent(s) on the "optionally substituted arylcarbonyl", "optionally substituted aralkyloxycarbonyl", "optionally substituted arylsulfonyl", or "optionally substituted heteroarylsulfonyl" may include a lower alkyl group as described above, a lower alkoxy group as described above, a hydroxy group, a halogen atom, a haloalkyl group, an amino group, a substituted amino group (the substituent is e.g., lower alkyl, aryl), a cyano group, a nitro group, a carbamoyl group, and the like.

In the definitions of $R^7$ and $R^8$, the substituent(s) on the "optionally substituted carbamoyl" may include a lower alkyl group and an aryl group as described above.

In the definition of $R^9$, the substituent(s) on the "optionally substituted aralkyl" or "optionally substituted arylsulfonylamino" may include a lower alkyl group as described above, a lower alkoxy group as described above, a hydroxy group, a halogen atom, an amino group, a substituted amino group (the substituent is e.g., lower alkyl, aryl), and the like.

In the definition of $R^{10}$ or $R^{14}$, the substituent(s) on the "optionally substituted lower alkyl", "optionally substituted lower alkylcarbonyl", or "optionally substituted lower alkylsulfonyl" may include a lower alkoxy group as described above, a carboxy group, a hydroxy group, a halogen atom, an amino group, a substituted amino group (the substituent is e.g., lower alkyl, aryl), a cyano group, a nitro group, a lower alkoxycarbonyl group, a carbamoyl group, an aliphatic heterocyclic group substituted by a lower alkyl (N-methylpiperidine, N-methylmorpholine, N-methylpiperazine), and the like.

Examples of the substituent(s) on the "optionally substituted aryl", "optionally substituted arylcarbonyl", "optionally substituted heteroarylcarbonyl", "optionally substituted arylsulfonyl" or "optionally substituted heteroarylsulfonyl" may include a lower alkyl group as described above, a lower alkoxy group as described above, a hydroxy group, a halogen atom, a haloalkyl group, an amino group, a substittued amino group (the substituent is e.g., lower alkyl, aryl), a carboxyl group, a lower alkoxycarbonyl group, a lower alkylcarbonyl group, a cyano group, a nitro group, a carbamoyl group, and the like.

In the definition of $R^{11}$, the substituent(s) on the "optionally substituted lower alkyl", "optionally substituted lower alkylcarbonyl", or "optionally substituted lower alkylsulfonyl" may include a lower alkoxy group as described above, a carboxy group, a hydroxy group, a halogen atom, an amino group, a substituted amino ggroup (the substituent is e.g., lower alkyl, aryl), a cyano group, a nitro group, a lower alkoxycarbonyl group, a carbamoyl group, an aliphatic heterocyclic group substituted by a lower alkyl (N-methylpiperidine, N-methylmorpholine, N-methylpiperazine), and the like.

Examples of the substituent(s) on the "optionally substituted arylsulfonyl" or "optionally substituted heteroarylsulfonyl" may include a lower alkyl group as described above, a lower alkoxy group as described above, a hydroxy group, a halogen atom, a haloalkyl group, an amino group, a substituted amino group (the substituent is e.g., lower alkyl, aryl), a cyano group, a nitro group, a carbamoyl group, and the like.

Examples of the substituent(s) on the "optionally substituted carbamoyl" may include a lower alkyl group and an aryl group each as described above, and the like.

In the definition of $R^{12}$, the substituent(s) on the "optionally substituted lower alkoxy", "optionally substituted aralkyl", "optionally substituted arylsulfonylamino", or "optionally substituted aliphatic heterocyclic group" may include a lower alkyl group as described above, a lower alkoxy group as described above, a hydroxy group, a halogen atom, an amino group, a substituted amino group (the substituent is e.g., lower alkyl, aryl), and the like.

In the definition of $R^6$, the substituent(s) on the "optionally substituted carboxy", or "optionally substituted carbamoyl" may include a lower alkyl (e.g., methyl, ethyl, butyl), phenyl, and the like.

In the definition of $Z^2$, the substituent(s) on the "optionally substituted lower alkyl", "optionally substituted lower alkoxy", or "optionally substituted aryl" may include a lower alkyl group as described above, a lower alkoxy group as described above, ahydroxy group, a halogen atom, a haloalkyl group, an amino group, a substituted amino group (the substituent is e.g., lower alkyl, aryl), a cyano group, a nitro group, a carbamoyl group, and the like.

As the salt of a compound of the present invention, any of pharmaceutically acceptable salts can be used, including base addition salts, for example, alkali metal salts such as sodium or potassium salts; alkaline-earth metal salts such as calcium or magnesium salts; ammonium salts; aliphatic amine salts such as trimethylamine, triethylamine dicyclohexylamine, ethanolamine, diethanolamine, triethanolamine, or procaine salts; aralkylamine salts such as N,N-dibenzylethylenediamine salts; heterocyclic aromatic amine salts such as pyridine, picoline, quinoline, or isoquinoline salts; quaternary ammonium salts such as tetramethylammonium, tetraethylammonium, benzyltrimethylammonium, benzyltriethylammonium, benzyltributylammonium, methyltrioctylammonium or tetrabutylammonium salts; and basic amino acids salts such as arginine or lysine salts. Acid addition salts include, for example, mineral acid salts such as hydrochlorides, sulfates, nitrate, phosphates, carbonates, hydrogen carbonates or perchlorates; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

As to the hydrate of a compound of the present invention, the number of water molecules is in the range of 1 to 5 molecules for example, though it may vary depending on the method for synthesis and purification, or the condition of crystallization.

A compound of the present invention include all of the stereoisomers of the compound represented by the general formula (I), among which the representative configuration is shown by the formula:

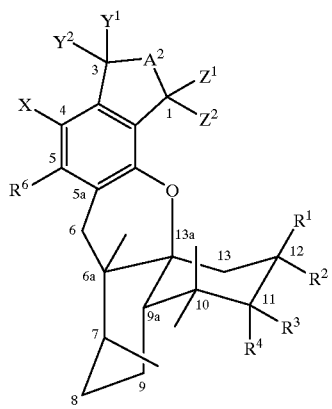

(II)

wherein each definition is the same as defined above. As to the configurations of "$R^1$ and $R^2$" or "$R^3$ and $R^4$" in the compound (II), each may be vice versa.

A compound of the present invention can be prepared by using, as materials, natural products described in PCT application (PCT/JP96/02749) e.g., SQ-02-S3 or SQ-02-S5 described in after-mentioned Reference Example 1), the derivatives thereof, or some known compounds. Further, a compound of the present invention can be derived to some other compounds of the present invention through chemical modification.

Although any fungus strains of Stachybotrys which are capable of producing sesquiterpene derivatives such as SQ-02-S5 can be used for the preparation of SQ-02-S5 et al., a particularly preferred strain is Stachybotrys sp. RF-7260 strain which has been deposited at the National Institute of Bioscience and Human Technology, Ministry of International Trade and Industry (1-1-3 Higashi, Tsukuba shi, Ibaraki) under Accession No. FERM P-14383 on Jun. 24, 1994, and transferred into the International Deposition under Budapest Treaty as FERM BP-5545 on May 20, 1996.

A general method for preparing a compound of the present invention is exampled in more detail below.

(1) Method for preparing natural-type sesquiterpene derivatives represented by SQ-02S5

A fungus strain belonging to the Stachybotrys genus, such as Stachybotrys sp. RF-7260 described above, is cultivated in a solid or liquid medium of suited compositions under appropriate conditions. In principle, the medium can be an usual synthetic or natural medium containing a carbon source, a nitrogen source, inorganic salts, etc. Additional ingredients such as vitamins or precursor substances can also be added, if necessary.

The cultivation can be done at about 15–40° C., preferably at 18–28° C. The pH of the medium can be in the range of 5–9, preferably 6–8. Duration of the cultivation may substantially vary depending on the medium and the cultivation condition, and it takes about 9–14 days. These conditions are, however, adjusted as apprpriate depending on the state of each cultivation, and not limited to those described above. If the cultur foams intensively, an antifoam agent such as vegetable oil, lard or polypropylene glycol can be added as appropriate, before or during the cultivation.

To separate and isolate SQ-02-S5 and the like from the culture after the completion fot the cultivation, usual methods for separation and isolation of fermentation products can be used in combination as appropriate.

(2) Chemical modification of natural-type sesquiterpene derivatives

The natural-type sesquiterpene derivative such as SQ-02-S5 obtained above can be chemically modified according to the method known to a person skill in the art, as shown in the after-mentioned Reference Examples and Examples, such as oxidation, reduction, protection, deprotection, dehydration, epoxidation, phosphorylation, halogenation, O-alkylation, O-acylation, N-alkylation, amination, imination, thiolation, cyanation and the like.

For example, as shown in Examples 1, 2, and 4 etc., SQ-02-S5 is subjected to reduction so as to remove the hydroxy existing at 5-position of the benzene ring contained therein, or a nucleophilic group shown by $R^6$ is introduced into the same position, whereby the following compounds (hereinafter referred to as compound G), an example of a compound of the present invention, can be synthesized,

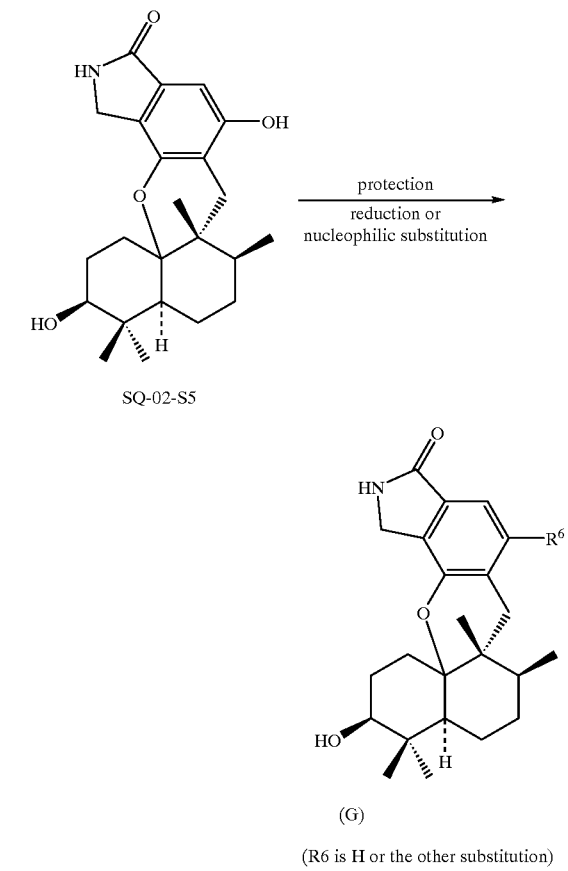

(R6 is H or the other substitution)

The reduction may be carried out with a reduction agent such as $H_2$/PH—C, if necessary under heating, preferably after introducing an appropriate leaving group into the 5-hydroxy position of SQ-02-S5. Examples of the leaving group include, e.g., N-phenyltetrazole, trifluoromethanesulfonyl, and the like. Examples of the reaction solvent include ethanol, methanol, fomic acid, and the like.

The nucleophilic substitution reaction may be carried out by reacing a nucleophilic agent having $R^6$ therein, preferably after transforming the 5-hydroxy to a leaving group such as trifluoromethanesulfonyl. Examples of the reaction solvent include acetonitrile, dimethyl formamide, and the like.

The compound of the present invention wherein $R^3$ and $R^4$ taken together form oxo can be prepared through oxidation of 11-hydroxy of SQ-02-S5 before or after the reduction and/or nucleophilic substitution reaction which are similar to those described above, as shown in the after-mentioned Examples 3 and 5 for example.

In case that any material compound for each reaction described above has any functional group which might bring bad effects into the objective reaction, the group shold be priorly protected if necessary. Examples of the protection group include well known one such as Boc (t-butoxycarbonyl), Ac (acetyl), benzyl, t-butyldimethylsilyl, and the like.

The other compounds of the present invention may be prepared through additional chemical modifications using e.g., compound G described above as materials. Such reactions are exemplified below.

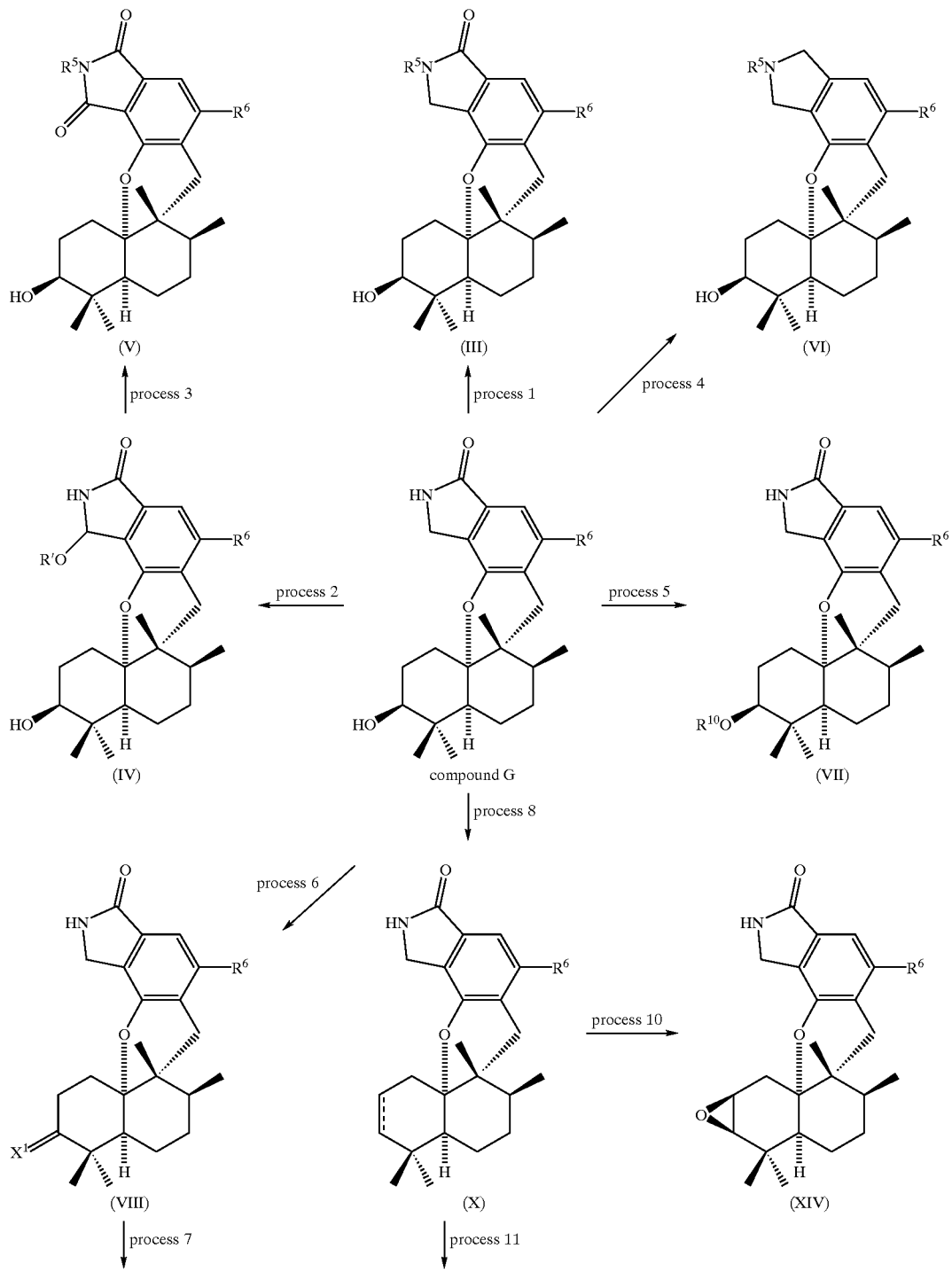

-continued
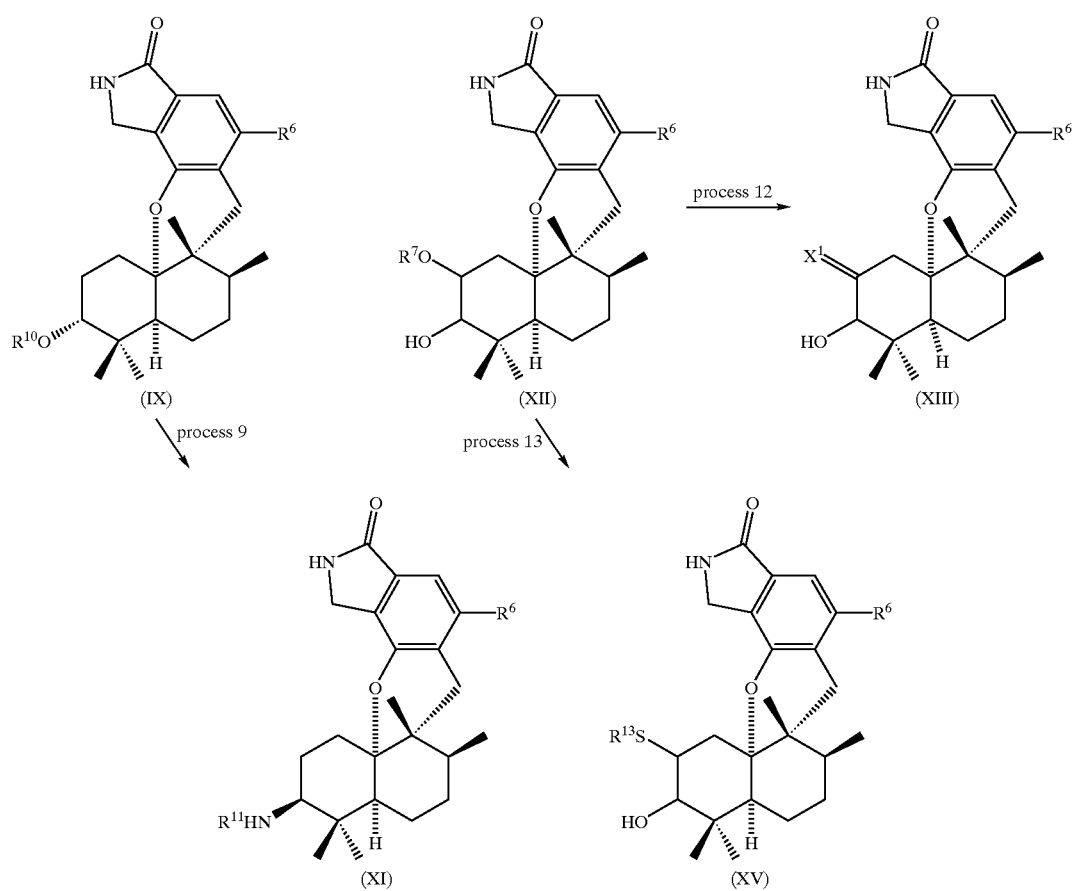

-continued
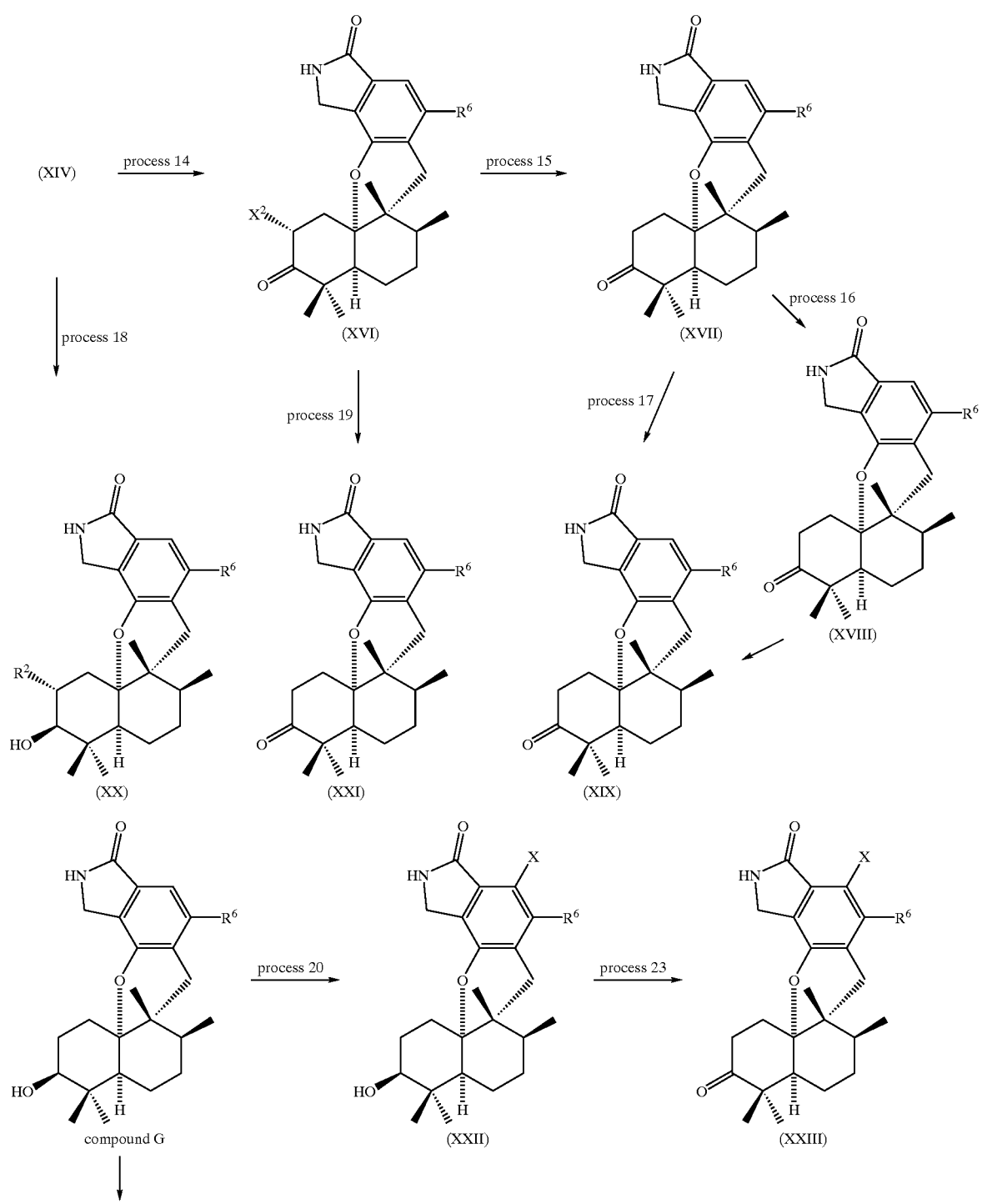

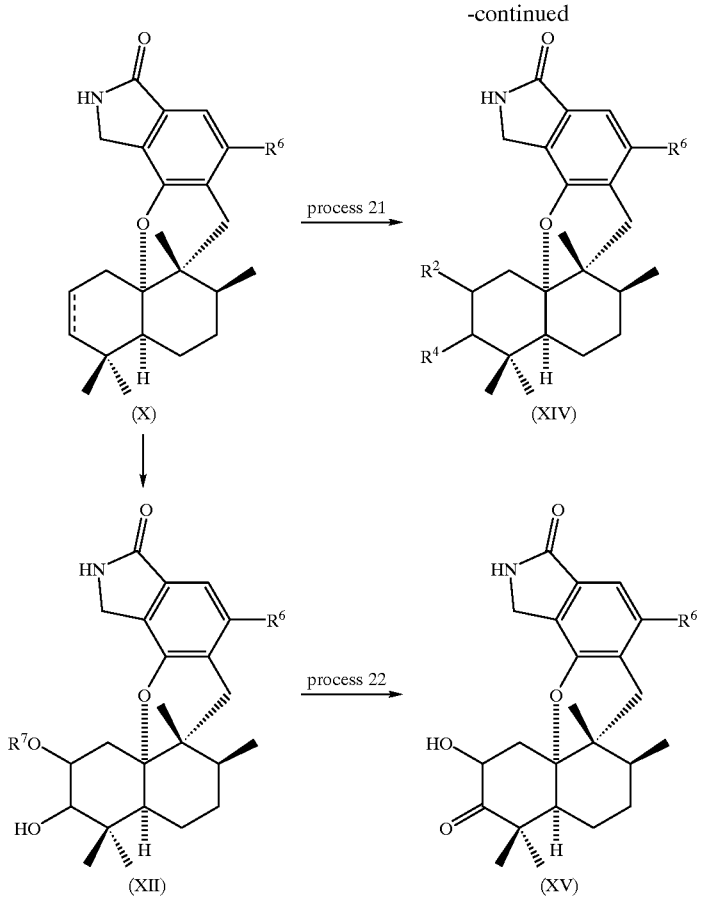

Each process in the above reaction scheme is described below in more detail. In case that any material compound has some group therein which might bring bad effects into a reaction, such a group should be protected by an easily displaceable appropriate protecting group in advance.

Process 1

Compound G is reacted with, for example, an alkyl halide, chloride of lower fatty acid, or sulfonyl chloride compound each of which contains $R^5$ in the presence of a strong base to give Compound (III). This reaction can be achieved in the presence of a base such as sodium hydride, sodium amide, or potassium t-butoxide, under cooling or heating, according to the usual reaction conditions for amide.

Process 2

The active methylene at the 1-position of Compound G is oxidized using, for example, 2,3-dichloro-5,6-dicyanobenzoquinone (DDQ) to give Compound (IV) in which an alkoxy or hydroxy group (OR') has been introduced.

The oxidation reaction is typically achieved using 2- to 10-fold equivalents of the reagent, in an alcoholic solvent such as methanol, ethanol, propanol, at room temperature or an elevated temperature. Preferably, the reaction can be done using 4-fold equivalents of DDQ at 40–50° C. for 20 and several hours. The product of this reaction is a 1-methoxy compound. Although this compound can be directly substituted to give a desired alkoxy derivative, it is preferably converted to its hydroxy form, and then subjected to a substitution reaction with an alcohol. The reaction is achieved by a treatment with an acidic aqueous solution such as diluted hydrochloric or sulfuric acid, in a water-miscible solvent such as dioxane, tetrahydrofuran, acetone or acetonitrile at room temperature.

The substitution reaction of the alkoxy group can be achieved by stirring at room temperature for several tens of minutes in the alcohol solvent corresponding to the desired alkoxy group, in the presence of p-toluenesulfonic acid, benzenesulfonic acid and pyridinium salts thereof.

Process 3

The 1-hydroxy group (OR'=OH) of Compound (IV) is oxidized to the oxo compound, and then any of various substituents is introduced at the 2-nitrogen atom to give a N-alkyl derivative (V).

The oxidation reaction can be achieved in a solvent, for example, acetone, ethyl acetate, acetonitrile, tetrahydrofuran or a halogenated hydrocarbon such as dichloromethane, dichloroethane, chloroform, or carbon tetrachloride, by adding a corresponding amount or excess of active manganese dioxide, and stirring under cooling or at room temperature.

The substitution reaction at the 2-position can be achieved according to the procedure described in Process 1, or more preferably, by a reaction with a desired alkyl halide in the presence of a carbonate such as potassium, sodium or lithium salt, as a base.

Process 4

The 3-carbonyl group of Compound G is reduced, and then any of various substituents is introduced at the 2-imino group to give Compound (VI).

The deoxygenation reaction is achieved using, for example, borane-tetrahydrofuran complex, borane-dimethyl sulfide complex, or the like, in a solvent such as tetrahydrofuran, dioxane, dimethoxyethane, benzene or toluene, with heating at reflux. The reaction time is several hours to several tens of hours.

The substitution reaction of the imino group can be achieved by reacting with, for example, an acid anhydride or chloride of aliphatic lower carboxylic acid, or a sulfonyl chloride, in the presence of a base such as triethylamine, diisopropylethylamine, pyridine or collidine, in an aprotic solvent, for example, dichloromethane, chloroform, diethyl ether, tetrahydrofuran, benzene, toluene, N,N-dimethylformamide or a mixture thereof, with cooling, preferably at a temperature from −20° C. to room temperature.

Process 5

A substituent corresponding to the $R^{10}$ of the general formula (I) is introduced at the 11-hydroxy group of Compound G to give an ester derivative (VII).

The esterification reaction can be achieved by reacting with, for example, an acid anhydride, chloride, or activated ester of sliphatic lower carboxylic acid each corresponding to an aliphatic lower carboxylic acid, an aromatic carboxylic acid, or an aromatic carboxylic acid containing heteroatom (s), according to the conventional methods.

Process 6

The 11-hydroxy group of Compound G is oxidized to give the 11-oxo compound (VIII) ($X^1$=O). It is further subjected to a reaction with any of various substituted amino compounds to give the imino derivative (VIII) ($X^1$=$NR^{12}$).

The oxidation reaction is preferably achieved by Swern oxidation (e.g., oxalyl chloride/dimethyl sulfoxide), $CrO_3$ (chromic acid/pyridine, chromic acid/aqueous acetic acid, pyridinium chlorochromate, pyridinium dichromate, chromic acid/acetone/sulfuric acid (Jones reagent), or the like.

The imination reaction of the 11-oxo compound is achieved by reacting a substituted amino compound ($NH_2R^{12}$) or hydrochloride thereof according to a known method.

Process 7

The 11-oxo compound (VIII) ($X^1$=O) is reduced to its α-hydroxy form, and then a substituent corresponding to the $R^{10}$ of the general formula (I) is introduced to given an ester derivative (IX).

The reduction reaction is achieved using sodium or potassium borohydride, sodium cyanoborohydride, or the like. The reaction is done in a solvent such as methanol, ethanol, tetrahydrofuran, dioxane, dimethoxyethane or a mixture thereof, with cooling or at room temperature.

The esterification can be done similarly to that in Process 5.

Process 8

Compound G is subjected to dehydration reaction, and if desired, further to a hydrogenation reaction, to give Compound (X) (the dotted line represents a presence or absence of a double bond).

The dehydration reaction can be directly achieved in the presence of a base such as pyridine, collidine, lutidine, triethylamine, diisopropylethylamine, using, for example, thionyl chloride, thionyl bromide, oxalyl chloride, methanesulfonyl chloride, or p-toluenesulfonyl chloride, or more preferably, can be achieved by reacting with triphenylphosphine and azodicarboxylic acid diester. The reaction will be typically completed in an aromatic hydrocarbon solvent such as benzene, toluene, or xylene, by heating at a temperature in the range from room temperature to 150° C., preferably at 50–130° C., for several tens of minutes to several hours.

The hydrogenation reaction can be achieved by reducing catalytically in the presence of a catalyst such as palladium-carbon or platinum oxide, in a solvent such as methanol, ethanol, ethyl acetate, dioxane, or tetrahydrofuran.

Process 9

The 11-hydroxy group ($OR^{10}$=OH) of Compound (IX) is converted to an amino group, and then a substituent corresponding to the $R^{11}$ of the general formula (I) is introduced into that amino group to give Compound (XI).

In order to convert the hydroxy group to an amino group, hydrazoic acid is firstly used under conditions for Mitsunobu reaction to give an azide compound. This reaction can be achieved according to the known method. The 11-azido group of the azide compound formed is in the β configuration.

The reduction reaction of the azide group can be achieved by a hydride reduction using a reducing agent such as sodium or lithium borohydride, a reduction through active hydrogen using, for example, magnesium, or calcium in methanol, or a catalytic reduction in the presence of, for example, palladium, platinum, Raney nickel, or Lindlar catalyst, and more preferably, by a reduction using triphenylphosphine. In the latter case, about 1 to 5 fold equivalents of triphenylphosphine and a solvent such as tetrahydrofuran, dioxane, or dimethoxyethane are used. The reaction time will be several hours to several tens of hours at a temperature in the range from 50° C. to 110° C.

The substitution reaction of the amino group can be done as that for the imino group in the Process 4.

Process 10

The double bond between the 11- and 12-position of Compound (X) is oxidized using an appropriate oxidizing agent to give Compound (XIV).

The oxidation reaction can be done according to a conventional method, using an oxidizing agent such as perbenzoic acid, m-chloroperbenzoic acid, or peracetic acid in a solvent such as tetrahydrofuran, dioxane, acetonitrile or a halogenated hydrocarbon such as dichloromethane, dichloroethane, chloroform, or carbon tetrachloride.

Process 11

The double bond of Compound (X) is oxidized to its dihydroxy form (XII) ($R^7$=H), and then a substituent corresponding to the $R^7$ of the general formula (I) is introduced thereto to give an ester derivative (XII, $R^7$=ester residue).

The oxidation reaction is achieved by the osmium tetroxide oxidation, or by using an amine oxide, for example, trimethylamine oxide, or N-methylmorpholine oxide, in the presence of a catalytic amount of osmium tetroxide. As a reaction solvent, halogenated hydrocarbons such as dichloromethane, chloroform, and dichloroethane, ketones such as methyl ethyl ketone, or ethers such as tetrahydrofuran, dioxane, and dimethoxyethane are used alone or in combination. The reaction time varies as needed according to the reaction conditions such as the oxidizing agent used, and is usually several hours to several tens of hours.

The esterification step is done similarly to that in Process 5.

Process 12

In this process, the dihydroxy compound (XII) ($R^7$=H) is oxidized to the 12-oxo compound ($X^1$=O), and further subjected to a reaction with a substituted amino compound to give the imino derivative (XIII) ($X^1\alpha NR^9$).

The oxidation and imination reactions can be done similarly to those in Process 6.

Process 13

The 12-hydroxy group ($OR^7$=OH) of Compound (XII) is substituted with hydrogen sulfide or a thiol corresponding to the $R^{13}$ of the general formula (I) to give a mercapto derivative (XV) ($R^{13}\alpha H$) or a substituted thio derivative (XV).

The substitution reaction with hydrogen sulfide is done using sodium or potassium hydrogensulfide. The reaction is achieved by stirring with cooling or heating in a solvent such as methanol, ethanol, N,N-dimethylformamide, or dimethylsulfoxide. Alternatively, this reaction can be achieved by reacting with potassium thioacetate to give a thioacetate ester which is then hydrolyzed according to a conventional method.

The sub stitution reaction with a thiol can be done by using an alkali metal salt of a desired thiol in place of the above hydrogensulfide salt. The alkali metal salt in this process can be prepared in solution by reacting the thiol compound with a base such as sodium or potassium hydroxide, sodium methoxide or ethoxide, sodium hydride, or potassium t-butoxide.

Process 14

Compound (XIV) is halogenated with a concomitant opening of the epoxy ring, and then the 11-hydroxy group is oxidized to give Compound (XVI) ($X^2$=halogen).

In the halogenation reaction, hydrogen fluoride-pyridine complex, hydrochloric acid-dioxane solution, diethylalminium chloride, bromotrimethylsilane, magnesium bromide-diethyl ether complex, or iodotrimethylsilane, for example, is reacted in a solvent such as tetrahydrofuran, dioxane, dimethoxyethane, acetonitrile, or ethyl acetate, with cooling or at room temperature.

The oxidation reaction can be done similarly to that in Process 6, or more preferably, by the Swern oxidation according to a convention method.

Process 15

The 12-halogen of Compound (XVI) is subjected to a substitution reaction with hydrogen sulfide or a thiol corresponding to the $R^{13}$ of the general formula (I) to give a mercapto derivative (XVII) ($R^{13}$=H) or a substituted thio derivative (XVII).

The substitution reaction with hydrogen sulfide or a thiol is done similarly to those in Process 13.

Process 16

The 12-sulfenyl group of Compound (XVII) is oxidized to give a sulfinyl compound (XVIII).

The oxidation reaction is typically achieved by using an equivalent of an oxidizing agent such as chromic acid, potassium permanganate, perbenzoic acid, m-chloroperbenzoic acid, or Oxone™ in a solvent such as tetrahydrofuran, dioxane, acetronitrile, or a halogenated hydrocarbon such as dichloromethane, dichloroethane, or chloroform, according to a known method.

Process 17

The sulfenyl group on Compound (XVII) or the sulfinyl group of Compound (XVIII) is oxidized using an appropriate oxidizing agent to a sulfonyl compound (XIX)

Although the oxidation reaction can be done by using 30% hydrogen peroxide in a solvent such as acetone, or acetic acid, it can be achieved, more preferably, by using 2- to 5-fold equivalents of oxidizing agent as in Process 16.

Process 18

Concomitantly with opening of the epoxy ring of Compound (XIV), some of various alkyl groups is introduced thereto to give a 12-alkyl derivative (XX). This reaction can be achieved in the presence or absence of copper iodide by using a Grignard reagent or an alkyl lithium with cooling or at room temperature.

Process 19

The 12-halogen of Compound (XVI) is substituted with a functional group corresponding to the $R^2$ of the general formula (I) to give Compound (XXI).

In the substitution reaction, the 2-nitrogen atom may be protected with an appropriate protective group such as 6-butoxycarbonyl, in advance. Next, a strong base such as lithium or sodium amide, sodium hydride, lithium diisopropylamide, lithium or sodium bistrimethylsilylamide can be applied to generate an enolate which is then reacted with, for example, a desired alkyl halide, or a chloride or anhydride of aliphatic lower carboxylic acid, aromatic carboxylic acid, or aromatic carboxylic acid containing heteroatom(s). The reaction will be completed by stirring for several tens of minutes to several hours in a solvent such as tetrahydrofuran, dioxane, dimethoxyethane, dimethylsulfoxide, with cooling or at room temperature.

(Process 20)

The process is halogenation of the 4-position of Compound G. In the reaction, a halogenating agent such as bromine, chlorine, iodine, or N-bromosuccimide may be used, in a solvent (e.g., acetic acid, carbon tetrachloride, chloroform, methylene chloride) if desired, with heating or at room temperature.

(Process 21)

The process is halogenation of the double bonds between the 11- and 12-position of Compound (X). In the reaction, a halogenating agent such as bromine, chlorine, iodine, or N-bromosuccimide may be used, in a solvent (e.g., acetic acid, carbon tetrachloride, chloroform, methylene chloride) if desired, with heating or at room temperature.

(Process 22)

The process is oxidation of the 11-hydroxy group of Compound (XII). The oxidation reaction can be achieved, by protecting the 12-hydroxy group in advance if desired, followed by Swern oxidation (e.g., $(COCl)_2$/dimethyl sulfoxide), $CrO_3$ (chromic acid/pyridine, chromic acid/ aqueous acetic acid, pyridinium chlorochromate, pyridinium dichromate, chromic acid/acetone/sulfuric acid (Jones reagent), or the like.

(Process 23)

The process is oxidation of the 11-hydroxy group of Compound (XXII). The oxidation reaction can be achieved, by protecting the 12-hydroxy group in advance if desired, followed by Swern oxidation (e.g., $(COCl)_2$/dimethyl sulfoxide), $CrO_3$ (chromic acid/pyridine, chromic acid/ aqueous acetic acid, pyridinium chlorochromate, pyridinium dichromate, chromic acid/acetone/sulfuric acid (Jones reagent), or the like.

The method for using a compound of the present invention is explained below.

A compound of the present invention can be administered orally or parenterally. For oral administration, a compound of the present invention can be used in any form of usual formulations, for example, solid formulations such as tablets, powders, granules, capsules; aqueous formulations; oleaginous suspension; solutions such as syrup or elixir. For parenteral administration, a compound of the present invention can be used as an aqueous or oleaginous suspension injection, or nose drops. In the preparation of such formulations, conventional excipients, binding agents, lubricants, aqueous solvents, oleaginous solvents, emulsifying agents, preservatives, stabilizers, and the like can be optionally used.

Although the dosage of a compound of the present invention vary depending on the administration route, age, weight and conditions of the patient, and the disease to be treated, the daily dose for adult can generally be about 0.55 mg–2 g, preferably about 0.1 mg–500 mg, which is administered in one to five divisions, for oral administration. For parenteral administration, the daily does for adult can be about 0.01 mg–1 g, preferably about 0.05 mg–300 mg, which is administered in one to five divisions.

The following examples are provided to further illustrate the present invention and are not to be construed as limiting the scope of the invention.

REFERENCE EXAMPLE 1
(SQ-02-S3 and SQ-02-S5)

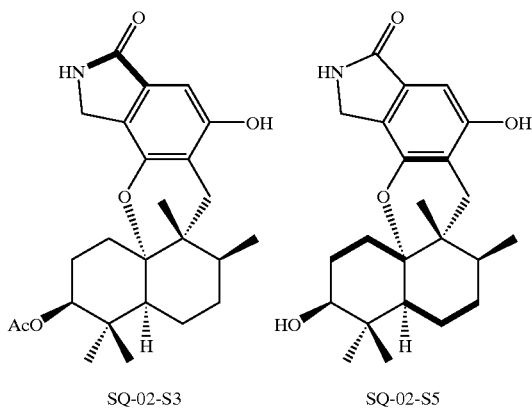

SQ-02-S3        SQ-02-S5

(1) Fermentation Step

Spores of Stachybotrys sp. RF-7260 slant-cultured in 5 test tubes were scraped with a platinum loop, and suspended into 50 ml of physiological saline. Two ml each of this suspension was then inoculated to each of 25 Erlenmeyer flasks (500 ml volume) containing brown rice mediums (25 g of brown rice, 0.5 g of glucose, 0.1 g of yeast extract (Difco), 50 ml of tap water) which have been sterilized at 121° C. for 30 minutes in an autoclave, and statically cultured at 28° C. for 14 days.

(2) Separation Step

The fermented materials in each Erlenmeyer flask from the fermentation step were harvested, which was followed by extraction with 2 L of acetone with stirring. After suction-filtration, the filtrate containing acetone was evaporated under reduced pressure, and the residual aqueous layer was adjusted to pH 4.0 with 1N HCl, followed by extraction with ethyl acetate. The ethyl acetate layer was concentrated to dryness, and partitioned into 0.5 L of 10% water/methanol and 0.5 L of n-hexane. The methanol layer so obtained was concentrated to dryness to give 24 g of crude fraction. This crude faction was recrystallized from toluene-ethyl acetate and ethyl acetate-acetone, sucessively, to give 3.0 g of SQ-02-S3(1) as colorless needle crystals. The recrystallization mother liquid was then concentrated under reduced pressure, and subjected to a silica gel chromatography (Pre-packed column size B (310-25), LiChroprep Si60 (40–63 μm), E. Merck) eluting with a mixed solvent of toluene:ethyl acetate=1:2. The eluent was then concentrated to dryness and recrystallized from ethyl acetate-acetone to give 1.2 g of SQ-02-S3.

The column was then eluted with a mixed solvent of toluene:ethyl acetate=1:4 to give 19 g of a SQ-02-S5 containing fraction. This SQ-02-S5 containing fraction was separated and isolated by a preparative HPLC (LiChroprep RP-18 25–40 μm, 2 cm i.d.×50 cm, acetonitrile:0.1% trifluoroacetic acid-water=50:50) to give a SQ-02-S5 fraction, which was neutralized with 1N NaOH, and evaporated under reduced pressure to remove acetonitrile. The residue was extracted with ethyl acetate. After the evaporation of solvent, SQ-02-S5 was recrystallized from acetone as colorless needle crystals (0.017 g).

SQ-02-S3 (6a, R, 7S, 9a, S, 11 S, 13a S)-11-acetoxy-2, 3,6,6a,7,8,9,9a,10,11,12,13-dodecahydro-5-hydroxy-6a, 7, 10, 10-tetramethyl-3-oxo-1H-benzo[8,8a][1]benzopyrano [2,3-e]isoindole IR $\nu_{max}$ KBr cm$^{-1}$: 3405, 2962, 2875, 1735, 1689, 1627, 1613, 1466, 1369, 1245, 1196, 1167, 1073, 960, 773.

$^1$H NMR (DMSO-d$_6$, 600 MHz) δ: 0.81 (3H, s), 0.84 (3H, s), 1.03 (3H, s), 1.11 (3H, d, J=7.3 Hz), 1.77 (1H, m), 2.05 (3H, s), 2.13 (1H, d, J=17.8 Hz), 3.09 (1H, d, J=17.8 Hz), 4.09 (1H, d-like, J=16.9 Hz), 4.17 (1H, d-like, J=16.9 Hz), 4.65 (1H, t-like), 6.63 (1H, s-like), 8.31 (1H, s-like), 9.73 (1H, s).

SQ-02-S5 (6a R, 7S, 9a S, 11 S, 13a S)-2,3,6,6a,7,8,9,9a, 10,11,12,13-dodecahydro-5, 11-dihydroxy-6a, 7,10,10-tetramethyl-3-oxo-1H-benzo[8,8a][1]benzopyrano[2,3-e] isoindole IR $\nu_{max}$ KBr cm$^{-1}$: 3410, 2960, 2872, 1684, 1625, 1465, 1364, 1168, 1072, 974, 774.

$^1$H NMR (DMSO-d$_6$, 600 MHz) δ: 0.83 (3H, s), 0.89 (3H, s), 0.92 (3H, s), 1.09 (3H, d, J=7.2 Hz), 1.25 (1H, m), 1.46 (1H, dd, J=3.0, 13.0 Hz), 1.54 (1H, m), 1.57 (1H, m), 1.64 (1H, m), 1.73 (1H, m), 1.97 (1H, m), 2.09 (1H, d, J=17.9 Hz), 2.12 (1H, m), 2.21 (1H, m), 2.34 (1H, m), 3.07 (1H, d, J=17.9 Hz), 3.34 (1H, m), 4.06 (1H, d like, J=16.8 Hz), 4.16 (1H, d like, J=16.8 Hz), 4.46 (1H, d, J=3.0 Hz), 6.61 (1H, s), 8.29 (1H, s like), 9.70 (1H, s).

REFERENCE EXAMPLE 2
(SQ-02-S5)

SQ-02-S3 (1.2 g 2.8 mmol) obtained in Reference Example 1 was dissolved in dry methanol (50 ml) and 1M sodium methylate/methanol solution (57 ml), and heated to reflux for 12 hours. To cooled reaction mixture was added water (50 ml), and methanol was evaporated under reduced pressure. To the residual aqueous layer was added 1N HCl to adjust pH to 1.0, followed by extraction with ethyl acetate (500 ml). The ethyl acetate layer was washed with water and dried over anhydrous sodium sulfate. The solvent was then evaporated under reduced pressure. The residue was crystallized from methanol to give SQ-02-S5 (720 mg, 67% yield).

Reaction processes of after-mentioned Reference Examples 3 and 4 are shown below.

23
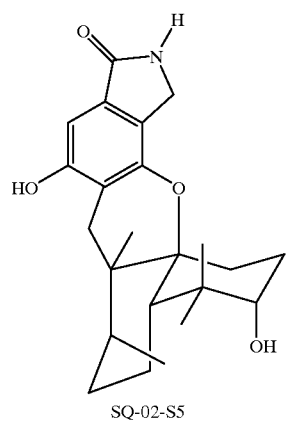 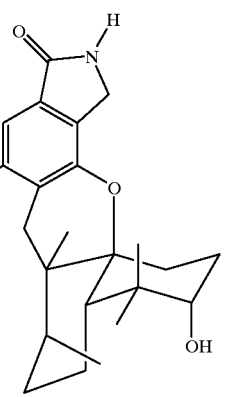 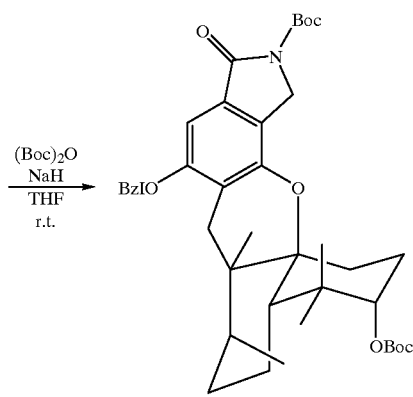
24
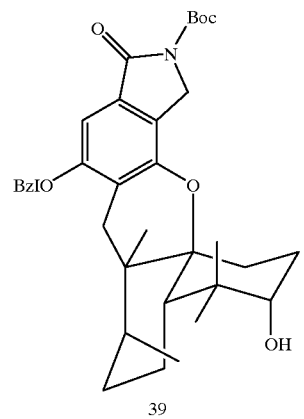
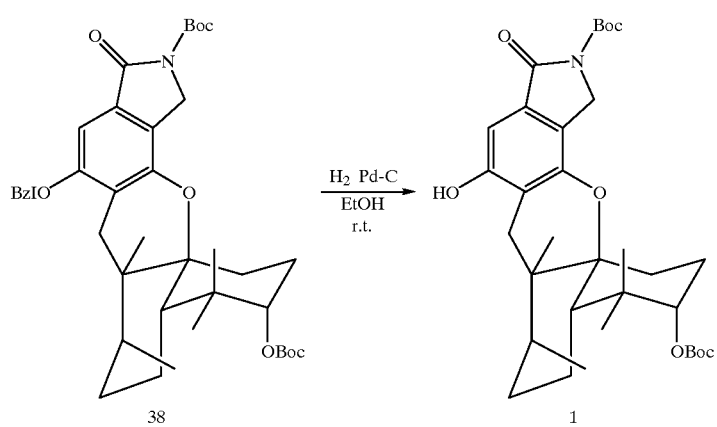
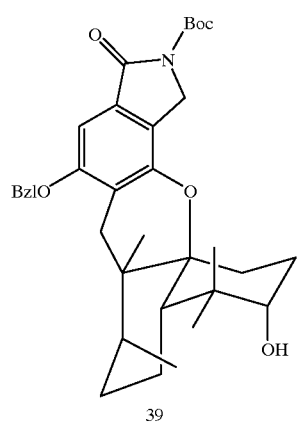 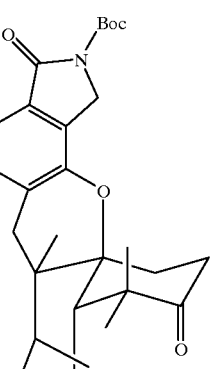 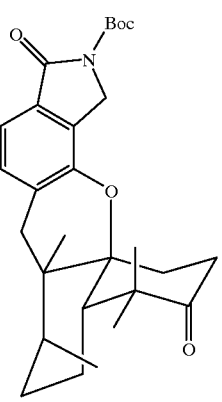

REFERENCE EXAMPLE 3
(compound 1)

(1) To a solution of SQ-02-S5 (20.0 g 51.9 mmol) in acetone (300 ml) were added benzyl bromide (9.6 g, 56.1 mmol) and potassiu carbonate (10.8 g, 78.1 mmol), with stirring under $N_2$ atmosphere at 80° C. for 12 hours. The reaction mixture was filtered with celite, and concentrated under reduced pressure. To the residue, ethyl acetate was added, then the deposited crystals were taken by filtration, dried, to give compound 37 (20.1 g, 81.1%).

(2) To a solution of compound 37 (1.00 g, 2.10 mmol) in dried tetrahydrofran (50 ml), was added sodium hydride (60% oil suspension, 0.20 g, 13.90 mmol) with stirring under $N_2$ atmosphere at room temperature for 30 minutes. To the reaction mixture, were added di-t-butyl dicarbonate (1.0 g, 4.31 mmol), dimethylaminopyridine (0.05 g, 0.41 mmol) with stirring under $N_2$ atmosphere at room temperature for 2 hours. Further, di-t-buryl dicarbonate (0.5 g, 2.15 mmol) was added to the reaction mixture with stirring under $N_2$ atmosphere at room temperature for 4 hours. To the cooled reaction mixture, water was added, then which was extracted with ethyl acetate. The ethyl acetate layer was dried over anhydrous sodium sulfate, and concentrated under reduced pressure. The residue was purified by column chromatography (hexane:ethyl acetate=5:1), to give compound 38 (0.44 g, 31.0%) from the first eluent and compound 39 (0.74 g, 61.2%) from the second.

Compound 38

$^1$H-NMR(CDCl$_3$-TMS) δ ppm: 0.90 (s, 3H), 0.97 (s, 3H), 1.12 (s, 3H), 1.14 (d, 3H, J=7.5 Hz), 1.56 (s, 9H), 1.60 (s, 9H), 2.29 (d, 1H, J=18.3 Hz), 2.51 (m, 1H), 3.18 (d, 1H, J=18.6 Hz), 4.58, 4.64 (d-d, 2H, J=35.1 Hz), 4.70 (s, 1H), 5.10 (s, 2H), 6.98 (s, 1H), 7.43 (m, 5H)

(3) To a solution of compound 38 (0.44 mg, 0.65 mmol) in methanol (50 ml), was added 10% palladium-carbon (0.08 mg) with stirring under $N_2$ atmosphere at room temperature for 3 hours. The reaction mixture was filtered with celite, and concentrated under reduced pressure. The residue was purified by column chromatography (hexane:ethyl acetate= 7.2), to give compound 1 (0.32 mg, 84.0%). $^1$H-NMR (CDCl$_3$-TMS) δ ppm: 0.90 (s, 6H), 1.08 (s, 3H), 1.17 (d, 3H, J=7.8 Hz), 1.60 (s, 9H), 1.61 (s, 9H), 2.22 (d, 1H, J=18.3 Hz), 2.49 (m, 1H), 3.22 (d, 1H, J=18.3 Hz), 4.58, 464 (d-d, 2H, J=30.6 Hz), 4.58 (s, 1H), 5.91 (s, 1H), 6.93 (s, 1H)

REFERENCE EXAMPLE 4
(compound 9)

(1) To a solution of oxalyl chloride (517 mg, 407 mmol) in dried tetrahydrofran (5 ml), were added dimethyl sulfoxide (731 mg, 9.36 mmol) and compound 39 (1.80 g, 3.13 mmol) obtained in Reference Example 3 (2), with stirring under $N_2$ atmosphere at -78° C. for 1 hour. To the reaction mixture, was added triethylamine (2.25 ml) at -78° C., then which was stirred under $N_2$ atmosphere and allowed to elevate to room temperature. To the reaction mixture, was added water, then extracted with ethyl acetate. The ethyl acetate layer was washed with a saturated saline, dried over anhydrous magnesium sulfate, and concentrated under reduced pressure, to give compound 40 (1.75 g, 97.8%).

mp: 188–190

Elementary Analysis ($C_{35}H_{43}NO_6$)

Calcd: C, 73.27; H, 7.56; N, 2.44

Found: C, 73.21; H, 7.56; N, 2.45

$^1$H-NMR(CDCl$_3$-TMS) δ ppm: 0.95 (s, 3H), 0.99 (s, 3H), 1.11 (d, 3H, J=7.5 Hz), 1.25 (s, 3H), 1.60 (s, 9H), 2.35 (d, 1H, J=18.3 Hz), 3.14 (d, 1H, J=18.3 Hz), 4.60 (Abq, 1H, J=16.8 Hz), 4.70 (ABq, 1H, J=16.8 Hz), 5.11 (s, 2H), 7.03 (s, 1H), 7.32–7.48 (m, 5H)

(2) To a solution of compound 40 (3.39 g) in methanol (100 ml), was added 10% palladium-carbon (0.34 g) with stirring under hydrogen atmospher atmosphere at room temperature for 4 hours. The reaction mixture was filtered with celite, and concentrated under reduced pressure. The residue was purified by column chromatography (tetrahydrofran:ethyl acetate=1:1), to give compound 9 (2.74 g, 95.8%).

In addition, the compounds of above Reference Examples 1–4 are those described in PCT application (PCT/JP96/02749) and the derivatives thereof.

Reaction processes of Examples 1 and 2 are shown blow.

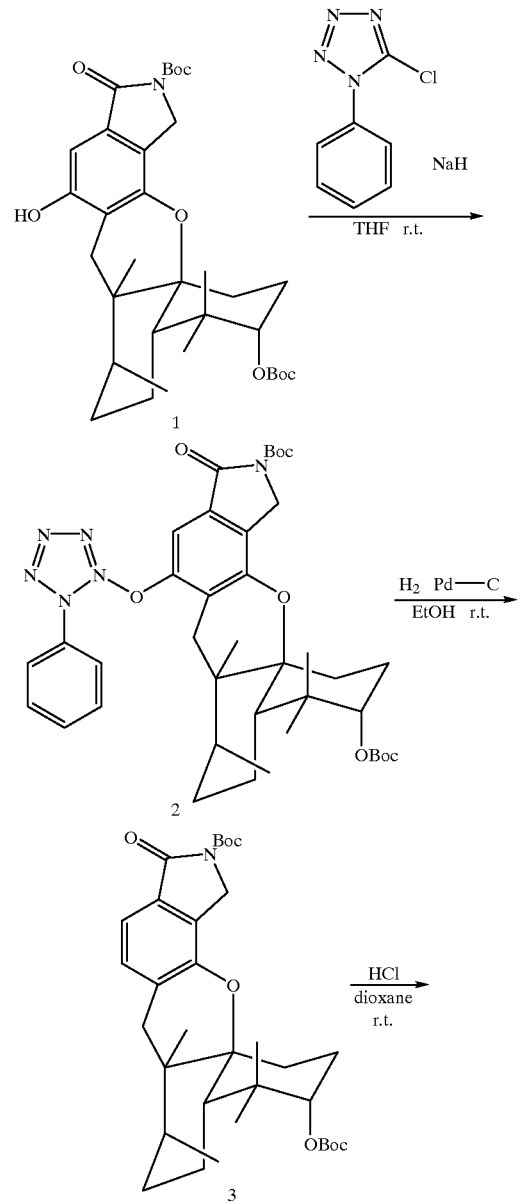

-continued

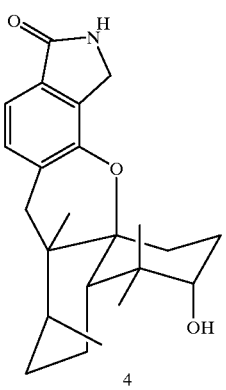

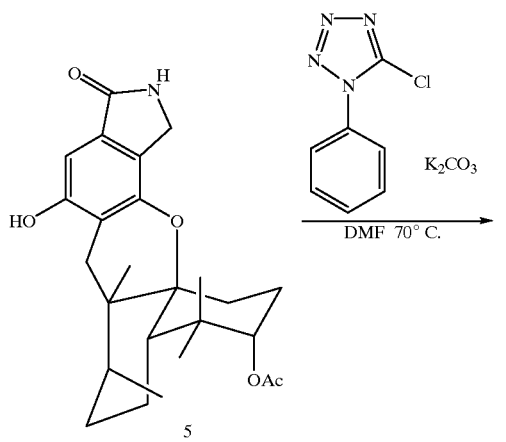

-continued

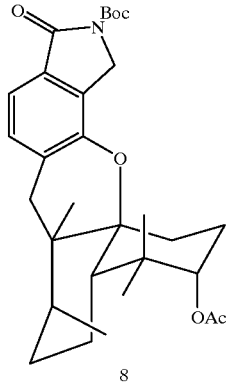

EXAMPLE 1

(compound 4)

(1) To a solution of compound 1 (15.0 mg, 0.025 mmol) in dry tetrahydrofran (2 ml), was added sodium hydride (60%, dispersion in mineral oil), and the mixture was stirred at room temperature under nitrogen atmosphere for 10 minutes. To the reaction mixture was added 5-chloro-1-phenyl-1H-tetrazole (4.6 mg, 0.025 mmol), then which was stirred at room temperature under nitrogen atmosphere for 2 hr. After adding water under ice cooling, the mixture was extracted with ethyl acetate. The extract is dried over sodium sulfate and concentrated under reduced pressure. The residue is purified by column chromatography (hexane:ethyl acetate=4:1), to give compound 2 (14.6 mg). Yield 78.1%

$^1$H-NMR(CDCl$_3$-TMS) δ ppm: 0.92 (s, 3H), 0.94 (s, 3H), 1.13 (s, 3H), 1.15 (d, 3H, J=7.2 Hz), 1.50 (s, 9H), 1.61 (s, 9H), 1.23–2.49 (m, 10H), 2.10 (d, 1H, J=18.7 Hz), 3.32 (d, 1H, J=18.7 Hz), 4.60 (br, 1H), 4.70 (m, 2H), 7.39 (s, 1H), 7.60 (m, 3H), 7.82 (m, 2H)

$^1$H-NMR(CDCl$_3$-TMS) δ ppm: 0.90 (s, 3H), 0.92 (s, 3H), 1.12 (s, 3H), 1.17 (d, 3H, J=7.8 Hz), 1.49 (s, 9H), 1.60 (s, 9H), 1.22–2.52 (m, 10H), 2.12 (d, 1H, J=19.1 Hz), 3.58 (d, 1H, J=19.1 Hz), 4.59 (br, 1H), 4.67 (m, 2H), 7.11 (d, 1H, J=7.8 Hz), 7.35 (s, 1H, J=7.5 Hz)

(2) To a solution of compound 2 (14.0 mg, 0.019 mmol) in ethanol (99.5%, 2 ml), was added 10% palladium carbon (20.0 mg), and the mixture was stirred at room temperature under hydrogen atmosphere for 1 hr. The mixture was filtered over celite and the filtrated was concentrated under reduced pressure. The residue is purified by column chromatography (hexane:ethyl acetate=4:1), to give compound 3 (6.0 mg). Yield: 54.9%

(3) Compound 3 (6.0 mg, 0.011 mmol) was dissolved in 4N dioxane hydrochloride solution (1 ml), and the mixture was stirred at room temperature under nitrogen atmosphere for 1 hr. The mixture was concentrated under reduced pressure, to which carbon tetrachloride was added, then further concentrated to give compound 4 (3.0 mg). Yield: 77.1%

$^1$H-NMR(CDCl$_3$-TMS) δ ppm: 0.92 (s, 3H), 1.00 (s, 3H), 1.05 (s, 3H), 1.15 (d, 3H, J=7.5 Hz), 1.23–2.54 (m, 10H), 2.13 (d, 1H, J=19.1 Hz), 3.61 (d, 1H, J=19.1 Hz), 3.63 (m, 1H), 3.88 (m, 1H), 4.39 (s, 2H), 6.40 (br, 1H), 7.12 (d, 1H, J=7.8 Hz), 7.32 (s, 1H, J=7.5 Hz)

EXAMPLE 2

(compound 4)

(1) To a solution of compound 5 (21.0 g, 49.1 mmol) in dry dimethylformamide (100 ml), were added potassium carbonate (7.4 g, 53.5 mmol) and 5-chloro-1-phenyl-1H-tetrazole (9.8 g, 54.3 mmol), and the mixture was stirred at 70° C. under nitrogen atmosphere for 12 hr. After adding water to the reaction mixture under ice cooling, the separating crystal was collected by filtration, dried, to give compound 6 (28.0 g). Yield: 99.6%

$^1$H-NMR(CDCl$_3$-TMS) δ ppm: 0.90 (s, 3H), 0.94 (s, 3H), 1.13 (d, 3H, J=7.8 Hz), 1.14 (s, 3H), 1.30–2.20 (m, 9H), 2.10 (s, 3H), 2.15 (d, 1H, J=18.3 Hz), 2.40 (m, 1H), 3.34 (d, 1H, J=18.3 Hz), 4.40 (s, 2H), 4.79 (br, 1H), 6.20 (br, 1H), 7.36 (s, 1H), 7.60 (m, 3H), 7.82 (m, 2H)

(2) To a solution of compound 6 (28.0 g, 49.0 mmol) in dry tetrahydrofran (250 ml), was added sodium hydride (60%, dispersion in mineral oil) (2.14 g, 53.5 mmol), and the mixture was stirred at room temperature under nitrogen atmosphere for 30 minutes. After adding di-t-buryl dicarbonate (11.8 g, 50.9 mmol) to the reaction mixture, the solution was stirred at room temperature for 5 hr. After adding water under ice cooling, the mixture was extracted with ethyl acetate. The extract is dried over sodium sulfate and concnetrated under reduced pressure. The residue is purified by column chromatography (hexane:ethyl acetate= 2:1), to give compound 7 (23.0 g). Yield: 69.9%

$^1$H-NMR(CDCl$_3$-TMS) δ ppm: 0.89 (s, 3H), 0.90 (s, 3H), 1.12 (s, 3H), 1.17 (d, 3H, J=7.8 Hz), 1.60 (s, 9H), 1.22–2.52 (m, 10H), 2.10 (s, 3H), 2.12 (d, 1H, J=17.4 Hz), 3.35 (d, 1H, J=17.4 Hz), 4.69 (d, 2H, J=6.47 Hz), 4.80 (br, 1H), 7.39 (s, 1H), 7.60 (m, 3H), 7.80 (m, 2H)

(3) To a solution of compound 7 (23.0 g, 34.2 mmol) in ethanol (99.5%, 300 ml), was added 10% palladium carbon (4.6 g), and the mixture was stirred at 70° C. under hydrogen atmosphere for 2 hr. The mixture was filtered over celite, and the filtrate was concentrated under reduced pressure. The residue is purified by column chromatography (hexane:ethyl acetate=5:2), to give compound 8 (14.2 g). Yield: 81.1%

$^1$H-NMR(CDCl$_3$-TMS) δ ppm: 0.89 (s, 3H), 0.91 (s, 3H), 1.14 (s, 3H), 1.16 (d, 3H, J=7.8 Hz), 1.60 (s, 9H), 1.40–2.52 (m, 10H), 2.10 (s, 3H), 2.12 (d, 1H, J=17.6 Hz), 3.58 (d, 1H, J=17.6 Hz), 4.67 (d, 2H, J=5.40 Hz), 4.81 (br, 1H), 7.12 (d, 1H, J=7.8 Hz), 7.36 (d, 1H, J=7.8 Hz)

(4) To a solution of compound 8 (13.0 g: 25.4 mmol) in ethanol (80 ml), were aded water (20 ml) and 4N aqueous lithium hydroxide (15 ml), and the mixture was stirred at 90° C. under hydrogen atmosphere for 3 hr. The mixture was concentrated under reduced pressure, to which water was added. The separating crystal was collected by ciltration and dried, to give compound 4 (9.0 g). Yield: 95.8%

$^1$H-NMR(CDCl$_3$-TMS) δ ppm: 0.92 (s, 3H), 1.00 (s, 3H), 1.05 (s, 3H), 1.15 (d, 3H, J=7.5 Hz), 1.23–2.54 (m, 10H), 2.13 (d, 1H, J=19.1 Hz), 3.61 (d, 1H, J=19.1 Hz), 3.63 (m, 1H), 3.88 (m, 1H), 4.39 (s, 2H), 6.40 (br, 1H), 7.12 (d, 1H, J=7.8 Hz), 7.32 (s, 1H, J=7.5 Hz)

EXAMPLE 3

(compound 12)

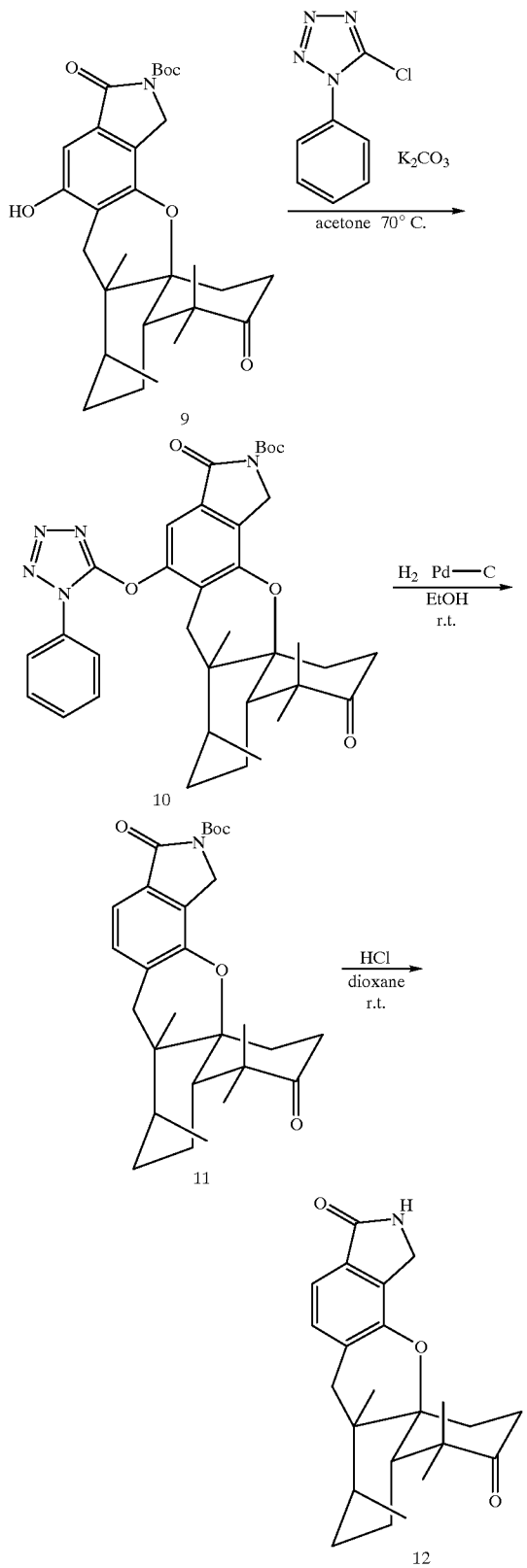

(1) To a solution of compound 9 obtained in Reference Example 4 (1.00 g, 2.10 mmol) in acetone (20 ml), were added potassium carbonate (0.33 g, 2.37 mmol), and 5-chloro-1-phenyl-1H-tetrazole (0.41 g, 2.27 mmol), and the mixture was stirred at 70° C. under nitrogen atmosphere for 12 hr. The mixture was filtrated over celite, and the filtrate was concentrated under reduced pressure. To the residue was added diisopropylether, then the separating crystal was collected by filtration and dried, togive compound 10 (1.05 g). Yield: 80.8%

(2) To a solution of compound 10 (1.05 g, 1.70 mmol) in 99.5% ethanol (60 ml), was added 10% palladium carbon (0.25 g), and the mixture was stirred under hydrogen atmosphere for 2 hr. The mixture was filtrated over celite, and the filtrate was concentrated under reduced pressure. The residue is purified by column chromatography (hexane:ethyl acetate=2:1), to give compound 11 (0.57 g). Yield: 72.5%

(3) Compound 11 (150 mg, 0.32 mmol) was dissolved in 4N dioxane hydrochloride solution (2 ml), with stirring at room temperature under nitrogen atmosphere for 1 hr. The mixture was concentrated under reduced pressure, to which diisopropylether was added, then the separating crystal was collected by filtration and dried, to give compound 12 (88 mg). Yield: 78.6%

$^1$H-NMR(CDCl$_3$-TMS) δ ppm: 0.98 (s, 3H), 1.01 (s, 3H), 1.13 (d, 3H, J=7.8 Hz), 1.19 (s, 3H), 1.25–2.58 (m, 10H), 3.02 (m, 1H), 3.50 (d, 1H, J=18.2 Hz), 4.00 (s, 2H), 6.00 (br, 1H), 7.15 (m, 1H), 7.39 (m, 1H)

elementary Analysis (C$_{23}$H$_{29}$NO$_3$, 0.4 H$_2$O)

Calcd: C, 73.73; H, 8.02; N, 3.74

Found: C, 73.73; H, 8.04; N, 3.62

EXAMPLE 4

(compound 15)

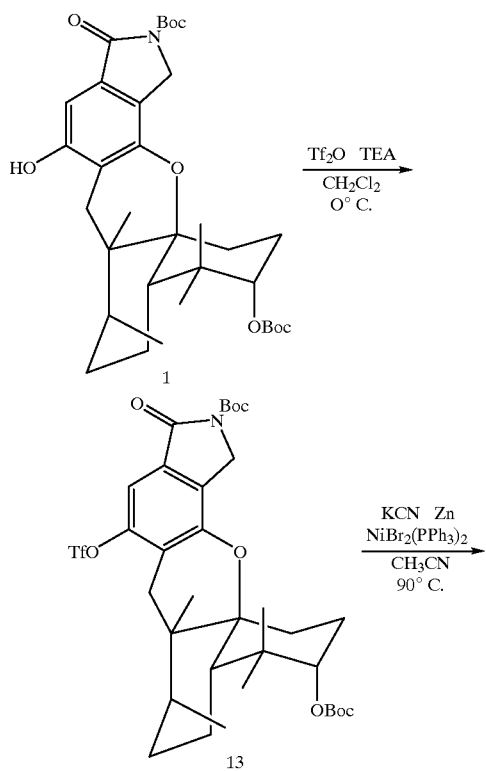

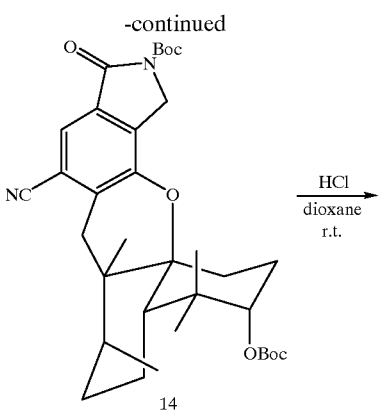

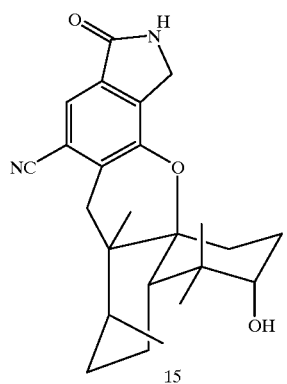

(1) To a solution of compound 1 in Reference Example 3 (100 mg, 0.17 mmol) in dry methylene chloride (2 ml), was added triethylamine (21 mg, 0.20 mmol) inder ice cooling, and the mixture was stirred at the same temperature under nitrogen atmosphere for 10 minutes. To the mixture was added anhydrous trifluoromethane sulfonate (58 mg, 0.20 mmol) under ice cooling, and the mixture was stirred under nitrogen atmosphere for 1 hr. The reaction mixture was concentrated under reduced pressure, the residue was purified by column chromatography (hexane:ethyl acetate=4:1), to give compound 13 (120 mg). Yield: 98.0%

$^1$H-NMR(CDCl$_3$-TMS) δ ppm: 0.90 (s, 3H), 1.09 (s, 3H), 1.19 (d, 3H, J=7.2 Hz), 1.49 (s, 9H), 1.60 (s, 9H), 1.40–2.47 (m, 10H), 2.30 (d, 1H, J=18.0 Hz), 3.42 (d, 1H, J=18.0 Hz), 4.60 (br, 1H), 4.70 (m, 2H), 7.33 (s, 1H)

(2) To a solution of compound 13 (123 mg, 0.17 mmol) in dry acetonitrile (0.5 ml), were added potassium cyanide (22 mg, 0.34 mmol), dibromo bistriphenylphosine nickel (5 mg, 0.006 mmol), zinc power (1 mg, 0.01 mmol), and the mixture was concentrated under reduced pressure, and the residue was purified by column chromatography (toluene:ethyl acetate=9:1), to give compound 14 (63 mg). Yield: 61.8%

$^1$H-NMR(CDCl$_3$-TMS) δ ppm: 0.91 (s, 3H), 0.93 (s, 3H), 1.08 (s, 3H), 1.19 (d, 3H, J=7.2 Hz), 1.50 (s, 9H), 1.61 (s, 9H), 1.40–2.50 (m, 10H), 2.43 (d, 1H, J=18.8 Hz), 3.60 (d, 1H, J=18.0 Hz), 4.60 (br, 1H), 4.70 (m, 2H), 7.70 (s, 1H)

(3) To a solution of compound 14 (63 mg, 0.11 mmol) in 4N dioxane hydrochloride solution (2 ml), and the mixture was stirred at room temperature under nitrogen atmosphere for 1 hr. The mixture was concentrated under reduced pressure, and the residue was purified by column chromatography (ethyl acetate:hexane=3:1), to give compound 15 (29 mg). Yield: 69.4%

$^1$H-NMR(CDCl$_3$-TMS) δ ppm: 0.96 (s, 3H), 1.03 (s, 3H), 1.04 (s, 3H), 1.10 (d, 3H, J=7.6 Hz), 1.40–2.60 (m, 11H), 2.45 (d, 1H, J=18.2 Hz), 3.60 (m, 1H), 3.62 (d, 1H, J=18.2 Hz), 4.47 (s, 2H), 7.09 (br, 1H), 7.67 (s, 1H)

mp:175

EXAMPLE 5
(compound 19)

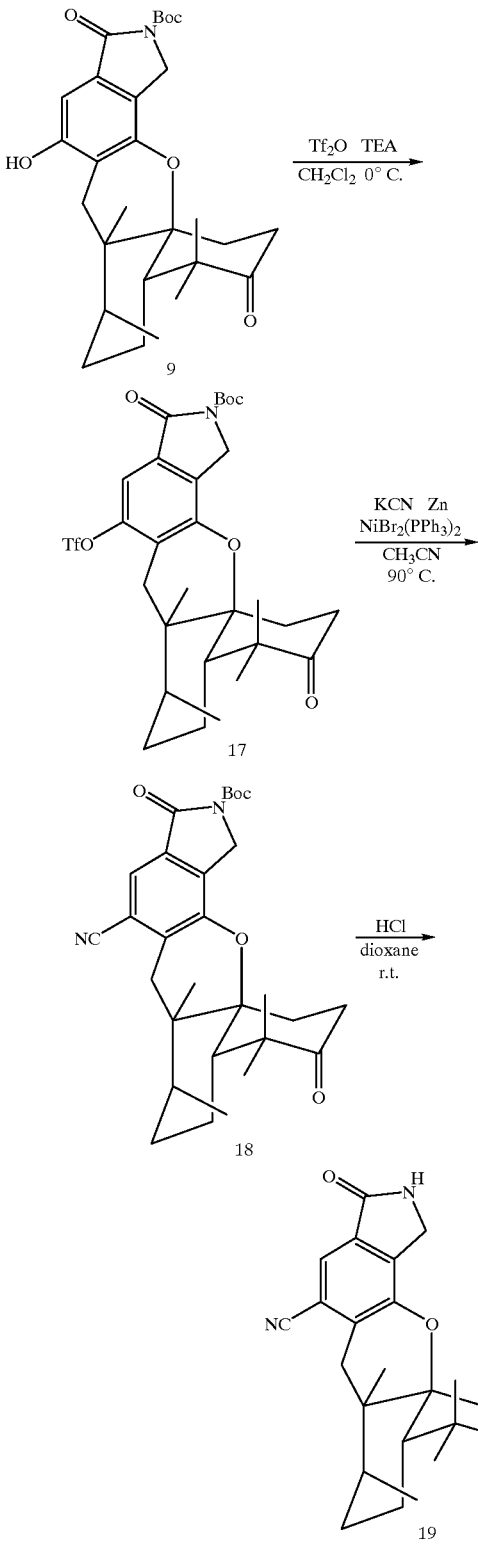

(1) To a solution of compound 9 (460 mg, 0.95 mmol) of Reference Example 4 in dry methylene chloride (20 ml), was added triethylamine (213 mg) under ice cooling, and the mixture was stirred under nitrogen atmosphere for 10 minutes. To the reaction mixture was added triflic anhydride (298 mg) under ice cooling, then which was stirred under nitrogen atmosphere for 3 minutes. The reaction mixture was concentrated under reduced pressure, then the residue was purified by column chromatography (hexane:ethyl acetate=3:1), to give compound 17 (500 mg, 85.4%).

$^1$H-NMR(CDCl$_3$-TMS) δ ppm: 0.96 (s, 3H), 1.03 (s, 3H), 1.14 (d, 3H, J=6.7 Hz), 1.24 (s, 3H), 1.60 (s, 9H), 1.20–2.60 (m, 9H), 2.38 (d, 1H, J=15.8 Hz), 3.10 (m, 1H), 3.38 (d, 1H, J=15.8 Hz), 4.71 (m, 2H), 7.38 (s, 1H)

(2) To a solution of compound 17 (313 mg, 0.51 mmol) in dry acetonitrile (3 ml), were added potassium cyanide (190 mg), dibromo bistriphenylphosphine nickel (38 mg), zinc power (8 mg, 0.01 mmol), and triphenylphosphine (31 mg) under ice cooling, and the mixture was stirred at 60° C. under nitrogen atmosphere for 12 hr. The reaction mixture was concentrated under reduced pressure, then the residue was purified by column chromatography (hexane:ethyl acetate=4:1), to give compound 18 (218 mg). Yield: 87.1%

$^1$H-NMR(CDCl$_3$-TMS) δ ppm: 0.97 (s, 3H), 1.03 (s, 3H), 1.15 (d, 3H, J=7.6 Hz), 1.21 (s, 3H), 1.61 (s, 9H), 1.20–2.60 (m, 9H), 2.50 (d, 1H, J=18.3 Hz), 3.07 (m, 1H), 3.54 (d, 1H, J=18.3 Hz), 4.75 (m, 2H), 7.76 (s, 1H)

(3) Compound 18 (215 mg, 0.44 mmol) was dissolved into 4N dioxane hydrochloride solution (5 ml), and the mixture was stirred at room temperature under nitrogen atmosphere for 1 hr. The reaction mixture was concentrated under reduced pressure, to which diisopropylether was added, then the separating crystal was collected by filtration, dried, to give compound 19 (160 mg). Yield: 93.4%

$^1$H-NMR(CDCl$_3$-TMS) δ ppm: 0.99 (s, 3H), 1.03 (s, 3H), 1.12 (s, 3H), 1.15 (d, 3H, J=7.5 Hz), 1.40–2.60 (m, 9H), 2.53 (d, 1H, J=18.2 Hz), 2.93 (m, 1H), 3.52 (d, 1H, J=18.2 Hz), 4.43 (m, 2H), 6.27 (br, 1H), 7.74 (s, 1H)

dp:285

The reaction steps of Examples 6 and 7 are shown below.

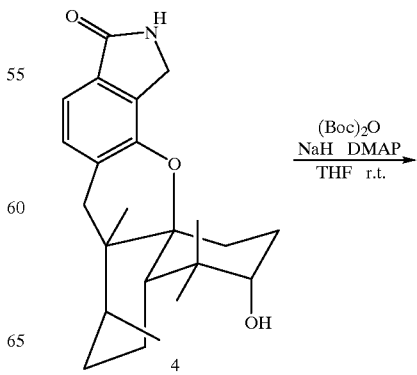

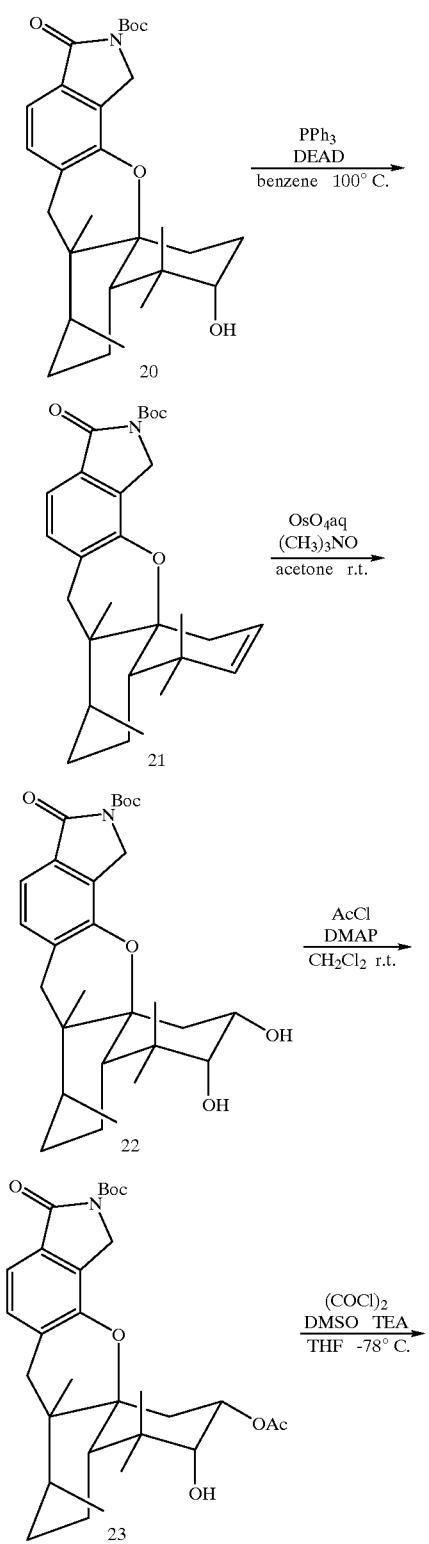
-continued
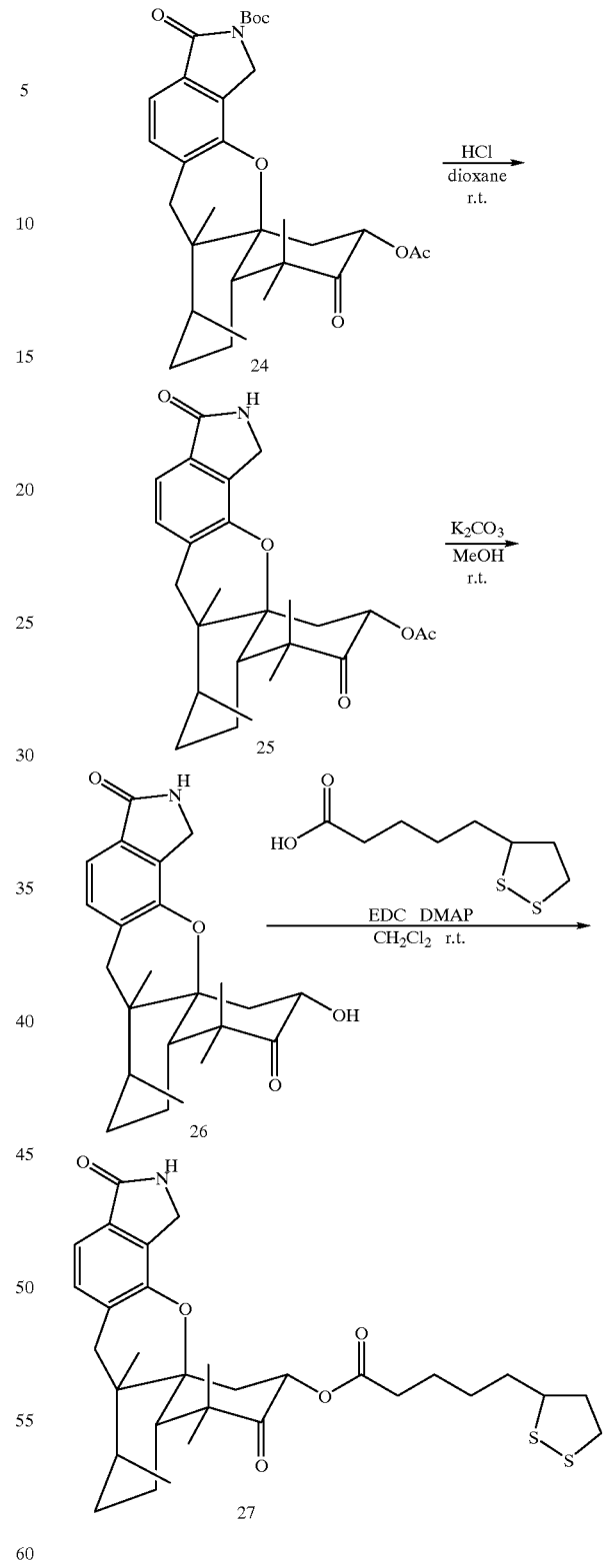

EXAMPLE 6

(compound 26)

(1) To a solution of compound 4 (3.70 g, 10.0 mmol) of Example 1 in dry tetrahydrofran (40 ml), was added sodium hydride (60%, dispersion in mineral oil (0.44 g, 11.0 mmol), and the mixture was stirred at room temperature under nitrogen atmosphere for 30 minutes. To the reaction mixture was added dimethylaminopyridine (0.12 g, 1.0 mmol) and di-t-butyl dicarbonate (2.60 g, 11.2 mmol), and the mixture was stirred under nitrogen atmosphere for 12 hr. To the reaction mixture was added a saturated ammonium chloride solution under ice cooling, then extracted with ethyl acetate. The extract was dried over sodium sulfate, then concentrated under reduced pressure. The residue was purified by column chromatography (hexane:ethyl acetate=7:3) to give compound 20 (3,42 g, 72.8%).

$^1$H-NMR(CDCl$_3$-TMS) δ ppm: 0.91 (s,3H), 1.00 (s,3H), 1.05 (s,3H), 1.15 (d,3H,J=7.6 Hz), 1.60 (s,9H), 1.30–2.50 (m,10H), 2.10 (d,1H,J=18.3 Hz), 2.50 (m,1H), 3.58 (d,1H, J=18.3 Hz), 3.60 (m,1H), 4.67 (m,2H), 7.10 (m,1H), 7.35 (m,1H).

(2) To a solution of compound 20 (3.42 g, 7.3 mmol) in benzene (70 ml), were added triphenylphosphine (3.29 g) and diethyl azodicarboxylate (1.62 ml), and the mixture was stirred at 100° C. under nitrogen atmosphere for 25 minute. Further to the mixture, were added triphenylphosphine (3.29 mg) and diethyl azodicarboxylate (1.62 ml) with stirring at 100° C. under nitrogen atmosphere for 1 hr. The reaction mixture was concentrated under reduced pressure, then the residue was purified by column chromatography (hexane:ethyl acetate=4:1) to give compound 21 (2.60 g). Yield: 79.0%

$^1$H-NMR(CDCl$_3$-TMS) δ ppm: 0.92 (s,3H), 0.93 (s,3H), 0.99 (s,3H), 1.15 (d,3H,J=7.2 Hz), 1.60 (s,9H), 1.30–2.30 (m,7H), 2.15 (d,1H,J=18.3 Hz), 2.62 (m,1H), 3.59 (d,1H,J= 18.3 Hz), 4.60 (d,2H,J=4.2 Hz), 5.43 (m,1H), 5.51 (m,1H), 7.10 (d,1H,J=8.1 Hz), 7.34 (d,1H,J=7.5 Hz)

(3) To a solution of compound 21 (2.60 g, 5.80 mmol) in acetone (150 ml), were added osmium tetroxide solution (40.0 ml) and trimethylamineoxide dihydrate (1.00 g), and the mixture was stirred under nitrogen atmosphere at room temperature for 12 hr. The reaction mixture was filtrated by celite. To the filtrate was added water, then which was extracted with ethyl acetate. The extract was dried over sodium sulfate, then concentrated under reduced pressure. The residue was purified by column chromatography (hexane:ethyl acetate=1:1) to give compound 22 (1.28 g), yield: 45.7%

$^1$H-NMR(CDCl$_3$-TMS) δ ppm: 0.94 (s,3H), 1.06 (s,3H), 1.08 (s,3H), 1.15 (d,3H,J=7.5 Hz), 1.60 (s,9H), 1.20–2.30 (m,12H), 3.59 (s,1H), 4.56 (br,1H), 4.62 (m,2H), 7.11 (d,1H, J=8.1 Hz), 7.35 (d,1H,J=7.8 Hz)

(4) To a solution of compound 22 (1.28 g, 2.60 mmol) in methylene chloride (20 ml), were added dimethylaminopyridine (0.34 g, 2.80 mmol) and acetyl chloride (0.21 g, 2.60 mmol) under ice cooling, and the mixture was stirred under nitrogen atmosphere at room temperature for 12 hr. To the reaction mixture, was added dimethylaminopyridine (0.17 g, 1.40 mmol) and acetyl chloride (68.4 mg, 0.87 mmol) at room temperature, and the mixture was stirred under nitrogen atmosphere at room temperature for 2 hr. To the reaction mixture was added water under ice cooling, then which was extracted with chloroform. The extract was dried over magnesium sulfate, then concentrated under reduced pressure. The residue was purified by column chromatography (hexane:ethyl acetate=1:1), to give compound 23 (1.00 g), Yield: 91.7%

$^1$H-NMR(CDCl$_3$-TMS) δ ppm: 0.93 (s,3H), 1.08 (s,3H), 1.12 (s,3H), 1.14 (d,3H,J=7.5 Hz), 1.60 (s,9H), 1.30–2.40 (m,10H), 2.13 (s,3H), 3.56 (d,1H,J=17.4 Hz), 3.67 (br,1H), 4.70 (m,2H), 5.74 (m,1H), 7.11 (d,1H,J=7.5 Hz), 7.36 (d,1H, J=7.5 Hz)

(5) To a solution of oxalyl chloride (482 mg, 3.79 mmol) in dry tetrahydrofran (10 ml), were added dimethyl sulfoxide (726.7 mg, 9.30 mmol) and compound 23 (1.00 g, 1.90 mmol) at −78° C., and the mixture was stirred under nitrogen atmosphere for 1 hr. To the reaction mixture was added triethylamine (2.1 ml) at −78° C. under nitrogen atmosphere, then which was stirred until the temperature was naturally raised to room temperature. To the reaction mixture was added water, then which was extracted with ethyl acetate. The extract was dried over sodium sulfate, then concentrated under reduced pressure. The residue was purified by column chromatography (hexane:ethyl acetate=2:1), to give compound 24 (0.91 g). Yield: 91.4%

$^1$H-NMR(CDCl$_3$-TMS) δ ppm: 0.99 (s,3H), 1.04 (s,3H), 1.13 (d,3H,J=7.5 Hz), 1.46 (s,3H), 1.60 (s,9H), 1.20–2.08 (m,6H), 2.23 (d,1H,J=15.9 Hz), 2.20 (s,3H), 2.55 (d,2H,J= 9.0 Hz), 3.53 (d,1H,J=15.9 Hz), 4.73 (m,2H), 6.06 (m,1H), 7.17 (d,1H,J=7.5 Hz), 7.43 (d,1H,J=7.5 Hz)

(6) Compound 24 (910 mg, 1.73 mmol) was dissolved into 4N dioxane hydrochloride solution (5 ml), and the mixture was stirred under nitrogen atmosphere at room temperature for 1 hr. The reaction mixture was concentrated under reduced pressure, to which diisopropylether was added, then the separating crystal was collected by filtration, dried, to give compound 25 (700 mg). Yield: 95.0%

$^1$H-NMR(CDCl$_3$-TMS) δ ppm: 1.00 (s,3H), 1.03 (s,3H), 1.13 (d,3H,J=7.5 Hz), 1.45 (s,3H), 1.20–2.20 (m,5H), 2.23 (d,1H,J=18.7 Hz), 2.20 (s,3H), 2.55 (d,2H,J=9.0 Hz), 3.49 (s,1H), 3.55 (d,1H,J=18.7 Hz), 4.48 (br,2H), 6.06 (br,1H), 6.08 (m,1H), 7.17 (d,1H,J=7.5 Hz), 7.41 (d,1H,J=7.5 Hz)

(7) To a solution of compound 25 (700 mg, 1.65 mmol) in methanol (5 ml), was added potassium carbonate (250 mg, 1.81 mmol), and the mixture was stirred at room temperature for 2 hr. To the reaction mixture was added water, then extracted with chloroform. The extract was dried over sodium sulfate, then concentrated under reduced pressure. The residue was purified by column chromatography (chloroform:methanol=50:1) to give compound 26 (550 mg). Yield: 87.2%

$^1$H-NMR(CDCl$_3$-TMS) δ ppm: 1.00 (s,3H), 1.08 (s,3H), 1.12 (d,3H,J=7.5 Hz), 1.41 (s,3H), 1.20–2.30 (m,5H), 2.23 (d,1H,J=18.7 Hz), 2.75 (m,1H), 2.55 (d,2H,J=9.0 Hz), 3.51 (d,1H,J=18.7 Hz), 3.66 (d,1H,J=3.6 Hz), 4.40 (m,2H), 5.09 (m,1H), 6.40 (br,1H), 7.17 (d,1H,J=7.8 Hz), 7.41 (d,1H,J= 7.8 Hz)

EXAMPLE 7

(compound 27)

To a solution of compound 26 (50.0 mg, 0.13 mmol) of Example 6 in dry methylene chloride (15 ml), were added EDC (40 mg, 0.21 mmol), dimethylaminopyridine (10 mg, 0.08 mmol), and dlα-lipoic acid (50 mg, 0.24 mmol), and the mixture was stirred under nitrogen atmosphere at room temperature for 5 hr. The reaction mixture was concentrated under reduced pressure, then the residue was purified by plate (chloroform:methanol=50:1), to give compound 27 (39.8 mg). Yield: 53.4%

$^1$H-NMR(CDCl$_3$-TMS) δ ppm: 1.00 (s,3H), 1.03 (s,3H), 1.13 (d,3H,J=7.2 Hz), 1.49 (s,3H), 1.20–2.20 (m,13H), 2.25 (d,1H,J=17.7 Hz), 2.50 (m,5H), 3.15 (m,2H), 3.55 (d,1H,J= 17.7 Hz), 3.60 (m,1H), 4.45 (m,2H), 6.09 (m,2H), 7.19 (d,1H,J=7.8 Hz), 7.41 (d,1H,J=7.8 Hz)

The reaction steps of Examples 8 and 9 are shown below.

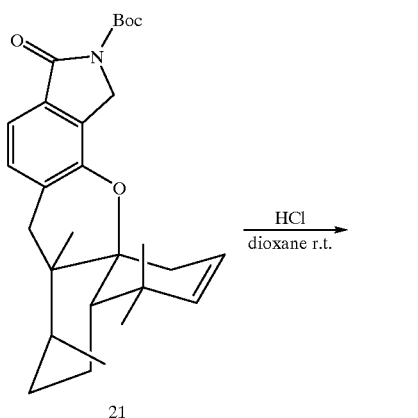

21

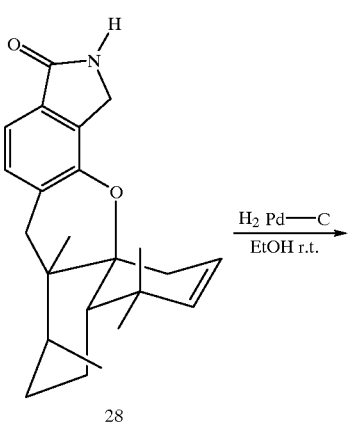

28

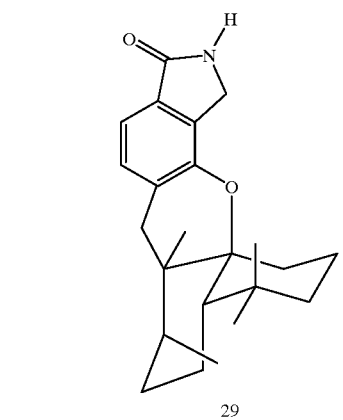

29

EXAMPLE 8

(compound 28)

Compound 21 (100.0 mg, 0.22 mmol) was dissolved into 4N dioxane hydrochloride solution (5 ml), and the mixture was stirred under nitrogen atmosphere at room temperature for 1 hr. The reaction mixture was concentrated under reduced pressure, to which diisopropylether was added, then the separating crystal was collected by filtration, dried, to give compound 28 (55 mg). Yield: 70.7%

$^1$H-NMR(CDCl$_3$-TMS) δ ppm: 0.92 (s,3H), 0.93 (s,3H), 0.98 (s,3H), 1.15 (d,3H,J=7.2 Hz), 1.30–2.30 (m,7H), 2.18 (d,1H,J=18.3 Hz), 2.62 (m,1H), 3.59 (d,1H,J=18.3 Hz), 4.30 (s,2H), 5.40 (m,1H), 5.50 (m,1H), 6.00 (br,1H), 7.10 (d,1H, J=8.1 Hz), 7.34 (d,1H,J=7.5 Hz)

mp:260 Elementary Analysis (C$_{23}$H$_{29}$NO$_2$, 0.2 H$_2$O) Calcd: C,7780; H,8.35; N,3.94 Found: C,77.82; H,8.50; N,3.98

EXAMPLE 9

(compound 29)

To a solution 28 (34 mg, 0.097 mmol) in 99.5% ethanol (60 ml), was added 10% palladium carbon (10 mg), and the mixture was stirred under hydrogen atmosphere at room temperature for 2 hr. The reaction mixture was filtrated by celite, then concentrated under reduced pressure. To the residue was added diisopropylether, then the separating crystal was collected by filtration, dried, to give compound 29 (30 mg). Yield: 87.7%

$^1$H-NMR(CDCl$_3$-TMS) δ ppm: 0.83 (s,3H), 0.89 (s,3H), 1.08 (s,3H), 1.14 (d,3H,J=6.6 Hz), 1.30–2.20 (m,11H), 2.10 (d,1H,J=18.3 Hz), 3.49 (m,1H), 3.59 (d,1H,J=18.3 Hz), 4.30 (s,2H), 5.95 (br,1H), 7.10 (m,1H), 7.34 (m,1H)

Elementary Analysis (C$_{23}$H$_{31}$NO$_2$, 0.3 H$_2$O) Calcd: C,76.97; H,8.97; N,3.90 Found: C,77.00; H,8.96; N,3.81

The reaction steps of Examples 10 and 11 are shown below.

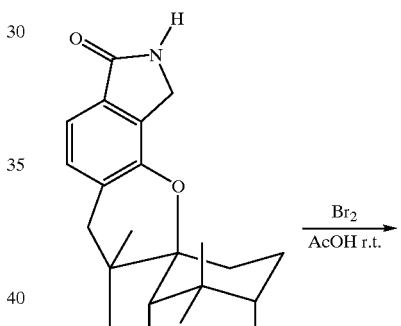

4

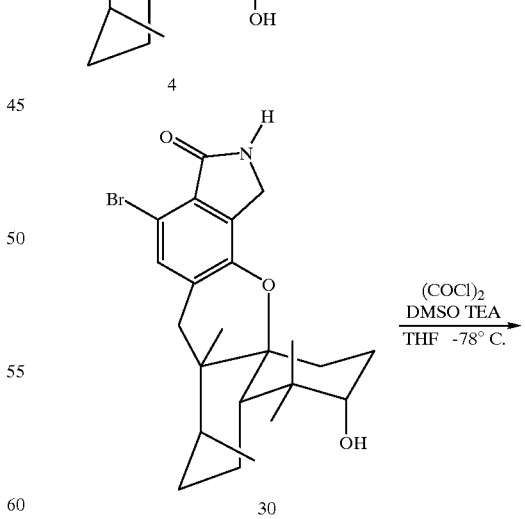

30

-continued

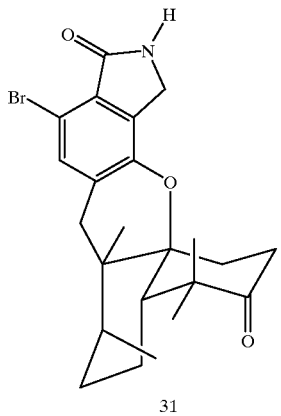

31

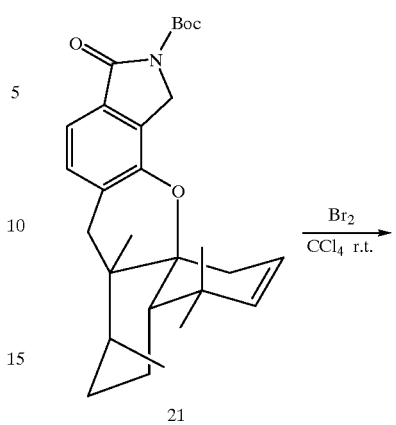

EXAMPLE 10

(compound 30)

To a solution of compound 4 (1 g, 2.71 mmol) of Example 1 in acetic acid 30 ml, was added bromine (432 mg, 2.71 mmol) under ice cooling, and the mixture was stirred under nitrogen atmosphere at room temperature for 2 hr. The reaction mixture was concentrated under reduced pressure, then ethyl acetate was added to the residue. The separating crystal was collected by filtration, purified by column chromatography (chloroform:methanol=100:3) to give compound 30 (800 mg). Yield: 65.9%

$^1$H-NMR(CDCl$_3$-TMS) δ ppm: 0.91 (s,3H), 1.00 (s,3H), 1.02 (s,3H), 1.15 (d,3H,J=7.2 Hz), 1.30–2.60 (m,11H), 2.08 (d,1H,J=18.3 Hz), 3.55 (d,1H,J=18.3 Hz), 3.57 (m,1H), 4.30 (s,2H), 6.20 (br,1H), 7.26 (s,1H)

EXAMPLE 11

(compound 31)

To a solution of oxalyl chloride (56.6 mg, 0.45 mmol) in dry tetrahydrofran (4 ml), was added dimethyl sulfoxide (85.5 mg, 1.09 mmol) and compound 30 (100.0 mg, 0.22 mmol) at −78° C., and the mixture was stirred under nitrogen atmosphere for 1 hr. To the reaction mixture was added triethylamine (0.24 ml) at −78° C., and the mixture was stirred under nitrogen atmosphere until the temperature was naturally raised to room temperature. To the reaction mixture was added water, then which was extracted with ethyl acetate, and concentrated under reduced pressure. The residue was purified by plate (ethyl acetate:hexane=2:1) to give compound 31 (33.8 mg). Yield: 34.0%

$^1$H-NMR(CDCl$_3$-TMS) δ ppm: 0.97 (s,3H), 1.01 (s,3H), 1.11 (s,3H), 1.15 (d,3H,J=7.2 Hz), 1.30–2.60 (m,9H), 2.20 (d,1H,J=18.3 Hz), 2.95 (m,1H), 3.49 (d,1H,J=18.3 Hz), 4.31 (s,2H), 6.35 (br,1H), 7.28 (s,1H)

Elementary Analysis (C$_{23}$H$_{28}$BrNO$_3$, 0.3 H$_2$O) Calcd: C,61.15; H,6.38; Br,17.69; N,3.10 Found C,60.99; H,6.43; Br,17.91; N,3.09

The reaction steps of Examples 12 and 13 are shown below.

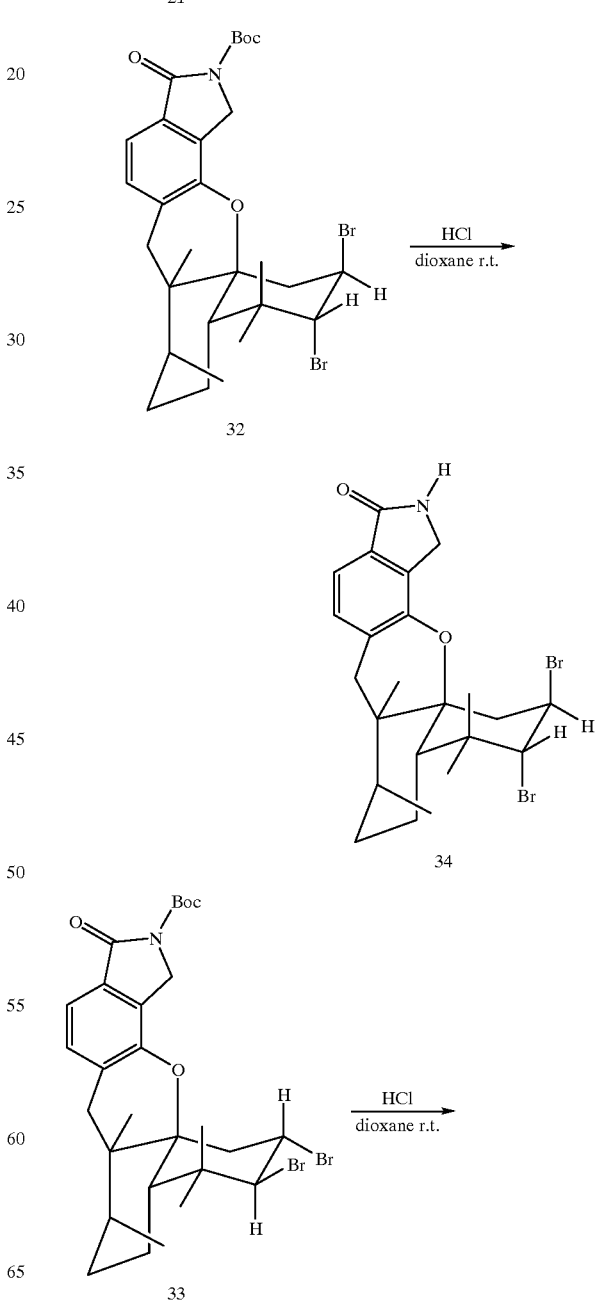

EXAMPLE 12
(compound 34)

(1) To a solution of compound 21 (200 mg, 0.443 mmol) in carbon tetrachloride (15 ml), was added bromine (71 mg, 0.444 mmol) under ice cooling, and the mixture was stirred under nitrogen atmosphere at room temperature for 4 hr. The reaction mixture was concentrated under reduced pressure, then the residue was purified by column chromatography (hexane:ethyl acetate=4:1), to give compound 32 (30 mg, yield: 11.1%) from the initial eluent and compound 33 (150 mg, yield: 55.4%) from the next.

Compound 32

$^1$H-NMR(CDCl$_3$-TMS) δ ppm: 0.82 (d,3H,J=6.6 Hz), 1.03 (s,3H), 1.08 (s,3H), 1.26 (s,3H), 1.30–1.85 (m,5H), 1.61 (s,9H), 2.08 (m,1H), 2.45 (m,1H), 2.59 (d,1H,J=18.0 Hz), 2.90 (d,1H), 2.92 (m,1H), 4.54 (m,1H), 4.73 (d,1H,J=9.4 Hz), 4.75 (m,2H), 7.09 (d,1H), 7.38 (d,1H)

Compound 33

$^1$H-NMR(CDCl$_3$-TMS) δ ppm: 0.91 (s,3H), 1.13 (s,3H), 1.16 (d,3H,J=7.8 Hz), 1.24 (s,3H), 1.30–2.05 (m,6H), 1.61 (s,9H), 2.15 (d,1H,J=17.8 Hz), 2.68 (s,1H), 2,71 (s,1H), 3.50 (d,1H,J=17.8 Hz), 4.33 (d,1H,J=11.4 Hz), 4.73 (m,2H), 4.82 (m,1H), 7.10 (d,1H), 7.40 (d,1H)

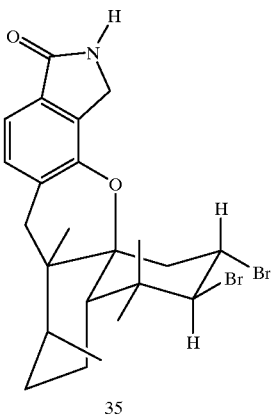

35

(2) Compound 32 (30 mg, 0.049 mmol) was dissolved into 4N dioxane hydrochloride solution (2 ml), and the mixture was stirred under nitrogen atmosphere at room temperature for 1 hr. The reaction mixture was concentrated under reduced pressure, to which diisopropylether was added, then the separating crystal was collected by filtration, dried, to give compound 34 (20 mg). Yield: 80.0%

$^1$H-NMR(CDCl$_3$-TMS) δ ppm: 0.82 (s,3H), 1.03 (s,3H), 1.07 (s,3H), 1.13 (d,3H,J=6.3 Hz), 1.30–2.20 (m,5H), 2.08 (m,1H), 2.58 (m,2H), 2.89 (m,2H), 4.54 (m,2H), 4.80 (m,2H), 6.10 (br,1H), 7.09 (d,1H), 7.38 (d,1H)

EXAMPLE 13
(compound 35)

Compound 33 (150 mg, 0.245 mmol) of Example 12 (1) was dissolved into 4N dioxane hydrochloride (4 ml), and the mixture was stirred under nitrogen atmosphere at room temperature for 1 hr. The reaction mixture was concentrated under reduced pressure, to which diisopropylether was added, then the separating crystal was collected by filtration, dried, to give compound 35 (100 mg). Yield: 79.7%

$^1$H-NMR(CDCl$_3$-TMS) δ ppm: 0.93 (s,3H), 1.13 (s,3H), 1.16 (d,3H,J=7.8 Hz), 1.24(s,3H), 1.30–2.05 (m,6H), 2.15 (d,1H,J=17.8 Hz), 2.68 (s,1H), 2,71 (s,1H), 3.50 (d,1H,J=17.8 Hz), 4.33 (d,1H,J=11.1 Hz), 4.45 (m,2H), 4.80 (m,1H), 6.10 (br,1H), 7.10 (d,1H), 7.40 (d,1H)

EXAMPLE 14
(compound 36)

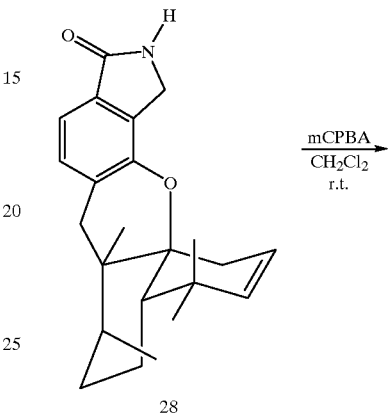

28

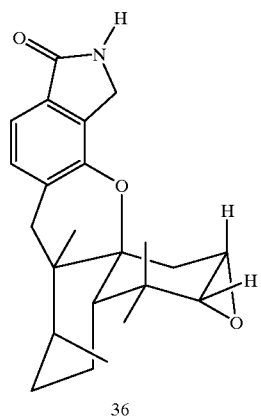

36

To a solution of compound 28 of Example 8 (100 mg, 0.284 mmol) in methylene chloride (20 ml), m-chloroperbenzoic acid (68 mg, 0.394 mmol) was added under ice cooling and nitrogen atmosphere at room temperature, then stirred for 24 hr. To the reaction mixture was added a solution of sodium thiosulfate and a solution of sodium bicarbonate, then stirred at room temperature for 1 hr. To the obtained mixture was added water, then extracted with methylene chloride. The extract was dried over sodium sulfate, then concentrated under reduced pressure. The residue was purified by column chromatography (hexane:ethyl acetate=1:1), to give compound 36 (80 mg, 76.6%).

$^1$H-NMR(CDCl$_3$-TMS) δ ppm: 0.91 (s,3H), 1.02 (s,3H), 1.10 (s,3H), 1.13 (d,3H), 1.30–2.30 (m,7H), 2.13 (d,1H,J=17.4 Hz), 2.46 (d,1H,J=15.6 Hz), 2.89 (d,1H), 3.39 (m,1H), 3.50 (d,1H,J=17.1 Hz), 4.33 (s,2H), 6.24 (br,1H), 7.11 (d,1H,J=8.1 Hz), 7.33 (d,1H,J=7.5 Hz)

EXAMPLE 15–17
(compound 49, 50, 51)
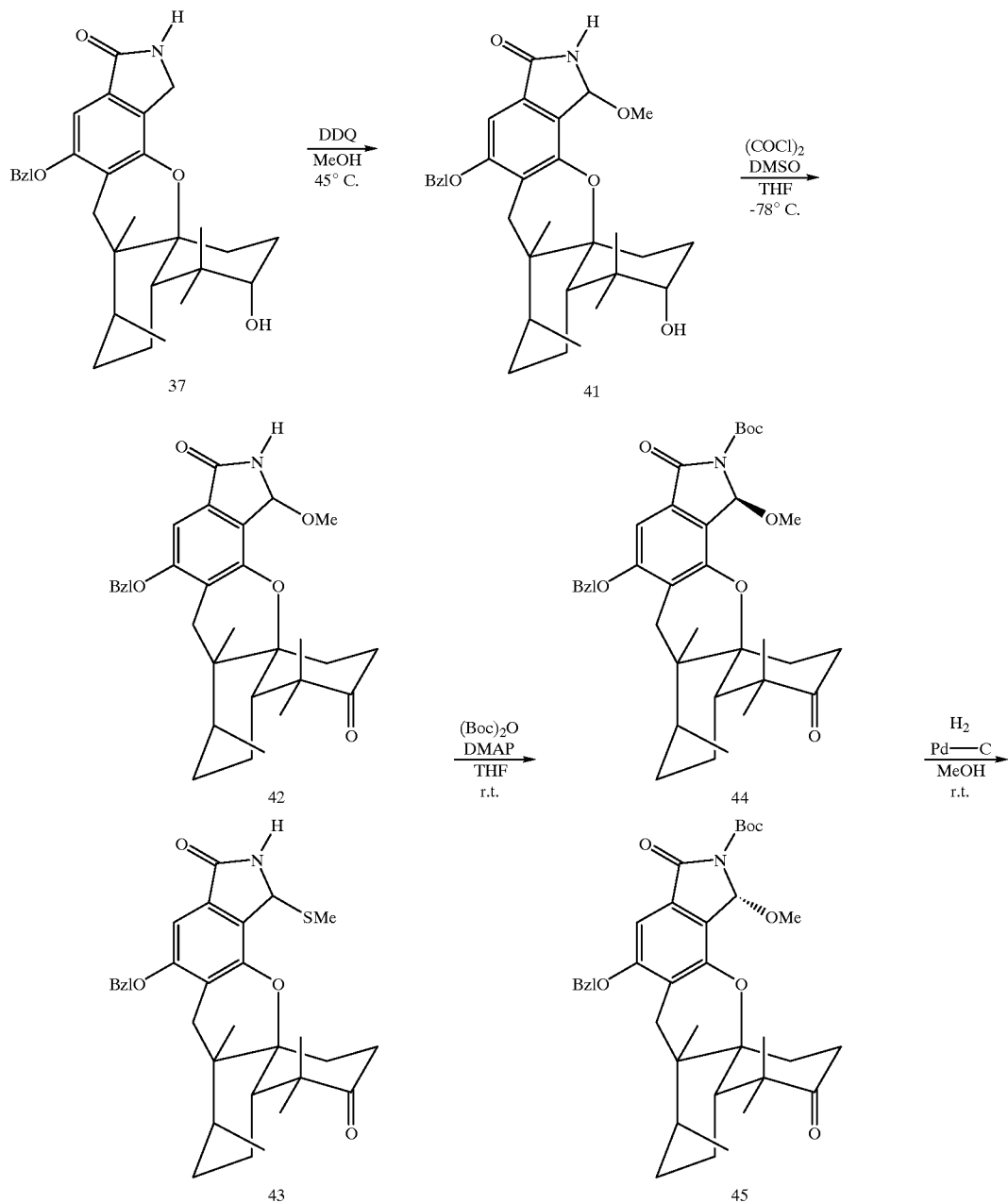

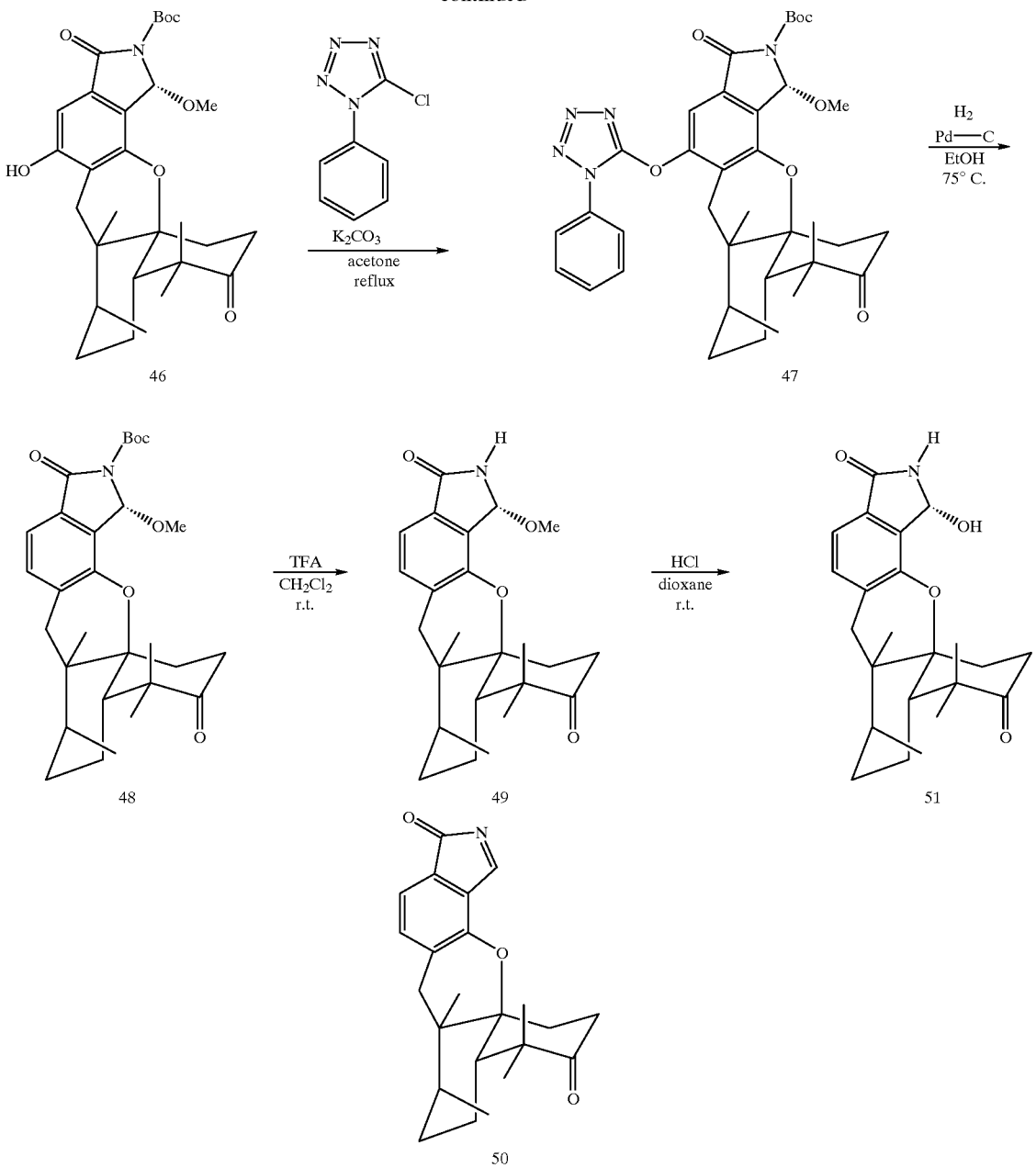

(1) To a solution of compound 37 (500 mg, 1.05 mmol) of Reference Example 3 (1) in methanol (50 ml), 2,3-dichloro-5,6-dicyanobenzoquinone (DDQ) was added, then the mixture was stirred at 45° C. for 25 hr. After cooling, methanol in the mixture was evaporated to be half amount, to which water was added, then dried over sodium sulfate. The residue is purified by column chromatography (toluene:ethyl acetate=1:1), to give compound 41 (439 mg, 83.0%).

$^1$H-NMR(CDCl$_3$-TMS) δ ppm: 0.92 (s,3H), 0.99 (s,3H), 1.07 (s,3H), 1.14 (d,3H,J=7.4 Hz), 2.28 (d,1H,J=18.0 Hz), 3.08 (s,3H), 3.19 (d,1H,J=18.0 Hz), 3.57 (br,1H), 5.11 (s,2H), 6.04 (s,1H), 6.32 (m,1H), 6.95 (s,1H), 7.35–7.50 (m,5H)

(2) To a solution of oxalyl chloride (1.98 g, 15.6 mmol) in dried tetrahydrofran (10 ml), were added dimethyl sulfoxide (2.78 g, 35.6 mmol) and compound 41 (4.00 g, 7.91 mmol) at −78° C., then the mixture was stirred under nitrogen atmosphere for 1 hr. To the reaction mixture, triethylamine (7.80 ml) was added at −78° C. under nitrogen atmosphere, then allowed to be at room temperature. To the obtained mixture, water was added, then extracted with ethyl acetate. The extract was washed with a saturated saline, then dried over anhydrous magnesium. The residue was concentrated under reduced pressure, then purified by column chromatography (ethyl acetate:hexane=1:2), to give compound 42 (1.72 g, 43.2%) from the first eluent and compound 43 (1.77 g, 43.1%) from the next).

Compound 42

$^1$H-NMR(CDCl$_3$-TMS) δ ppm: 0.97 (s,3H), 1.00 (s,3H), 1.14 (d,3H,J=7.5 Hz), 1.23 (s,3H), 2.34 (d,1H,J=20.0 Hz), 3.17 (s,3H), 3.13 (d,1H,J=18.0 Hz), 5.14 (s,2H), 6.01 (s,1H), 6.08 (s,1H), 7.01 (s,1H), 7.40 (m,5H)

Compound 43

Elementary Analysis ($C_{31}H_{37}NO_4$, 0.25 $H_2O$) Calcd: C,71.03; H,7.21; N,2.67; S,6.12 Found: C,70.90; H,7.36; N,2.79; S,5.81 LSIMS: m/z 520[M+H]$^+$ $^1$H-NMR(CDCl$_3$-TMS) δ ppm: 0.96 (s,3H), 1.00 (s,3H), 1.11 (d,3H,J=7.5 Hz), 1.21 (s,3H), 1.68 (s,3H), 2.36 (d,1H, J=18.3 Hz), 3.14 (d,1H,J=18.6 Hz), 3.25 (m,1H), 5.11 (s,2H), 5.59 (s,1H), 6.06 (br,1H), 7.01 (s,1H), 7.42 (m,5H (3) To a solution of compound 42 (1.72 g, 3.41 mmol) in dried tetrahydrofran (20 ml), dimethylaminopyridine (0.25 g, 2.04 mmol) was added and the mixture was stirred under nitrogen atmosphere at room temperature for 30 min. To the reaction mixture, di-t-butyl dicarbonate (1.0 g, 4.31 mmol) was added and the mixture was stirred under nitrogen atmosphere at room temperature for 2 hr. The residue was concentrated under reduced pressure was purified by column chromatography (hexane:ethyl acetate=2:1), to obtain compound 44 (0.36 g, 17.0%) from the first eluent and compound 45 (1.54 g, 72.6%) from the next.

Compound 44

$^1$H-NMR (CDCl$_3$-TMS) δ ppm: 0.88 (s,3H), 1.01 (s,3H), 1.10 (d,3H,J=7.5 Hz), 1.41 (s,3H), 1.60 (s,9H), 2.34 (d,1H, J=18.0 Hz), 3.14 (s,3H), 3.19 (d,1H,J=18.0 Hz), 5.10, 5.14 (d-d,2H,J=13.8 Hz), 6.38 (s,1H), 7.00 (s,1H), 7.40 (m,5H)

Compound 45

$^1$H-NMR-CDCl$_3$-TMS) δ ppm: 0.97 (s,3H), 1.00 (s,3H), 1.11 (d,3H,J=7.5 Hz), 1.32 (s,3H), 1.60 (s,9H), 2.34 (d,1H, J=18.0 Hz), 3.14 (d,1H,J=18.0 Hz), 3.22 (s,3H), 5.12 (s,2H), 6.32 (s,1H), 7.01 (s,1H), 7.44 (m,5H)

(4) To a solution of compound 45 (1.48 g, 2.45 mmol) in methanol (40 ml), 10% palladium carbon (0.34 g) was added and the mixture was stirred under hydrogen atmosphere at room temperature for 1 hr, to which 10% palladium carbon (0.18 g) was further added, then stirred in the same way. The reaction mixture was filtrated with celite, then the filtrate was concentrated under reduced pressure. The residue was purified by column chromatography (chloroform:methanol= 50:1), to give compound 46 (1.20 g, 95.3%).

$^1$H-NMR(CDCl$_3$-TMS) δ ppm: 0.98 (s,3H), 1.00 (s,3H), 1.13 (d,3H,J=7.8 Hz), 1.32 (s,3H), 1.60 (s,9H), 2.31 (d,1H, J=18.0 Hz), 2.45 (m,1H), 3.17 (d,1H,J=17.7 Hz), 3.22 (s,3H), 6.26 (s,1H), 6.32 (s,1H), 6.98 (s,1H)

(5) To a solution of compound 46 (1.15 g, 2.24 mmol) in acetone (50 ml), were added potassium carbonate (0.45 g, 3.26 mmol) and 5-chloro-1-phenyl-1H-tetrazole (0.45 g, 2.49 mmol), with a stirring at 70° C. under nitrogen atmosphere for 5 hr. The reaction mixture was filtrated with celite and the filtrate was concentrated under reduced pressure. The residue was purified by column chromatography (hexane:ethyl acetate=2:1), to give compound 47 (1.47 g, 99.9%).

$^1$H-NMR(CDCl$_3$-TMS) δ ppm: 0.99 s,3H), 1.03 (s,3H), 1.11 (d,3H,J=7.2 Hz), 1.35 (s,3H), 1.61 (s,9H), 2.20 (d,1H, J=17.4 Hz), 2.45 (m,1H), 3.27 (d,1H,J=17.4 Hz), 3.29 (s,3H), 6.37 (s,1H), 7.61 (m,3H), 7.78 (m,2H)

(6) To a solution of compound 47 (1.47 g, 2.34 mmol) in 99.5% ethanol (60 ml), 10% palladium carbon (0.35 g) was added and the mixture was stirred under hydrogen atmosphere at 75° C. for 5 hr. The reaction mixture was filtrated with celite, then the filtrate was concentrated under reduced pressure. The residue was purified by column chromatography (chloroform:methanol=20:1), to give compound 48 (0.95 g, 85.8%).

$^1$H-NMR(CDCl$_3$-TMS) δ ppm: 0.98 (s,3H), 1.01 (s,3H), 1.13 (d,3H,J=7.8 Hz), 1.35 (s,3H), 1.61 (s,9H), 2.22 (d,1H, J=17.7 Hz), 2.45 (m,1H), 3.23 (s,3H), 3.31 (m,1H), 3.52 (d,1H,J=17.7 Hz), 6.37 (s,1H), 7.22 (d,1H), 7.38 (d,1H,J= 7.5 Hz)

(7) To a solution of compound 48 (170 mg, 0.34 mmol) in methylene chloride (5 ml), trifluoro acetic acid (2 ml) was added and the mixture was stirred at room temperature for 30 minutes. To the reaction mixture, water was added, then which was extracted with ethyl acetate. The extract was washed with a saturated saline, dried over anhydrous magnesium sulfate, and concentrated under reduced pressure. The residue was purified by column chromatography (ethyl acetate:hexane=1:2), to obtain compound 49 of Example 15 (74 mg, 54.4%) from the first eluent and compound 50 of Example 16 (25 mg, 20.0%) from the next.

Compound 49

Elementary Analysis ($C_{24}H_{30}NO_4$, 0.25 $H_2O$) Calcd: C,71.88; H,7.67; N,3.49 Found: C,72.007; H,8.04N,3.45

$^1$H-NMR(CDCl$_3$-TMS) δ ppm: 0.97 (s,3H), 1.01 (s,3H), 1.13 (d,3H,J=7.8 Hz), 1.30 (s,3H), 2.23 (d,1H,J=17.7 Hz), 2.45 (m,1H), 3.13 (s,3H), 3.20 (m,1H), 3.51 (d,1H,J=17.4 Hz), 6.04 (s,1H), 6.18 (s,1H), 7.21 (d,1H,J=7.5 Hz), 7.34 (d,1H,J=7.5 Hz)

Compound 50

Elementary Analysis ($C_{23}H_{26}NO_3$, 0.75 $H_2O$) Calcd: C,73.08; H,7.27; N,3.71 Found: C,72.70; H,7.39; N,3.49 LSIMS: m/z 365[M+H]$^+$ $^1$H-NMR(CDCl$_3$-TMS) δ ppm: 0.86 (s,3H), 0.94 (s,3H), 1.13 (d,3H,J=7.8 Hz), 1.14 (s,3H), 2.20 (d,1H,J=17.1 Hz), 2.58 (m,1H), 2.74 (m,1H), 3.02 (m,1H), 3.36 (d,1H,J=18.0 Hz), 6.00 (s,1H), 7.11 (d,1H,J=7.8 Hz), 7.26 (d,1H,J=7.5 Hz), 9.05 (br,1H)

(8) To a solution of compound 49 (40 mg, 0.08 mmol) of Example 15 in dioxane (2 ml), 4N hydrochloric acid (0.1 ml) was added and the mixture was stirred under nitrogen atmosphere at room temperature for 6 hr. The reaction mixture was concentrated under reduced pressure, then the residue was purified with plate (ethyl acetate:hexane=2:1), to give compound 51 of Example 17 (21 mg, 54.4%).

Elementary Analysis ($C_{23}H_{29}NO_4$, 0.75 $H_2O$) Calcd: C,69.58; H,7.74; N,3.53 Found: C,69.53; H,7.93; N,3.31

$^1$H-NMR(CDCl$_3$-TMS) δ ppm: 1.00 (s,3H), 1.04 (s,3H), 1.11 (d,3H,J=7.8 Hz), 1.21 (s,3H), 2.25 (d,1H,J=17.1 Hz), 2.45 (m,1H), 2.60 (m,1H), 3.00 (m,1H), 3.42 (d,1H,J=17.1 Hz), 6.07 (d,1H,J=6.0 Hz), 6.29 (br,1H), 7.19 (d,1H), 7.29 (d,1H)

EXAMPLE 18 AND 19

(compound 52, 53)

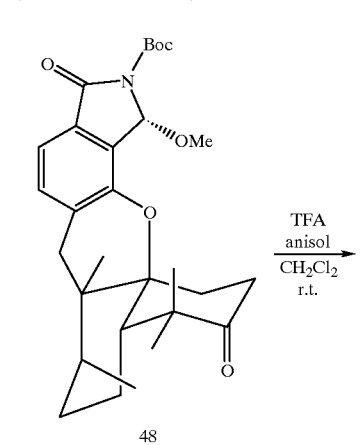

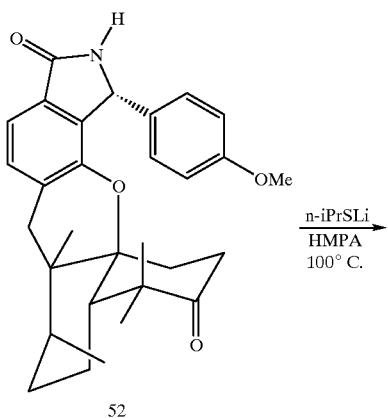

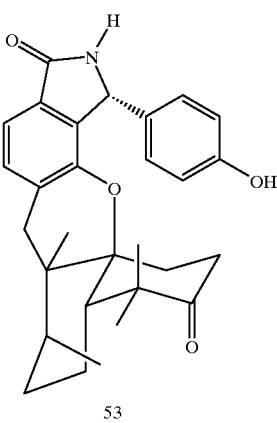

(1) To a solution of compound 48 (588 mg, 1.18 mmol) of Example 15(6) in methylene chloride (6 ml), were added anisole (0.1 ml) and trifluoro acetic acid (15.0 ml) and the mixture was stirred at room temperature for 30 min. To the reaction mixture, a saturated solution of sodium bicarbonate was added, then extracted with ethyl acetate. The organic layer was washed with a saturated saline, dried over anhydrous magnesium sulfate, then concentrated under reduced pressure. The residue was purified by column chromatography (ethyl acetate:hexane=3:1), to give compound 52 of Example 18 (460 mg, 82.0%).

Elementary Analysis ($C_{30}H_{35}NO_4$, 1.5 $H_2O$) Calcd: C,71.97; H,7.65; N,2.80 Found: C,71.69; H,7.33; N,2.78

$^1$H-NMR(CDCl$_3$-TMS) δ ppm: 0.68 (s,3H), 0.99 (s,3H), 1.02 (d,3H,J=7.2 Hz), 1.28 (s,3H), 2.14 (d,1H,J=17.7 Hz), 2.55 (m,1H), 3.49 (m,1H), 3.49 (d,1H,J=17.7 Hz), 3.79 (s,3H), 5.52 (s,1H), 6.33 (br,1H), 6.80 (d,2H,J=8.4 Hz), 7.09 (d,2H,J=8.7 Hz), 7.17 (d,1H,J=7.5 Hz), 7.40 (d,1H,J=7.8 Hz)

(2) To a solution of compound 52 (200 mg, 0.42 mmol) in HMPA (0.5 ml), 1N lithium isopropylmercaptide HMPA solution (0.4 ml) was added and the mixture was stirred under nitrogen atmosphere at 100° C. for 6 hr. To the reaction mixture was added a saturated solution of a saturated solution of sodium bicarbonate, then extracted with ethyl acetate. The extract was washed with a saturated saline, dried over magnesium sulfate, then concentrated under reduced pressure. The residue was purified by column chromatography (ethyl acetate:hexane=3:2), to give compound 53 of Example 19 (20 mg, 10.3%).

Elementary Analysis ($C_{29}H_{33}NO_4$, 0.5 $H_2O$) Calcd: C,74.33; H,7.31; N,2.99 Found: C,74.59; H,7.52 N,3.14

$^1$H-NMR(CDCl$_3$-TMS) δ ppm: 0.67 (s,3H), 0.99 (s,3H), 1.02 (d,3H,J=7.2 Hz), 1.27 (s,3H), 2.14 (d,1H,J=17.1 Hz), 2.55 (m,1H), 3.46 (d,1H,J=17.7 Hz), 5.49 (s,1H), 5.92 (br,1H), 6.23 (s,1H), 6.73 (d,2H,J=8.4 Hz), 7.00 (d,2H,J=8.4 Hz), 7.17 (d,1H,J=7.5 Hz), 7.40 (d,1H,J=7.8 Hz)

EXAMPLE 20 AND 21

(compound 54, 55)

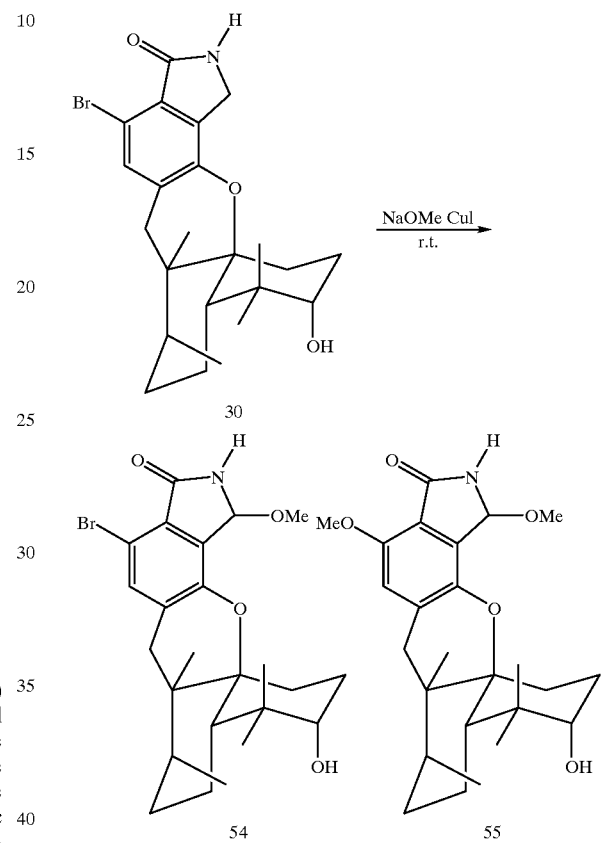

To a solution of compound 30 (30 mg) of Example 10 in methanol, were added CuI (30 mg) and 25 wt % of NaOMe solution, with stirring at room temperature. After 15 minutes, an aqueous solution of ammonium chloride was added thereto, then extracted with chloroform. The chloroform layer was dried over anhydrous magnesium sulfate and concentrated under reduced pressure. The residue was purified by column chromatography, to give compound 54 (10 mg, 31.3%) form the first eluent and compound 55 (2.4 mg, 8.4%) from the next.

Compound 54

$^1$H-NMR(CDCl$_3$-TMS) δ ppm: 0.92 (s,3H), 1.01 (s,3H), 1.08 (s,3H), 1.15 (d,3H,J=7.5 Hz), 1.30–2.60 (m,11H), 2.08 (d,1H,J=18.3 Hz), 3.06 (s,3H), 3.55 (d,1H,J=18.3 Hz), 3.57 (m,1H), 5.99 (d,1H,J=1.5 Hz), 6.19 (br,1H), 7.29 (s,1H)

Compound 55

$^1$H-NMR(CDCl$_3$-TMS) δ ppm: 0.94 (s,3H), 1.00 (s,3H), 1.09 (s,3H), 1.16 (d,3H,J=7.2 Hz), 1.30–2.65 (m,10H), 2.08 (d,1H,J=18.3 H), 3.06 (s,3H), 3.55 (d,1H,J=18.3 Hz), 3.57 (m,1H), 3.90 (s,3H), 5.97 (d,1H), 6.00 (s,1H), 6.66 (br,1H), 7.27 (s,1H)

EXAMPLE 22 AND 23

(compound 56, 57)

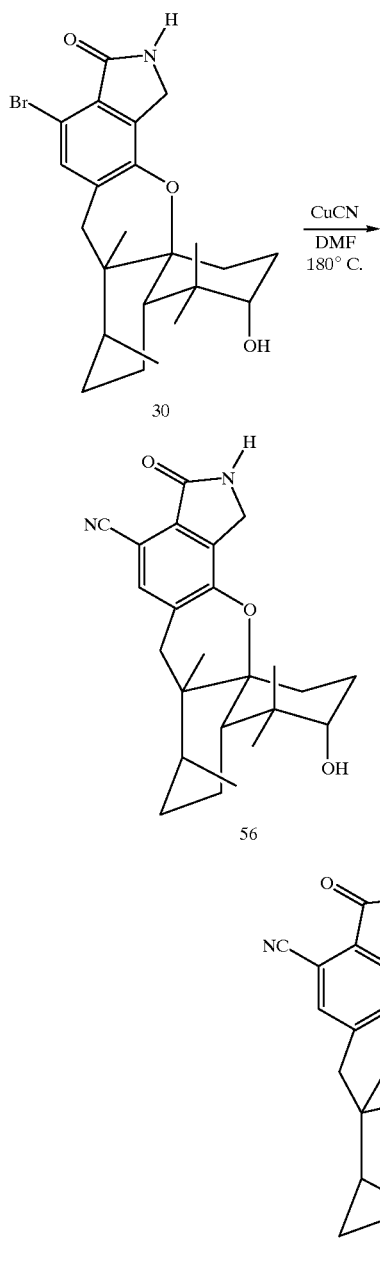

(1) To a solution of compound 30 (200 mg) in dimethyl formamide, was added copper cyanide (48 mg) with stirring at 180° C. After 1 hour, an aqueous solution of potassium cyanide was added thereto, then extracted with chloroform. The chloroform layer was dried over anhydrous magnesium sulfate and concentrated under reduced pressure. The residue was purified by column chromatography (chloroform:methanol=100:2), to give compound 56 (97.5 mg, 55.4%).

$^1$H-NMR(CDCl$_3$-TMS) δ ppm: 0.91 (s,3H), 1.01 (s,6H), 1.16 (d,3H,J=7.8 Hz), 1.35–2.50 (m,11H), 2.14 (d,1H,J=17.4 Hz), 3.58 (d,1H,J=17.1 Hz), 3.59 (s,2H), 4.40 (s,2H), 7.44 (s,1H)

(2) To a solution of compound 56 (79 mg) in acetone, was added a solution of chromic acid with stirring at −10° C. After 30 minutes, isopropyl alcohol was added thereto, then extracted with ethyl acetate. The ethyl acetate layer was dried over anhydrous sodium sulfate and concentrated under reduced pressure. The residue was purified by column chromatography (chloroform:methanol=100:2), to give compound 57 (67 mg, 85.2%).

$^1$H-NMR(CDCl$_3$-TMS) δ ppm: 0.97 (s,3H), 1.03 (s,3H), 1.13 (s,3H), 1.16 (d,3H,J=7.8 Hz), 1.30–2.60 (m,9H), 2.26 (d,1H,J=17.4 Hz), 2.99 (m,1H), 3.51 (d,1H,J=17.4 Hz), 4.40 (s,2H), 7.16 (br,1H), 7.49 (s,1H)

EXAMPLE 24 AND 25

(compound 60, 61)

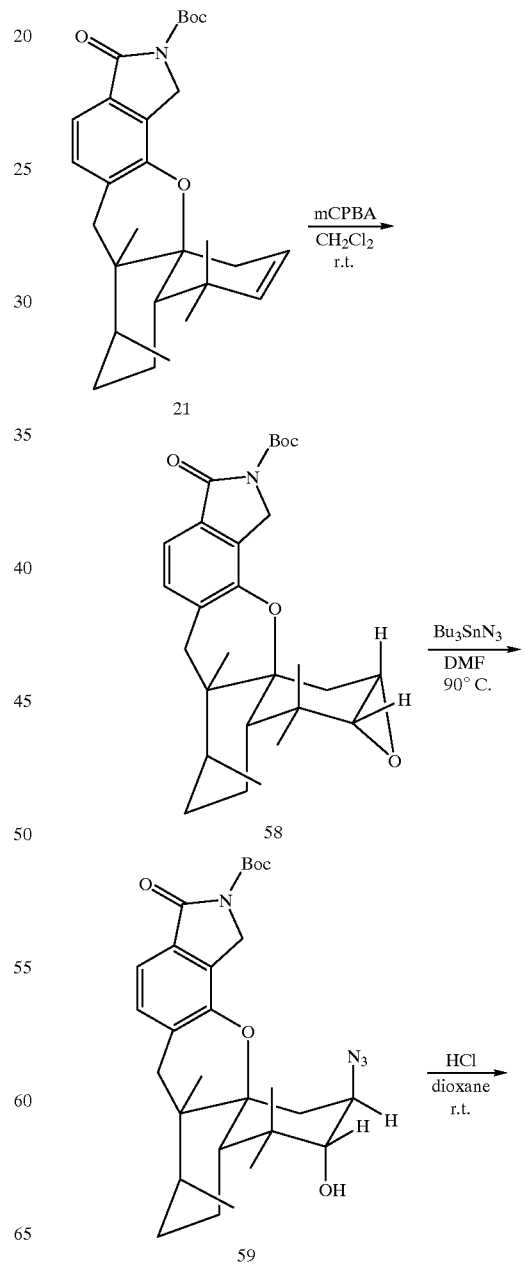

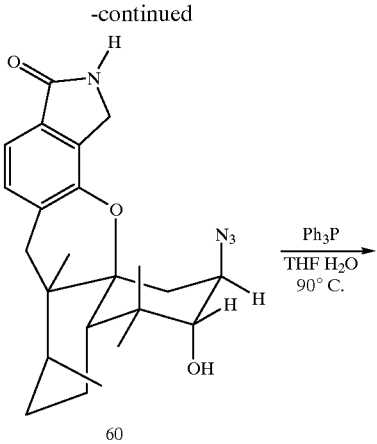

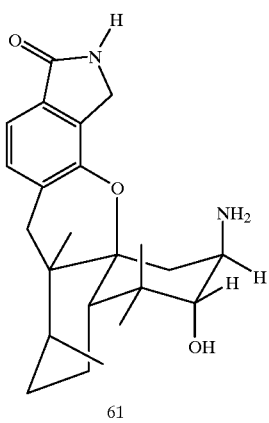

(1) To a solution of compound 21 (1000 mg) of Example 6 in Example 6 in dried methylene chloride (20 ml), was added m-chlorobenzoic acid (525 mg) under cooling, then the mixture stirred under nitrogen atmosphere at room temperature for 12 hours. To the reaction mixture, were added a solution of sodium thiosulfate and a solution of sodium bicarbonate, with stirring at room temperature for 1 hour. To the mixture was added water, then which was extracted with methylene chloride. The methylene chloride layer was dried over anhydrous sodium sulfate and concentrated under reduced pressure. The residue was purified by column chromatography (hexane:ethyl acetate=4:1), to give compound 58 (909 mg, 87.8 mg).

$^1$H-NMR(CDCl$_3$-TMS) δ ppm: 0.90 (s,3H), 1.03 (s,3H), 1.10 (s,3H), 1.13 (d,3H,J=7.5 Hz), 1.61 (s,9H), 1.35–2.28 (m,7H), 2.12 (d,1H,J=17.1 Hz), 2.46 (d,1H,J=15.6 Hz), 2.91 (d,1H,J=4.2 Hz), 3.40 (m,1H), 3.50 (d,1H,J=17.1 Hz), 4.63 (d,2H,J=4.8 Hz), 7.11 (d,1H,J=7.8 Hz), 7.34 (d,1H,J=7.5 Hz)

(2) To a solution of compound 58 (100 mg) in dried dimethyl formamide, was added tributyltinazide (500 mg) at room temperature, then which was stirred at 90° C. After 5 hours, water was added thereto, then which was extracted with ethyl acetate. The ethyl acetate layer was dried over anhydrous sodium sulfate and concentrated under reduced pressure. The residue was purified by column chromatography (hexane:ethyl acetate=4:1), to give compound 59 (90 mg, 82.6%).

$^1$H-NMR(CDCl$_3$-TMS) δ ppm: 0.92 (s,3H), 0.96 (s,3H), 1.10 (s,3H), 1.13 (d,3H,J=7.5 Hz), 1.61 (s,9H), 1.28–1.90 (m,7H), 2.05 (d,1H), 2.44 (d,1H,J=18.6 Hz), 2.56 (m,1H), 3.12 (d,1H,J=17.4 Hz), 3.71 (m,1H), 3.84 (m,1H), 4.66 (d,2H,J=16.2 Hz), 7.11 (d,1H,J=7.8 Hz), 7.36 (d,1H,J=7.5 Hz)

(3) The solution of Compound 59 (90 mg) in dioxane hydrochloride (2 ml) was stirred under nitrogen atmosphere at room temperature for 1 hour. The reaction mixture was concentrated under reduced pressure. The residue was purified by silica gel column chromatography (with ethyl acetate), to give compound 60 (50 mg, 69.1%).

$^1$H-NMR(CDCl$_3$-TMS) δ ppm: 0.90 (s,3H), 1.03 (s,3H), 1.10 (s,3H), 1.13 (d,3H,J=7.5 Hz), 1.61 (s,9H), 1.35–2.28 (m,7H), 2.12 (d,1H,J=17.1 Hz), 2.46 (d,1H,J=15.6 Hz), 2.91 (d,1H,J=4.2 Hz), 3.40 (m,1H), 3.50 (d,1H,J=17.1 Hz), 4.63 (d,2H,J=4.8 Hz), 7.11 (d,1H,J=7.8 Hz), 7.34 (d,1H=7.5 Hz)

$^1$H-NMR(CDCl$_3$-TMS) δ ppm: 0.92 (s,3H), 0.95 (s,3H), 1.02 (s,3H), 1.05 (d,3H,J=7.5 Hz), 1.22–2.00 (m,8H), 2.42 (d,1H,J=17.0 Hz), 2.54 (m,1H), 3.16 (d,1H,J=17.6 Hz), 3.72 (m,1H), 3.86 (m,1H), 4.36 (d,2H,J=6.6 Hz), 5.98 (br,1H), 7.12 (d,1H,J=7.8 Hz), 7.35 (d,1H,J=7.4 Hz)

(4) To a solution of compound 60 (40 mg) in tetrahydrofran (2 ml), were added water and triphenylphosphine (40 mg), and the mixture was stirred at 90° C. After 5 hours, the reaction mixture was concentrated under reduced pressure. The residue was purified by silica gel column chromatography (chloroform:methanol=10:1), to give compound 61 (20 mg, 53.3%).

$^1$H-NMR(CDCl$_3$-TMS) δ ppm: 0.95 (s,3H), 0.99 (s,3H), 1.10 (s,3H), 1.14 (d,3H,J=7.5 Hz), 1.20–2.50 (m,11H), 2.19 (d,1H,J=17.4 Hz), 3.40 (d,1H,J=17.7 Hz), 4.37 (s,2H), 6.16 (br,1H), 7.10 (d,1H,J=7.8 Hz), 7.36 (d,1H,J=7.8 Hz)

EXAMPLE 26

(compound 63)

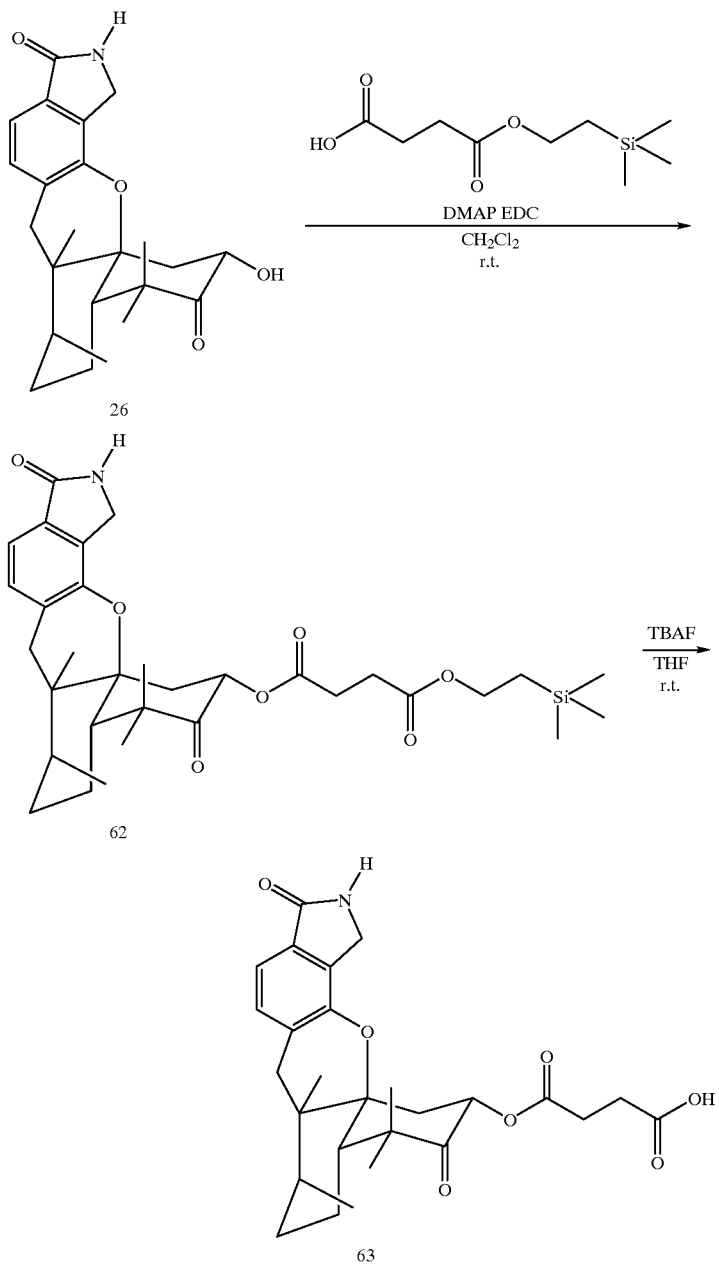

(1) To a solution of compound 26 (100 mg) in methylene chloride (20 ml), were added mono-trimethylsilyl succinic acid (114 mg), dimethylaminopyridine (4 mg), and EDC (56 mg). After 10 hours, the reaction mixture was concentrated under reduced pressure. The residue was purified by silica gel column chromatography (chloroform:methanol=100:3), to give compound 62 (100 mg, 65.8%).

(2) To a solution of compound 62 (100 mg) in dried tetrahydrofran, was added tetrabutylammonium fluoride (2 ml). After 10 hours, the reaction mixture was concentrated under reduced pressure. The residue was purified by silica gel column chromatography (chloroform:methanol=100:3), to give compound 63 (50 mg, 60.4%).

$^1$H-NMR(CDCl$_3$-TMS) δ ppm: 1.00 (s,3H), 1.04 (s,3H), 1.05 (s,3H), 1.14 (d,3H,J=6.9 Hz), 1.35–2.90 (m,7H), 2.25 (d,2H,J=17.4 Hz), 2.88 (m,2H), 3.30 (m,2H), 3.57 (m,1H), 4.49 (d,2H,J=6.3 Hz), 6.10 (m,1H), 7.19 (d,1H,J=7.8 Hz), 7.42 (d,1H,J=7.5 Hz), 7.62 (br,1H)

The other examples of the present compound are shown below.

(1) (1R*, 6a R, 7S, 9a S, 12 R*, 13a S)-12-chloro-2, 3, 6, 6a, 7, 8, 9, 9a, 10, 11, 12, 13-dodecahydro-1-methoxyphenyl-6a,7,10,10-tetramethyl-4-nitro-3,11-dioxo-1H-benzo[8,8a][1]benzopyrano[2,3-e]isoindole (2) (6-a R, 7S, 9a S, 11 R*, 12 R*, 13a S)-11-bromo-2, 3, 6, 6a, 7, 8, 9, 9a, 10, 11, 12, 13-dodecahydro-12-hydroxy- 6a,7,10,10-tetramethyl-3-oxo-1H-benzo[8,8a][1]
benzopyrano[2,3-e]isoindole (3) (6a R, 7S, 9a S, 12 R*, 13a S)-12-bromo-5-carboxy-2, 3, 6, 6a, 7, 8, 9, 9a, 10, 11, 12, 13-dodecahydro-6a,7,10,10-tetramethyl-3,11dioxo-1H-benzo[8,8a][1]benzopyrano[2,3-e]isoindole (4) (6a R, 7S, 9a S, 13a S)-4-bromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (5) (6a R, 7S, 9a S, 11 R*, 12 R*, 13a S)-12-acetylamino-5,11-dibromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (6) (6a R, 7S, 9a S, 11 R*, 12 R*, 13a S)-12-amino-11-bromo-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (7) (6a R, 7S, 9a S, 13a S)-2, 3, 6, 6a, 7, 8, 9, 9a, 10, 11, 12, 13dodecahydro4-methoxycarbonyl-6a,7,10,10-tetramethyl-3,11-dioxo-1H-benzo[8,8a][1]benzopyrano[2,3-e]isoindole (8) (1R*, 6a R, 7S, 9a S, 12 R*, 13a S)-12-acetylamino-2, 3, 6, 6a, 7, 8, 9, 9a, 10, 11, 12, 13-dodecahydro-1-hydroxy-6a,7,10,10-tetramethyl-4-nitro-3,11-dioxo-1H-benzo[8,8a][1]benzopyrano[2,3-e]isoindole (9) (6a R, 7S, 9a S, 11 R*, 12 R*, 13a S)-11-bromo-4, 12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(10) (6a R, 7S, 9a S, 11 R*, 12 R*, 13a S)-12-amino-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole

(11) (6a R, 7S, 9a S, 11 R*, 12 R*, 13a S)-12-bromo-5-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole

(12) (6a R, 7S, 9a S, 11 R*, 12 R*, 13a S)-12-acetylamino-5-bromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(13) (6a R, 7S, 9a S, 11 R*, 12 R*, 13a S)-11-chloro-2, 3, 6, 6a, 7, 8, 9, 9a, 10, 11, 12, 13-dodecahydro-4,12-dimethoxy-6a,7,10,10-tetramethyl-3-oxo-1H-benzo[8,8a][1]benzopyrano[2,3-e]isoindole

(14) (6a R, 7S, 9a S, 11 R*, 12 R*, 13a, 13a S)-4-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole

(15) (6a R, 7S, 9a, 11 R*, 12 R*, 13a S)-2, 3, 6, 6a, 7, 8, 9, 9a, 10, 11, 12, 13-dodecahydro-11-hydroxy-4-methoxycarbonyl-6a,7,10,10-tetramethyl-12-methylamino-3-oxo-1H-benzo[8,8a][1]benzopyrano[2,3-e]isoindole

(16) (6a R, 7S, 9a S, 11 R*, 12 R*, 13a S)-4-cyano-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole

(17) (6a R, 7S, 9a S, 11 R*, 12 R*, 13a S)-5,11,12-tribromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(18) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole

(19) (6a R, 7S, 9a S, 11 R*, 12 R*, 13a S)-12-bromo-11-chloro-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(20) (6a R, 7S, 9a S, 12 R*, 13a S)-5,12-dibromo-2, 3, 6, 6a, 7, 8, 9, 9a, 10, 11, 12, 13-dodecahydro-4,12-dimethoxy-6a,7,10,10-tetramethyl-3,11dioxo-1H-benzo[8,8a][1]benzopyrano[2,3-e]isoindole

(21) (6a R, 7S, 9a S, 13a S)-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole

(22) (6a R, 7S, 9a S, 11 R*, 12 R*, 13a S)-11,12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(23) (1R*, 6a R, 7S, 9a S, 12 R*, 13a S)-12-amino-5-chloro-2, 3, 6, 6a, 7, 8, 9, 9a, 10, 11, 12, 13-dodecahydro-1-methoxyphenyl-6a,7,10,10-tetramethyl-3,11dioxo-1H-benzo[8,8a][1]benzopyrano[2,3-e]isoindole

(24) (6a R, 7S, 9a S, 11 R*, 12 R*, 13a S)-11-bromo-2, 3, 6, 6a, 7, 8, 9, 9a, 10 11, 12, 13-dodecahydro-12-hydroxy-5-methoxycarbonyl-6a,7,10,10-tetramethyl-3-oxo-1H-benzo[8,8a][1]benzopyrano[2,3-e]isoindole

(25) (6a R, 7S, 9a S, 11 R*, 12 R*, 13a S)-5-carbamoyl-11-chloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole

(26) (1R*, 6a R, 7S, 9a S, 12 R*, 13a S)-12-acetylamino-2, 3, 6, 6a, 7, 8, 9, 9a, 10, 11, 12, 13-dodecahydro-1-methoxyphenyl-6a,7,10,10-tetramethyl-5-nitro-3,11-dioxo-1H-benzo[8,8a][1]benzopyrano[2,3-e]isoindole

(27) (1R*, 6a R, 7S, 9a S, 12 R*, 13a S)-12-bromo-5-chloro-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole

(28) (6a R, 7S, 9a S, 11 R*, 12 R*, 13a S)-4-bromo-11,12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(29) (6a R, 7S, 9a S, 12 R*, 13a S)-2, 3, 6, 6a, 7, 8, 9, 9a, 10, 11, 12, 13-dodecahydro-4,12-dihydroxy-6a,7,10,10-tetramethyl-3,11-dioxo-1H-benzo[8,8a][1]benzopyrano[2,3-e]isoindole

(30) (6a R, 7S, 9a S, 11 R*, 12 R*, 13a S)-4-carboxy-11-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole

(31) (6a R, 7S, 9a S, 13a S)-2, 3, 6, 6a, 7, 8, 9, 9a, 10, 11, 12, 13-dodecahydro-6a7,10,10-tetramethyl-3-oxo-1H-benzo[8,8a][1]benzopyrano[2,3-e]isoindole

(32) (6a R, 7S, 9a S, 12 R*, 13a S)-5-carbamoyl-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole

(33) (6a R, 7S, 9a S, 11 R*, 12 R*, 13a S)-12-amino-4-cyano-2, 3, 6, 6a, 7, , , 9a, 10, 11, 12, 13-dodecahydro-11-hydroxy-6a,7,10,10-tetramethyl-3-oxo-1H-benzo[8,8a][1]benzopyrano[2,3-e]isoindole

(34) (6a R, 7S, 9a S, 11 R*, 12 R*, 13a S)-11-chloro-2, 3, 6, 6a, 7, 8, 9, 9a, 10, 11, 12, 13-dodecahydro-12-methoxy-6a,7,10,10-tetramethyl-3-oxo-5-trifluoromethyl-1H-benzo[8,8a][1]benzopyrano[2,3-e]isoindole

(35) (6a R, 7S, 9a S, 11 R*, 12 R*, 13a S)-11-bromo-4-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole

(36) (6a R, 7S, 9a S, 11 R*, 12 R*, 13a S)-12-amino-2, 3, 6, 6a, 7, 8, 9, 9a, 10, 11, 12, 13-dodecahydro-11-hydroxy- 6a,7,10,10-tetramethyl-5-nitro-3-oxo-1H-benzo[8,8a][1]benzopyrano[2,3-e]isoindole

(37) (6a R, 7S, 9a S, 12 R*, 13a S)-4-chloro-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole

(38) (6a R, 7S, 9a S, 11 R*, 12 R*, 13a S)-11-chloro-2, 3, 6, 6a, 7, 8, 9, 9a, 10, 11, 12, 13-dodecahydro4-hydroxy-12-methoxy-6a,7,10,10-tetramethyl-3-oxo-1H-benzo[8,8a][1]benzopyrano[2,3-e]isoindole

(39) (6a R, 7S, 9a S, 11 R*, 12 R*, 13a S)-5,11-dibromo-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole

(40) (6a R, 7S, 9a S, 12 R*, 13a S)-12-amino-4-carbamoyl-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole

(41) (6a R, 7S, 9a S, 11 R*, 12 R*, 13a S)-12-chloro-2, 3, 6, 6a, 7, 8, 9, 9a, 10, 11, 12, 13-dodecahydro-11-hydroxy-6a,7,10,10-tetramethyl-3-oxo-4-trifluoromethyl-1H-benzo[8,8a][1]benzopyrano[2,3-e]isoindole

(42) (1R*, 6a R, 7S, 9a S, 13a S)-4-chloro-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole

(43) (1R*, 6a R, 7S, 9a S, 13 a S)-4-bromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole

(44) (1R*, 6a R, 7S, 9a S, 12 R*, 13a S)-5-bromo-2, 3, 6, 6a, 7, 8, 9, 9a, 10, 11, 12, 13-dodecahydro-1,12-dihydroxy-6a,7,10,10-tetramethyl-3,11-dioxo-1H-benzo[8,8a][1]benzopyrano[2,3-e]isoindole

(45) (6a R, 7S, 9a S, 13a S)-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole

(46) (1R*, 6a R, 7S, 9a S, 12 R*, 13a S)-5-bromo-2, 3, 6, 6a, 7, 8, 9, 9a, 10, 11, 12, 13-dodecahydro-1-hydroxyphenyl-12-methoxy-6a,7,10,10-tetramethyl-3,11-dioxo-1H-benzo[8,8a][1]benzopyrano[2,3-e]isoindole

(47) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole

(48) (6a R, 7S, 9a S, 11 R*, 11 R*, 12 R*, 13a S)-11-bromo-5-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole

(49) (6a R, 7S, 9a S, 11 R*, 12 R*, 13a S)-12-acetylamino-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole

(50) (6a R, 7S, 9a S, 11 R*, 12 R*, 13a S)-12-amino-2, 3, 6, 6a, 7, 8, 9, 9a, 10, 11, 12, 13-dodecahydro-4,11-dihydroxy-6a,7,10,10-tetramethyl-3-oxo-1H-benzo[8,8a][1]benzopyrano[2,3-e]isoindole

(51) (1R*, 6a R, 7S, 9a S, 12 R*, 13a S)-2, 3, 6, 6a, 7, 8, 9, 9a, 10, 11, 12, 13-dodecahydro-1-hydroxy-6a,7,10,10-tetramethyl-12-methylamino-3,11-dioxo-1H-benzo[8,8a][1]benzopyrano[2,3-e]isoindole

(52) (1R*, 6a R, 7S, 9a S, 12 R*, 13a S)-4,12-dichloro-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole

(53) (1R*, 6a R, 7S, 9a S, 12R*, 13a S)-12-acetylamino-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole

(54) (6a R, 7S, 9a S, 11 R*, 12 R*, 13a S)-11-chloro-5-cyano-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole

(55) (1R*, 6a R, 7S, 9a S, 12 R*, 13a S)-5-bromo-12-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole

(56) (1R*, 6a R, 7S, 9a S, 12 R*, 13a S)-5-bromo-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(57) (6a R, 7S, 9a S, 11 R*, 12 R*, 13a S)-12-acetylamino-11-bromo-4-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(58) (6a R, 7S, 9a S, 11 R*, 12 R*, 13a S)-12-amino-4-carbamoyl-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole

(59) (6a R, 7S, 9a S, 11 R*, 12 R*, 13a S)-12-amino-5-cyano-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole

(60) (6a R, 7S, 9a S, 11 R*, 12 R*, 13a S)-5,12-dibromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole

(61) (6a R, 7S, 9a S, 11 R*, 12 R*, 13a S)-2, 3, 6, 6a, 7, 8, 9, 9a, 10, 11, 12, 13-dodecahydro-12-hydroxy-4-methoxy-6a,7,10,10-tetramethyl-3-oxo-1H-benzo[8,8a][1]benzopyrano[2,3-e]isoindole

(62) (6a R, 7S, 9a S, 11 R*, 12 R*, 13a S)-4-carbamoyl-11-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole

(63) (6a R, 7S, 9a S, 11 R*, 12 R*, 13a S)-11-chloro-4-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(64) (1R*, 6a R, 7S, 9a S, 12 R*, 13a S)-12-amino-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole

(65) (1R*, 6a R, 7S, 9a S, 12 R*, 13a S)-12-amino-4-bromo-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole

(66) (1R*, 6a R, 7S, 9a S, 12 R*, 13a S)-12-chloro-2, 3, 6, 6a, 7, 8, 9, 9a, 10, 11, 12, 13-dodecahydro-1-methoxy-6a,7,10,10-tetramethyl-4-nitro-3,11-dioxo-1H-benzo[8,8a][1]benzopyrano[2,3-e]isoindole

(67) (6a R, 7S, 9a S, 11 R*, 12 R*, 13a S)-11-bromo-4-cyano-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole

(68) (6a R, 7S, 9a S, 11 R*, 12 R*, 13a S)-12-amino-11-bromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(69) (6a R, 7S, 9a S, 11 R*, 12 R*, 13a S)-2, 3, 6, 6a, 7, 8, 9, 9a, 10, 11, 12, 13-dodecahydro-6a,7,10,10-tetramethyl-12-methylamino-4-nitro-3-oxo-1H-benzo[8,8a][1]benzopyrano[2,3-e]isoindole

(70) (6a R, 7S, 9a S, 11 R*, 12 R*, 13a S)-5-bromo-2, 3, 6, 6a, 7, 8, 9, 9a, 10, 11, 12, 13-dodecahydro-11,12-dihydroxy-6a,7,10,10-tetramethyl-3-oxo-1H-benzo[8,8a][1]benzopyrano[2,3-e]isoindole

(71) (6a R, 7S, 9a S, 11 R*, 12 R*, 13a S)-5-carbamoyl-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(72) (6a R, 7S, 9a S, 11 R*, 12 R*, 13a S)-11-bromo-5-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(73) (6a R, 7S, 9a S, 11 R*, 12 R*, 13a S)-11-bromo-5-carbamoyl-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole

(74) (6a R, 7S, 9a S, 11 R*, 12 R*, 13a S)-2, 3, 6, 6a, 7, 8, 9, 9a, 10, 11, 12, 13-dodecahydro-11-hydroxy-6a,7,10,10-tetramethyl-3-oxo-5-trifluoromethyl-1H-benzo[8,8a][1]benzopyrano[2,3-e]isoindole

(75) (1R*, 6a R, 7S, 9a S, 12 R*, 13a S)-12-acetylamino-2, 3, 6, 6a, 7, 8, 9, 9a, 10, 11, 12, 13-dodecahydro-1-hydroxyphenyl-6a,7,10,10-tetramethyl-5-nitro-3,11-dioxo-1H-benzo[8,8a][1]benzopyrano[2,3-e]isoindole

(76) (6a R, 7S, 9a S, 11 R*, 12 R*, 13a S)-12-acetylamino-4-carboxy-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole

(77) (1R*, 6a R, 7S, 9a S, 12 R*, 13a S)-12-bromo-5-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole

(78) (1R*, 6a R, 7S, 9a S, 12 R*, 13a S)-12-chloro-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(79) (6a R, 7S, 9a S, 12 R*, 13a S)-4-bromo-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole

(70) (6a R, 7S, 9a S, 11 R*, 12 R*, 13a S)-12-amino-4-carboxy-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(71) (6a R, 7S, 9a S, 11 R*, 12 R*, 13a S)-12-amino-4-bromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(72) (6a R, 7S, 9a S, 11 R*, 12 R*, 13a S)-2, 3, 6, 6a, 7, 8, 9, 9a, 10, 11, 12, 13-dodecahydro-6a,7,10,10-tetramethyl-12-methylamino-3-oxo-5-trifluoromethyl-1H-benzo[8,8a][1]benzopyrano[2,3-e]isoindole

(73) (6a R, 7S, 9a S, 11 R*, 12 R*, 13a S)-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole

(74) (1R*, 6a R, 7S, 9a S, 12 R*, 13a S)-5,12-dibromo-2, 3, 6, 6a, 7, 8, 9, 9a, 10, 11, 12, 13-dodecahydro-1,12-dimethoxy-6a,7,10,10-tetramethyl-3,11-dioxo-1H-benzo[8,8a][1]benzopyrano[2,3-e]isoindole

(75) (1R*, 6a R, 7S, 9a S, 12 R*, 13a S)-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(76) (1R*, 6a R, 7S, 9a S, 12 R*, 13a S)-12-bromo-4-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(77) (1R*, 6a R, 7S, 9a S, 12 R*, 13a S)-12-amino-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole

(78) (6a R, 7S, 9a S, 12 R*, 13a S)-5-bromo-2, 3, 6, 6a, 7, 8, 9, 9a, 10, 11, 12, 13-dodecahydro-12-hydroxy-6a,7,10,10-tetramethyl-3,11-dioxo-1H-benzo[8,8a][1]benzopyrano[2,3-e]isoindole

(79) (6a R, 7S, 9a S, 11 R*, 12 R*, 13a S)-11-chloro-4-cyano-2, 3, 6, 6a, 7, 8, 9, 9a, 10, 11, 12, 13-dodecahydro-6a,7,10,10=tetramethyl-12-methylamino-3-oxo-1H-benzo[8,8a][1]benzopyrano[2,3-e]isoindole

(90) (6a R, 7S, 9a S, 11 R*, 12 R*, 13a S)-11-chloro-2, 3, 6, 6a, 7, 8, 9, 9a, 10, 11, 12, 13-dodecahydro-12-hydroxy-4-methoxy-6a,7,10,10-tetramethyl-3-oxo-1H-benzo[8,8a][1]benzopyrano[2,3-e]isoindole

(91) (6a R, 7S, 9a S, 11 R*, 12 R*, 13a S)-11-chloro-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole

(92) (6a R, 7S, 9a S, 11 R*, 12 R*, 13a S)-11-chloro-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(93) (1R*, 6a R, 7S, 9a S, 12 R*, 13a S)-12-amino-2, 3, 6, 6a, 7, 8, 9, 9a, 10, 11, 12, 13-dodecahydro-1-hydroxy-6a,7,10,10-tetramethyl-4-nitro-3,11-dioxo-1H-benzo[8,8a][1]benzopyrano[2,3-e]isoindole

(94) (6a R, 7S, 9a S, 12 R*, 13a S)-4-carbamoyl-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole

(95) (6a R, 7S, 9a S, 12 R*, 13a S)-12-amino-4-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(96) (1R*, 6a R, 7S, 9a S, 12 R*, 13a S)-2, 3, 6, 6a, 7, 8, 9, 9a, 10, 11, 12, 13-dodecahydro-1-methoxyphenyl-6a,7,10,10-tetramethyl-12-methylamino-5-nitro-3,11-dioxo-1H-benzo[8,8a][1]benzopyrano[2,3-e]isoindole

(97) (6a R, 7S, 9a S, 11 R*, 12 R*, 13a S)-4-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole

(98) (6a R, 7S, 9a S, 11 R*, 12 R*, 13a S)-12-acetylamino-2, 3, 6, 6a, 7, 8, 9, 9a, 10, 11, 12, 13-dodecahydro-11-hydroxy-6a,7,10,10-tetramethyl-3-oxo-5-trifluoromethyl-1H-benzo[8,8a][1]benzopyrano[2,3-e]isoindole

(99) (6a R, 7S, 9a S, 11 R*, 12 R*, 13a S)-12-acetylamino-11-bromo-4-chloro-2, 3, 6, 6a, 7, 8, 9, 9a, 10, 11, 12, 13-dodecahydro-6a,7,10,10-tetramethyl-3oxo-1H-benzo[8,8a][1]benzopyrano[2,3-e]isoindole (100) (6a R, 7S, 9a S, 13a S)-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (101) (6a R, 7S, 9a S, 11 R*, 12 R*, 13a S)-12-bromo-4-carboxy-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (102) (1R*, 6a R, 7S, 9a S, 13a S)-5-chloro-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (103) (1R*, 6a R, 7S, 9a S, 13a S)-4-bromo-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (104) (1R*, 6a R, 7S, 9a S, 12 R*, 13a S)-5-chloro-2, 3, 6, 6a, 7, 8, 9, 9a, 10, 11, 12, 13-dodecahydro-1-methoxy-6a,7,10,10-tetramethyl-12-methylamino-3,11-dioxo-1H-benzo[8,8a][1]benzopyrano[2,3-e]isoindole (105) (6a R, 7S, 9a S, 13a S)-5-chloro-2, 3, 6, 6a, 7, 8, 9, 9a, 10, 13-decahydro-6a,7,10,10-tetramethyl-3-oxo-1H-benzo[8,8a][1]benzopyrano[2,3-e]isoindole (106) (6a R, 7S, 9a S, 11 R*, 12 R*, 13a S)-5,11-dichloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (107) (6a R, 7S, 9a S, 11 R*, 12 R*, 13a S)-2, 3, 6, 6a, 7, 8, 9, 9a, 10, 11, 12, 13-dodecahydro-12-methoxy-4-methoxycarbonyl-6a,7,10,10-tetramethyl-3-oxo-1H-benzo[8,8a][1]benzopyrano[2,3-e]isoindole (108) (1R*, 6a R, 7S, 9a S, 12 R*, 13a S)-12-amino-2, 3, 6, 6a, 7, 8, 9, 9a, 10, 11, 12, 13-dodecahydro-1-methoxyphenyl-6a,7,10,10-tetramethyl-5-nitro-3,11-dioxo-1H-benzo[8,8a][1]benzopyrano[2,3-e]isoindole (109) (6a R, 7S, 9a S, 11 R*, 12 R*, 13a S)-12-acetylamino-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (110) (6a R, 7S, 9a S, 11 R*, 12 R*, 13a S)-11-chloro-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (111) (6a R, 7S, 9a S, 12 R*, 13a S)-2, 3, 6, 6a, 7, 8, 9, 9a, 10, 11, 12, 13-dodecahydro-12-methoxy-4-methoxycarbonyl-6a,7,10,10-tetramethyl-3,11-dioxo-1H-benzo[8,8a][1]benzopyrano[2,3-e]isoindole (112) (6a R, 7S, 9a S, 12 R*, 13a S)-11-bromo-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (113) (6a R, 7S, 9a S, 12 R*, 13a S)-5-chloro-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole (114) (6a R, 7S, 9a S, 12 R*, 13a S)-5-bromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (115) (6a R, 7S, 9a S, 12 R*, 13a S)-2, 3, 6, 6a, 7, 8, 9, 9a, 10, 11, 12, 13-dodecahydro-12-methoxy-6a,7,10,10-tetramethyl-4-nitro-3-oxo-1H-benzo[8,8a][1]benzopyrano[2,3-e]isoindole (116) (6a R, 7S, 9a S, 11 R*, 12 R*, 13a S)-4-bromo-2, 3, 6, 6a, 7, 8, 9, 9a, 10, 11, 12, 13-dodecahydro-11,12-dihydroxy-6a,7,10,10-tetramethyl-3-oxo-1H-benzo[8,8a][1]benzopyrano[2,3-e]isoindole (117) (6a R, 7S, 9a S, 11 R*, 12 R*, 13a S)-11-bromo-2, 3, 6, 6a, 7, 8, 9, 9a, 10, 11, 12, 13-dodecahydro-12-hydroxy-6a,7,10,10-tetramethyl-5-nitro-3-oxo-1H-benzo[8,8a][1]benzopyrano[2,3-e]isoindole (118) (1R*, 6a R, 7S, 9a S, 12 R*, 13a S)-12-bromo-2, 3, 6, 6a, 7, 8, 9, 9a, 10, 11, 12, 13-dodecahydro-1-hydroxy-6a,7,10,10-tetramethyl-4-nitro-3,11-dioxo-1H-benzo[8,8a][1]benzopyrano[2,3-e]isoindole (119) (6a R, 7S, 9a S, 11 R*, 12 R*, 13a S)-12-acetylamino-11-chloro-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole (120) (6a R, 7S, 9a S, 11 R*, 12 R*, 13a S)-4-bromo-2, 3, 6, 6a, 7, 8, 9, 9a, 10, 11, 12, 13-dodecahydro-11-hydroxy-6a,7,10,10-tetramethyl-12-methoxy-3-oxo-1H-benzo[8,8a][1]benzopyrano[2,3-e]isoindole (121) (6a R, 7S, 9a S, 11 R*, 12 R*, 13a S)-5-carbamoyl-12-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (122) (6a R, 7S, 9a S, 11 R*, 12 R*, 13a S)-4-bromo-2, 3, 6, 6a, 7, 8, 9, 9a, 10, 11, 12, 13-dodecahydro-11-hydroxy-12-methoxy-6a,7,10,10-tetramethyl-3-oxo-1H-benzo[8,8a][1]benzopyrano[2,3-e]isoindole (123) (6a R, 7S, 9a S, 13a S)-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (124) (1R*, 6a R, 7S, 9a S, 12 R*, 13a S)-12-amino-5-chloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (125) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (126) (6a R, 7S, 9a S, 12 R*, 13a S)-4-bromo-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole (127) (6a R, 7S, 9a S, 11 R*, 12 R*, 13a S)-12-bromo-11-chloro-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (128) (6a R, 7S, 9a S, 11 R*, 12 R*, 13a S)-2, 3, 6, 6a, 7, 8, 9, 9a, 10, 11, 12, 13-dodecahydro-11-hydroxy-12-methoxy-6a,7,10,10-tetramethyl-4-nitro-3-oxo-1H-benzo[8,8a][1]benzopyrano[2,3-e]isoindole (129) (6a R, 7S, 9a S, 11 R*, 12 R*, 13a S)-11-chloro-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (130) (6a R, 7S, 9a S, 12 R*, 13a S)-12-acetylamino-4-cyano-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (131) (6a R, 7S, 9a S, 11 R*, 12 R*, 13a S)-11-bromo-2, 3, 6, 6a, 7, 8, 9, 9a, 10, 11, 12, 13-dodecahydro-12-hydroxy-4-methoxy-6a,7,10,10-tetramethyl-3-oxo-1H-benzo[8,8a][1]benzopyrano[2,3-e]isoindole (132) (6a R, 7S, 9a S, 11 R*, 12 R*, 13a S)-5,12-dichloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (133) (6a R, 7S, 9a S, 11 R*, 12 R*, 13a S)-5-carbamoyl-2, 3, 6, 6a, 7, 8, 9, 9a, 10, 11, 12, 13-dodecahydro-11,12-dihydroxy-6a,7,10,10-tetramethyl-3-oxo-1H-benzo[8,8a][1]benzopyrano[2,3-e]isoindole (134) (6a R, 7S, 9a S, 11 R*, 12 R*, 13a S)-2, 3, 6, 6a, 7, 8, 9, 9a, 10, 11, 12, 13-dodecahydro-11-hydroxy-12-methoxy-6a,7,10,10-tetramethyl-3-oxo-5-trifluoromethyl-1H-benzo[8,8a][1]benzopyrano[2,3-e]isoindole (135) (6a R, 7S, 9a S, 11 R*, 12 R*, 13a S)-2, 3, 6, 6a, 7, 8, 9, 9a, 10, 11, 12, 13-dodecahydro-12-hydroxy-4-methoxycarbonyl-6a,7,10,10-tetramethyl-3-oxo-1H-benzo[8,8a][1]benzopyrano[2,3-e]isoindole (136) (6a R, 7S, 9a S, 11 R*, 12 R*, 13a S)-11-bromo-5,12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (137) (6a R, 7S, 9a S, 11 R*, 12 R*, 13a S)-12-acetylamino-11-bromo-5-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (138) (1R*, 6a R, 7S, 9a S, 12 R*, 13a S)-12-amino-2, 3, 6, 6a, 7, 8, 9, 9a, 10, 11, 12, 13-dodecahydro-1-methoxy-6a,7,10,10-tetramethyl-5-nitro-3,11-dioxo-1H-benzo[8,8a][1]benzopyrano[2,3-e]isoindole (139) (6a R, 7S, 9a S, 11 R*, 12 R*, 13a S)-4,11,12-tribromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (140) (6a R, 7S, 9a S, 11 R*, 12 R*, 13a S)-2, 3, 6, 6a, 7, 8, 9, 9a, 10, 11, 12, 13-dodecahydro-12-hydroxy-6a,7,10,10-tetramethyl-3-oxo-5-trifluoromethyl-1H-benzo[8,8a][1]benzopyrano[2,3-e]isoindole (141) (6a R, 7S, 9a S, 11 R*, 12 R*, 13a S)-12-acetylamino-11-chloro-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (142) (6a R, 7S, 9a S, 11 R*, 12 R*, 13a S)-12-bromo-11-chloro-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (143) (6a R, 7S, 9a S, 11 R*, 12 R*, 13a S)-5-carbamoyl-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3-e]isoindole (144) (1R*, 6a R, 7S, 9a S, 12 R*, 13a S)-12-acetylamino-2, 3, 6, 6a, 7, 8, 9, 9a, 10, 11, 12, 13-dodecahydro-1-methoxy-6a,7,10,10-tetramethyl-4-nitro-3,11-dioxo-1H-benzo[8,8a][1]benzopyrano[2,3-e]isoindole (145) (1R*, 6a R, 7S, 9a S, 12 R*, 13a S)-12-chloro-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (146) (1R*, 6a R, 7s, 9a S, 12 R*, 13a S)-12-bromo-2, 3, 6, 6a, 7, 8, 9, 9a, 10, 11, 12, 13-dodecahydro-1-hydroxyphenyl-6a,7,10,10-tetramethyl-5-nitro-3,11-dioxo-1H-benzo[8,8a][1]benzopyrano[2,3-e]isoindole (147) (6a R, 7S, 9a S, 11 R*, 12 R*, 13a S)-12-bromo-2, 3, 6, 6a, 7, 8, 9, 9a, 10, 11, 12, 13-dodecahydro- 11-hydroxy-6a,7,10,10-tetramethyl-3-oxo-4-trifluoromethyl-1H-benzo[8,8a][1]benzopyrano[2,3-e]isoindole (148) (6a R, 7S, 9a S, 11 R*, 12 R*, 13a S)-11-bromo-2, 3, 6, 6a, 7, 8, 9, 9a, 10, 11, 12, 13-dodecahydro-4-hydroxy-12-methoxy-6a,7,10,10-tetramethyl-3-oxo-1H-benzo[8,8a][1]benzopyrano[2,3-e]isoindole (149) (6a R, 7S, 9a S, 11 R*, 12 R*, 13a S)-12-acetylamino-4,11-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (150) (6a R, 7S, 9a S, 11 R*, 12 R*, 13a S)-12-amino-2, 3, 6, 6a, 7, 8, 9, 9a, 10, 11, 12, 13-dodecahydro-11-hydroxy-6a,7,10,10-tetramethyl-3-oxo-4-trifluoromethyl-1H-benzo[8,8a][1]benzopyrano[2,3-e]isoindole (151) (6a R, 7S, 9a S, 12 R*, 13a S)-2, 3, 6, 6a, 7, 8, 9, 9a, 10, 11, 12, 13-dodecahydro-12-methoxy-6a,7,10,10-tetramethyl-3,11-dioxo-5-trifluoromethyl-1H-benzo[8,8a][1]benzopyrano[2,3-e]isoindole (152) (6a R, 7S, 9a S, 12 R*, 13a S)-5-bromo-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (153) (6a R, 7S, 9a S, 11 R*, 12 R*, 13a S)-5,11-dibromo-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (154) (6a R, 7S, 9a S, 12 R*, 13a S)-2, 3, 6, 6a, 7, 8, 9, 9a, 10, 11, 12, 13-dodecahydro-6a,7,10,10-tetramethyl-12-methylamino-4-nitro-3,11-dioxo-1H-benzo[8,8a][1]benzopyrano[2,3-e]isoindole (155) (6a R, 7S, 9a S, 11 R*, 12 R*, 13a S)-12-amino-5-carbamoyl-2, 3, 6, 6a, 7, 8, 9, 9a, 10, 11, 12, 13-dodecahydro-11-11-hydroxy-6a,7,10,10-tetramethyl-3-oxo-1H-benzo[8,8a][1]benzopyrano[2,3-e]isoindole (156) (6a R, 7S, 9a S, 11 R*, 12 R*, 13a S)-12-amino-11-chloro-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (157) (6a R, 7S, 9a S, 12 R*, 13a S)-12-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (158) (1R*, 6a R, 7S, 9a S, 13a S)-2, 3, 6, 6a, 7, 8, 9, 9a, 10, 11, 12, 13-dodecahydro-1-methoxy- 6a,7,10,10-tetramethyl-3,11-dioxo-1H-benzo[8,8a][1]benzopyrano[2,3-e]isoindole (159) (6a R, 7S, 9a S, 11 R*, 12 R*, 13a S)-11-bromo-2, 3, 6, 6a, 7, 8, 9, 9a, 10, 11, 12, 13-dodecahydro-4,12-dimethoxy-6a,7,10,10-tetramethyl-3-oxo-1H-benzo[8,8a][1]benzopyrano[2,3-e]isoindole (160) (1R*, 6a R, 7S, 9a S, 12 R*, 13a S)-6-chloro-2, 3, 6, 6a, 7, 8, 9, 9a, 10, 11, 12, 13-dodecahydro-1-methoxyphenyl-6a,7,10,10-tetramethyl-12-methylamino-3,11-dioxo-1H-benzo[8,8a][1]benzopyrano[2,3-e]isoindole (161) (1R*, 6a R, 7S, 9a S, 12 R*, 13a S)-11-bromo-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole (162) (1R*, 6a R, 7S, 9a S, 12 R*, 13a S)-12-acetylamino-4-bromo-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (163) (1R*, 6a R, 7S, 9a S, 12 R*, 13a S)-2, 3, 6, 6a, 7, 8, 9, 9a, 10, 11, 12, 13-dodecahydro-1,12-dimethoxy-6a,7,10,10-tetramethyl-5,12-dibromo-3,11-dioxo-1H-benzo[8,8a][1]benzopyrano[2,3-e]isoindole (164) (6a R, 7S, 9a S, 11 R*, 12 R*, 13a S)-4-bromo-11,12-エポキシ-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (165) (6a R, 7S, 9a S, 13a S)-5-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (166) (6a R, 7S, 9a S, 11 R*, 12 R*, 13a S)-12-chloro-2, 3, 6, 6a, 7, 8, 9, 9a, 10, 11, 12, 13-dodecahydro-11-hydroxy-6a,7,10,10-tetramethyl-3-oxo-5-trifluoromethyl-1H-benzo[8,8a][1]benzopyrano[2,3-e]isoindole (167) (6a R, 7S, 9a S, 12 R*, 13a S)-2, 3, 6, 6a, 7, 8, 9, 9a, 10, 11, 12, 13-dodecahydro-12-hydroxy-4-methoxycarbonyl-6a,7,10,10-tetramethyl-3,11-dioxo-1H-benzo[8,8a][1]benzopyrano[2,3-e]isoindole (168) (6a R, 7S, 9a S, 12 R*, 13a S)-2, 3, 6, 6a, 7, 8, 9, 9a, 10, 11, 12, 13-dodecahydro-12-hydroxy-6a,7,10,10-tetramethyl-5-nitro-3,11-dioxo-1H-benzo[8,8a][1]benzopyrano[2,3-e]isoindole (169) (6a R, 7S, 9a S, 11 R*, 12 R*, 13a S)-4-carbamoyl-11-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (170) (6a R, 7S, 9a S, 12 R*, 13a S)-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole (171) (6a R, 7S, 9a S, 12 R*, 13a S)-2, 3, 6, 6a, 7, 8, 9, 9a, 10, 11, 12, 13-dodecahydro-12-methoxy-5-

(172) (6a R, 7S, 9a S, 11 R*, 12 R*, 13a S)-12-bromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (173) (6a R, 7S, 9a S, 11 R*, 12 R*, 13a S)-12-amino-11-chloro-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole (174) (1R*, 6a R, 7S, 9a S, 12 R*, 13a S)-12-bromo-2, 3, 6, 6a, 7, 8, 9, 9a, 10, 11, 12, 13-dodecahydro-1-methoxy-6a,7,10,10-tetramethyl-5-nitro-3,11-dioxo-1H-benzo[8,8a][1]benzopyrano[2,3-e]isoindole (175) (6a R, 7S, 9a S, 11 R*, 12 R*, 13a S)-12-amino-11-bromo-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (176) (6a R, 7S, 9a S, 11 R*, 12 R*, 13a S)-12-bromo-11-chloro-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (177) (6a R, 7S, 9a S, 12 R*, 13a S)-12-amino-5-cyano-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (178) (6a R, 7S, 9a S, 11 R*, 12 R*, 13a S)-4-cyano-2, 3, 6, 6a, 7, 8, 9, 9a, 10, 11, 12, 13-dodecahydro-11-hydroxy-12-methoxy-6a,7,10,10-tetramethyl-3-oxo-1H-benzo[8,8a][1]benzopyrano[2,3-e]isoindole (179) (1R*, 6a R, 7S, 9a S, 12 R*, 13a S)-12-amino-5-bromo-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (180) (6a R, 7S, 9a S, 11 R*, 12 R*, 13a S)-11-bromo-12-chloro-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (181) (1R*, 6a R, 7S, 9a S, 12 R*, 13a S)-5,12-dichloro-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (182) (1R*, 6a R, 7S, 9a S, 12 R*, 13a S)-12-bromo-5-chloro-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (183) (1R*, 6a R, 7S, 9a S, 12 R*, 13a S)-12-acetylamino-5-bromo-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (184) (6a R, 7S, 9a S, 11 R*, 12 R*, 13a S)-11-bromo-4-carbamoyl-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (185) (1R*, 6a R, 7S, 9a S, 12 R*, 13a S)-12-chloro-2, 3, 6, 6a, 7, 8, 9, 9a, 10, 11, 12, 13-dodecahydro-1-methoxyphenyl-6a,7,10,10-tetramethyl-5-nitro-3,11-dioxo-1H-benzo[8,8a][1]benzopyrano[2,3-e]isoindole (186) (6a R, 7S, 9a S, 12 R*, 13a S)-12-acetylamino-5-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (187) (6a R, 7S, 9a S, 12 R*, 13a S)-5-cyano-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (188) (6a R, 7S, 9a S, 11 R*, 12 R*, 13a S)-11-bromo-2, 3, 6, 6a, 7, 8, 9, 9a, 10, 11, 12, 13-dodecahydro-12-methoxy-6a,7,10,10-tetramethyl-5-nitro-3-oxo-1H-benzo[8,8a][1]benzopyrano[2,3-e]isoindole (189) (6a R, 7S, 9a S, 11 R*, 12 R*, 13a S)-2, 3, 6, a, 7, 8, 9, 9a, 10, 11, 12, 13-dodecahydro-4,12-dimethoxy-6a,7,10,10-tetramethyl-3-oxo-1H-benzo[8,8a][1]benzopyrano[2,3-e]isoindole (190) (6a R, 7S, 9a S, 11 R*, 12 R*, 13a S)-4-carboxy-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (191) (6a R, 7S, 9a S, 11 R*, 12 R*, 13a S)-12-acetylamino-11-bromo-5-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (192) (6a R, 7S, 9a S, 11 R*, 12 R*, 13a S)-12-chloro-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (193) (6a R, 7S, 9a S, 12 R*, 13a S)-5-carbamoyl-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (194) (1R*, 6a R, 7S, 9a S, 12 R*, 13a S)-2, 3, 6, 6a, 7, 8, 9, 9a, 10, 11, 12, 13-dodecahydro-1-hydroxy-12-methoxy-6a,7,10,10-tetramethyl-5-nitro-3,11-dioxo-1H-benzo[8,8a][1]benzopyrano[2,3-e]isoindole (195) (6a R, 7S, 9a S, 11 R*, 12 R*, 13a S)-11-chloro-2, 3, 6, 6a, 7, 8, 9, 9a, 10, 11, 12, 13-dodecahydro-12-methoxy-6a,7,10,10-tetramethyl-3-oxo-4-trifluoromethyl-1H-benzo[8,8a][1]benzopyrano[2,3-e]isoindole (196) (1R*, 6a R, 7S, 9a S, 12 R*, 13a S)-2, 3, 6, 6a, 7, 8, 9, 9a, 10, 11, 12, 13-dodecahydro-1-methoxy-6a,7,10,10-tetramethyl-12-methylamino-4-nitro-3,11-dioxo-1H-benzo[8,8]a[1]benzopyrano[2,3-e]isoindole (197) (6a R, 7S, 9a S, 11 R*, 12 R*, 13a S)-5,12-dibromo-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (198) (1R*, 6a R, 7S, 9a S, 12 R*, 13a S)-2, 3, 6, 6a, 7, 8, 9, 9a, 10, 11, 12, 13-dodecahydro-1-hydroxy-6a,7,10,10-tetramethyl-12-methylamino-4-nitro-3,11-dioxo-1H-benzo[8,8a][1]benzopyrano[2,3-e]isoindole (199) (6a R, 7S, 9a S, 11 R*, 12 R*, 13a S)-12-amino-11-bromo-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (200) (6a R, 7S, 9a S, 11 R*, 12 R*, 13a S)-12-amino-11-bromo-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (201) (6a R, 7S, 9a S, 11 R*, 12 R*, 13a S)-11-chloro-2, 3, 6, 6a, 7, 8, 9, 9a, 10, 11, 12, 13-dodecahydro-6a,7,10,10-tetramethyl-12-methylamino-5-nitro-3-oxo-1H-benzo[8,8a][1]benzopyrano[2,3-e]isoindole (202) (6a R, 7S, 9a S, 12 R*, 13a S)-12-bromo-2, 3, 6, 6a, 7, 8, 9, 9a, 10, 11, 12, 13-dodecahydro-6a,7,10,10-tetramethyl-5-nitro-3,11-dioxo-1H-benzo[8,8a][1]benzopyrano[2,3-e]isoindole (203) (1R*, 6a R, 7S, 9a S, 12 R*, 13a S)-5-bromo-2, 3, 6, 6a, 7, 8, 9, 9a, 10, 11, 12, 13-dodecahydro-12-methoxy-1-methoxyphenyl-6a,7,10,10-tetramethyl-3,11-dioxo-1H-benzo[8,8a][1]benzopyrano[2,3-e]isoindole (204) (1R*, 6a R, 7S, 9a S, 12 R*, 13a S)-4-chloro-2, 3, 6, 6a, 7, 8, 9, 9a, 10, 11, 12, 13-dodecahydro-1,12-dihydroxy-6a,7,10,10-tetramethyl-3,11-dioxo-1H-benzo[8,8a][1]benzopyrano[2,3-e]isoindole (205) (6a R, 7S, 9a S, 11 R*, 12 R*, 13a S)-2, 3, 6, 6a, 7, 8, 9, 9a, 10, 11, 12, 13-dodecahydro-6a,7,10,10-

(206) (6a R, 7S, 9a S, 11 R*, 13a S)-2, 3, 6, 6a, 7, 8, 9, 9a, 10, 11, 12, 13-dodecahydro-11,12-dihydroxy-4-methoxycarbonyl-6a,7,10,10-tetramethyl-3-oxo-1H-benzo[8,8a][1]benzopyrano[2,3-e]isoindole (207) (6a R, 7S, 9a S, 11 R*, 12 R*, 13a S)-2, 3, 6, 6a, 7, 8, 9, 9a, 10, 11, 12, 13-dodecahydro-4,11-dihydroxy-6a,7,10,10-tetramethyl-12-methylamino-3-oxo-1H-benzo[8,8a][1]benzopyrano[2,3-e]isoindole (208) (6a R, 7S, 9a S, 11 R*, 12 R*, 13a S)-11-bromo-4-carbamoyl-12-chloro-2, 3, 6, 6a, 7, 8, 9, 9a, 10, 11, 12, 13-dodecahydro-6a, 7,10,10-tetramethyl-3-oxo-1H-benzo[8,8a][1]benzopyrano[2,3-e]isoindole (209) (6a R, 7S, 9a S, 11 R*, 13a S)-12-bromo-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (210) (6a R, 7S, 9a S, 13a S)-5-bromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (211) (6a R, 7S, 9a S, 13a S)-12-amino-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (212) (1R*, 6a R, 7S, 9a S, 12 R*, 13a S)-5-bromo-12-chloro-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (213) (6a R, 7S, 9a S, 12 R*, 13a S)-12-bromo-2, 3, 6, 6a, 7, 8, 9, 9a, 10, 11, 12, 13-dodecahydro-5-methoxycarbonyl-6a,7,10,10-tetramethyl-3,11-dioxo-1H-benzo[8,8a][1]benzopyrano[2,3-e]isoindole (214) (6a R, 7S, 9a S, 11 R*, 12 R*, 13a S)-12-amino-11-chloro-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (215) (6a R, 7S, 9a S, 12 R*, 13a S)-5-carboxy-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (216) (6a R, 7S, 9a S, 11 R*, 12 R*, 13a S)-4-chloro-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3-e]isoindole (217) (6a R, 7S, 9a S, 12 R*, 13a S)-12-acetylamino-2, 3, 6a, 7, 8, 9, 9a, 10, 11, 12, 13-dodecahydro-6a,7,10,10-tetramethyl-5-nitro-3,11-dioxo-1H-benzo[8,8a][1]benzopyrano[2,3-e]isoindole (218) (1R*, 6a R, 7S, 9a S, 12 R*, 13a S)-2, 3, 6, 6a, 7, 8, 9, 9a, 10, 11, 12, 13-dodecahydro-1-hydroxyphenyl12-methoxy-6a,7,10,10-tetramethyl-4-nitro-3,11-dioxo-1H-benzo[8,8a][1]benzopyrano[2,3-e]isoindole (219) (6a R, 7S, 9a S, 12 R*, 13a S)-5-bromo-12-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (220) (1R*, 6a R, 7S, 9a S, 13a S)-5-bromo-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (221) (1R*, 6a R, 7S, 9a S, 12 R*, 13a S)-12-acetylamino-5-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (222) (1R*, 6a R, 7S, 9a S, 12 R*, 13a S)-4-chloro-2, 3, 6, 6a, 7, 8, 9, 9a, 10, 11, 12, 13-dodecahydro-1-hydroxy-6a,7,10,10-tetramethyl-12-methylamino-3,11-dioxo-1H-benzo[8,8a][1]benzopyrano[2,3-e]isoindole (223) (6a R, 7S, 9a S, 11 R*, 12 R*, 13a S)-11,12-dichloro-2, 3, 6, 6a, 7, 8, 9, 9a, 10, 11, 12, 13dodecahydro-6a,7,10,10-tetramethyl-4-nitro-3-oxo-1H-benzo[8,8a][1]benzopyrano[2,3-e]isoindole (224) (6a R, 7S, 9a S, 12 R*, 13a S)-2, 3, 6, 6a, 7, 8, 9, 9a, 10, 11, 12, 13-dodecahydro-12-hydroxy-6a,7,10,10-tetramethyl-3,11-dioxo-5-trifluoromethyl-1H-benzo[8,8a][1]benzopyrano[2,3-e]isoindole (225) (1R*, 6a R, 7S, 9a S, 12 R*, 13a S)-12-amino-2, 3, 6, 6a, 7, 8, 9, 9a, 10, 11, 12, 13-dodecahydro-1-methoxy-6a,7,10,10-tetramethyl-4-nitro-3,11-dioxo-1H-benzo[8,8a][1]benzopyrano[2,3-e]isoindole (226) (6a R, 7S, 9a S, 11 R*, 12 R*, 13a S)-5-carboxy-11-chloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (227) (6a R, 7S, 9a S, 11 R*, 12 R*, 13a S)-5-carboxy-11,12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (228) (6a R, 7S, 9a S, 11 R*, 12 R*, 13a S)-12-acetylamino-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (229) (6a R, 7S, 9a S, 13a S)-4-bromo-2, 3, 6, 6a, 7, 8, 9, 9a, 10, 13-decahydro-6a,7,10,10-tetramethyl-3-oxo-1H-benzo[8,8a][1]benzopyrano[2,3-e]isoindole (230) (1R*, 6a R, 7S, 9a S, 12 R*, 13a S)-4-bromo-12-chloro-2, 3, 6, 6a, 7, 8, 9, 9a, 10, 11, 12, 13-dodecahydro-1-methoxy-6a, 7,10,10-tetramethyl-3,11-dioxo-1H-benzo[8,8a][1]benzopyrano[2,3-e]isoindole (231) (6a R, 7S, 9a S, 12 R*, 13a S)-4-carboxy-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (232) (6a R, 7S, 9a S, 13a S)-5-bromo-2, 3, 6, 6a, 7, 8, 9, 9a, 10, 11, 12, 13-decahydro-6a,7,10,10-tetramethyl-3-oxo-1H-benzo[8,8a][1]benzopyrano[2,3-e]isoindole (233) (6a R, 7S, 9a S, 11 R*, 12 R*, 13a S)-2, 3, 6, 6a, 7, 8, 9, 9a, 10, 11, 12, 13-dodecahydro-11-hydroxy-6a,7,10,10-tetramethyl-12-methylamino-3oxo-4-trifluoromethyl-1H-benzo[8,8a][1]benzopyrano[2,3-e]isoindole (234) (6a R, 7S, 9a S, 11R*, 12 R*, 13a S)-12-bromo-5,11-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (235) (6a R, 7S, 9a S, 12 R*, 13a S)-2, 3, 6, 6a, 7, 8, 9, 9a, 10, 11, 12, 13-dodecahydro-12-hydroxy-6a,7,10,10-tetramethyl-3,11-dioxo-4-trifluoromethyl-1H-benzo[8,8a][1]benzopyrano[2,3-e]isoindole (236) (6a R, 7S, 9a S, 11 R*, 12 R*, 13a S)-11-chloro-2, 3, 6, 6a, 7, 8, 9, 9a, 10, 11, 12, 13-dodecahydro-12-methoxy-5-methoxycarbonyl-6a,7,10,10-tetramethyl-3-oxo-1H-benzo[8,8a][1]benzopyrano[2,3-e]isoindole (237) (6a R, 7S, 9a S, 11 R*, 12 R*, 13a S)-11-bromo-4-carbamoyl-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (238) (6a R, 7S, 9a S, 11 R*, 12 R*, 13a S)-12-amino-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (239) (6a R, 7S, 9a S, 11 R*, 12 R*, 13a S)-4,12-dibromo-11-chloro-2, 3, 6, 6a, 7, 8, 9, 9a, 10, 11, 12, (240) (6a R, 7S, 9a S, 11 R*, 12 R*, 13a S)-2, 3, 6, 6a, 7, 8, 9, 9a, 10, 11, 12, 13-dodecahydro-11,12-dihydroxy-6a,7,10,10-tetramethyl-4-nitro-3-oxo-1H-benzo[8,8a][1]benzopyrano[2,3-e]isoindole (241) (6a R, 7S, 9a S, 11 R*, 12 R*, 13a S)-12-bromo-2, 3, 6, 6a, 7, 8, 9, 9a, 10, 11, 12, 13-dodecahydro-4,11-dihydroxy-6a,7,10,10-tetramethyl-3-oxo-1H-benzo[8,8a][1]benzopyrano[2,3-e]isoindole (242) (6a R, 7S, 9a S, 11 R*, 12 R*, 13a S)-12-acetylamino-2, 3, 6, 6a, 7, 8, 9, 9a, 10, 11, 12, 13-dodecahydro-11-hydroxy-4-methoxy-6a,7,10,10-tetramethyl-3-oxo-1H-benzo[8,8a][1]benzopyrano[2,3-e]isoindole (243) (6a R, 7S, 9a S, 12 R*, 13a S)-12-acetylamino-4-bromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (244) (1R*, 6a R, 7S, 9a S, 12 R*, 13a S)-12-chloro-2, 3, 6, 6a, 7, 8, 9, 9a, 10, 11, 12, 13-dodecahydro-1-hydroxy-6a,7,10,10-tetramethyl-4-nitro-3,11-dioxo-1H-benzo[8,8a][1]benzopyrano[2,3-e]isoindole (245) (1R*, 6a R, 7S, 9a S, 12 R*, 13a S)-12-acetylamino-5-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (246) (6a R, 7S, 9a S, 11 R*, 12 R*, 13a S)-5,11-dichloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (247) (1R*, 6a R, 7S, 9a S, 13a S)-2, 3, 6, 6a, 7, 8, 9, 9a, 10, 11, 12, 13-dodecahydro-1-hydroxyphenyl-6a,7,10,10-tetramethyl-4-nitro-3,11-dioxo-1H-benzo[8,8a][1]benzopyrano[2,3-e]isoindole (248) (1R*, 6a R, 7S, 9a S, 13a S)-12-acetylamino-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (249) (6a R, 7S, 9a S, 11 R*, 12 R*, 13a S)-12-chloro-2, 3, 6, 6a, 7, 8, 9, 9a, 10, 11, 12, 13-dodecahydro-4,11-dihydroxy-6a,7,10,10-tetramethyl-3-oxo-1H-benzo[8,8a][1]benzopyrano[2,3-e]isoindole (250) (1R*, 6a R, 7S, 9a S, 12 R*, 13a S)-12-amino-4-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (251) (6a R, 7S, 9a S, 12 R*, 13a S)-5-bromo-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole (252) (1R*, 6a R, 7S, 9a S, 12 R*, 13a S)-12-chloro-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (253) (1R*, 6a R, 7S, 9a S, 12 R*, 13a S)-12-amino-2, 3, 6, 6a, 7, 8, 9, 9a, 10, 11, 12, 13-dodecahydro-1-hydroxyphenyl-6a,7,10,10-tetramethyl-5-nitro-3,11-dioxo-1H-benzo[8,8a][1]benzopyrano[2,3-e]isoindole (254) (1R*, 6a R, 7S, 9a S, 12 R*, 13a S)-4-chloro-2, 3, 6, 6a, 7, 8, 9, 9a, 10, 11, 12, 13-dodecahydro-1-methoxy-6a,7,10,10-tetramethyl-12-methylamino-3,11-dioxo-1H-benzo[8,8a][1]benzopyrano[2,3-e]isoindole (255) (6a R, 7S, 9a S, 13a S)-5-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (256) (6a R, 7S, 9a S, 12 R*, 13a S)-12-bromo-2, 3, 6, 6a, 7, 8, 9, 9a, 10, 11, 12, 13-dodecahydro-4-methoxycarbonyl-6a,7,10,10-tetramethyl-3,11-dioxo-1H-benzo[8,8a][1]benzopyrano[2,3-e]isoindole (257) (6a R, 7S, 9a S, 11 R*, 12 R*, 13a S)-12-amino-11-bromo-4-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (258) (1R*, 6a R, 7S, 9a S, 12 R*, 13a S)-12-acetylamino-2, 3, 6, 6a, 7, 8, 9, 9a, 10, 11, 12, 13-dodecahydro-1-hydroxy-6a,7,10,10-tetramethyl-5-nitro-3,11-dioxo-1H-benzo[8,8a][1]benzopyrano[2,3-e]isoindole (259) (1R*, 6a R, 7S, 9a S, 12 R*, 13a S)-12-chloro-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole (260) (1R*, 6a R, 7S, 9a S, 12 R*, 13a S)-12-bromo-5-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (261) (6a R, 7S, 9a S, 13a S)-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (262) (6a R, 7S, 9a S, 13a S)-5-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (263) (6a R, 7S, 9a S, 12 R*, 13a S)-12-acetylamino-2, 3, 6, 6a, 7, 8, 9, 9a, 10, 11, 12, 13-dodecahydro-4-methoxycarbonyl-6a,7,10,10-tetramethyl-3,11-dioxo-1H-benzo[8,8a][1]benzopyrano[2,3-e]isoindole (264) (1R*, 6a R, 7S, 9a S, 12 R*, 13a S)-2, 3, 6, 6a, 7, 8, 9, 9a, 10, 11, 12, 13-dodecahydro-12-methoxy-1-methoxyphenyl-6a,7,10,10-tetramethyl-3,11-dioxo-1H-benzo[8,8a][1]benzopyrano[2,3-e]isoindole (265) (1R*, 6a R, 7S, 9a S, 12 R*, 13a S)-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (266) (6a R, 7S, 9a S, 11 R*, 12 R*, 13a S)-12-amino-4-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (267) (6a R, 7S, 9a S, 11 R*, 12 R*, 13a S)-4-carbamoyl-2, 3, 6, 6a, 7, 8, 9, 9a, 10, 11, 12, 13-dodecahydro-11,12-dihydroxy-6a,7,10,10-tetramethyl-3-oxo-1H-benzo[8,8a][1]benzopyrano[2,3-e]isoindole (268) (6a R, 7S, 9a S, 11 R*, 12 R*, 13a S)-4-carboxy-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (269) (6a R, 7S, 9a S, 11 R*, 12 R*, 13a S)-4-carbamoyl-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (270) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (271) (6a R, 7S, 9a S, 11 R*, 12 R*, 13a S)-5,11-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (272) (6a R, 7S, 9a S, 12 R*, 13a S)-12-acetylamino-2, 3, 6, 6a, 7, 8, 9, 9a, 10, 11, 12, 13-dodecahydro-6a,7,10,10-tetramethyl-3,11-dioxo-5-trifluoromethyl-1H-benzo[8,8a][1]benzopyrano[2,3-e]isoindole (273) (6a R, 7S, 9a S, 12 R*, 13a S)-2, 3, 6, 6a, 7, 8, 9, 9a, 10, 11, 12, 13-dodecahydro-4-methoxy-6a,7,10,10- tetramethyl-12-methylamino-3,11-dioxo-1H-benzo[8,8a][1]benzopyrano[2,3-e]isoindole (274) (6a R, 7S, 9a S, 12 R*, 13a S)-11-chloro-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (275) (1R*, 6a R, 7S, 9a S, 12 R*, 13a S)-5-chloro-2, 3, 6, 6a, 7, 8, 9, 9a, 10, 11, 12, 13-dodecahydro-1-hydroxyphenyl12-methoxy-6a,7,10,10-tetramethyl-3,11-dioxo-1H-benzo[8,8a][1]benzopyrano[2,3-e]isoindole (276) (6a R, 7S, 9a S, 11 R*, 12 R*, 13a S)-12-amino-11-bromo-4-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (277) (6a R, 7S, 9a S, 12 R*, 13a S)-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (278) (6a R, 7S, 9a S, 13a S)-2, 3, 6, 6a, 7, 8, 9, 9a, 10, 11, 12, 13-dodecahydro-6a,7,10,10-tetramethyl-5-nitro-3,11-dioxo-1H-benzo[8,8a][1]benzopyrano[2,3-e]isoindole (279) (6a R, 7S, 9a S, 11 R*, 12 R*, 13a S)-11-chloro-2, 3, 6, 6a, 7, 8, 9, 9a, 10, 11, 12, 13-dodecahydro-12-hydroxy-4-methoxycarbonyl-6a,7,10,10-tetramethyl-3-oxo-1H-benzo[8,8a][1]benzopyrano[2,3-e]isoindole (280) (1R*, 6a R, 7S, 9a S, 12 R*, 13a S)-5,12-dibromo-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (281) (6a R, 7S, 9a S, 11 R*, 12 R*, 13a S)-12-acetylamino-11-chloro-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (282) (1R*, 6a R, 7S, 9a S, 12 R*, 13a S)-12-acetylamino-5-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (283) (6a R, 7S, 9a S, 12 R*, 13a S)-2, 3, 6, 6a, 7, 8, 9, 9a, 10, 11, 12, 13-dodecahydro-5-methoxycarbonyl-6a,7,10,10-tetramethyl-12-methylamino-3,11-dioxo-1H-benzo[8,8a][1]benzopyrano[2,3-e]isoindole (284) (1R*, 6a R, 7S, 9a S, 13a S)-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (285) (1R*, 6a R, 7S, 9a S, 13a S)-2, 3, 6, 6a, 7, 8, 9, 9a, 10, 11, 12, 13-dodecahydro-12-methoxy-6a,7,10,10-tetramethyl-3-oxo-4-trifluoromethyl-1H-benzo[8,8a][1]benzopyrano[2,3-e]isoindole (286) (1R*, 6a R, 7S, 9a S, 12 R*, 13a S)-5-bromo-12-chloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (287) (6a R, 7S, 9a S, 12 R*, 13a S)-12-chloro-4-cyano-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (288) (6a R, 7S, 9a S, 12 R*, 13a S)-12-acetylamino-2, 3, 6, 6a, 7, 8, 9, 9a, 10, 11, 12, 13-dodecahydro-6a,7,10,10-tetramethyl-3,11-dioxo-4-trifluoromethyl-1H-benzo[8,8a][1]benzopyrano[2,3-e]isoindole (289) (6a R, 7S, 9a S, 12 R*, 13a S)-5-chloro-2, 3, 6, 6a, 7, 8, 9, 9a, 10, 11, 12, 13-dodecahydro-12-hydroxy-6a,7,10,10-tetramethyl-3,11-dioxo-1H-benzo[8,8a][1]benzopyrano[2,3-e]isoindole (290) (6a R, 7S, 9a S, 12 R*, 13a S)-12-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (291) (6a R, 7S, 9a S, 11 R*, 12 R*, 13a S)-5-carbamoyl-11-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (292) (6a R, 7S, 9a S, 12 R*, 13a S)-5-carbamoyl-2, 3, 6, 6a, 7, 8, 9, 9a, 10, 11, 12, 13-dodecahydro-12-hydroxy-6a,7,10,10-tetramethyl-3,11dioxo-1H-benzo[8,8a][1]benzopyrano[2,3-e]isoindole (293) (6a R, 7S, 9a S, 12 R*, 13a S)-4-bromo-2, 3, 6, 6a, 7, 8, 9, 9a, 10, 11, 12, 13-dodecahydro-12-hydroxy-6a,7,10,10-tetramethyl-3,11-dioxo-1H-benzo[8,8a][1]benzopyrano[2,3-e]isoindole (294) (6a R, 7S, 9a S, 11 R*, 12 R*, 13a S)-11-bromo-12chloro-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (295) (6a R, 7S, 9a S, 11 R*, 12 R*, 13a S)-12-bromo-2, 3, 6, 6a, 7, 8, 9, 9a, 10, 11, 12, 13-dodecahydro-11-hydroxy-5-methoxycarbonyl-6a,7,10,10-tetramethyl-3-oxo-1H-benzo[8,8a][1]benzopyrano[2,3-e]isoindole (296) (1R*, 6a R, 7S, 9a S, 12 R*, 13a S)-12-acetylamino-4-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (297) (1R*, 6a R, 7S, 9a S, 12 R*, 13a S)-5-cyano-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (298) (6a R, 7S, 9a S, 11 R*, 12 R*, 13a S)-11-bromo-4-carbamoyl-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (299) (6a R, 7S, 9a S, 11 R*, 12 R*, 13a S)-4,11-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (300) (6a R, 7S, 9a S, 12 R*, 13a S)-12-chloro-2, 3, 6, 6a, 7, 8, 9, 9a, 10, 11, 12, 13-dodecahydro-4-methoxy-6a,7,10,10-tetramethyl-3,11-dioxo-1H-benzo[8,8a][1]benzopyrano[2,3-e]isoindole (301) (1R*, 6a R, 7S, 9a S, 12 R*, 13a S)-4-chloro-2, 3, 6, 6a, 7, 8, 9, 9a, 10, 11, 12, 13-dodecahydro-12-hydroxy-1-methoxy-6a,7,10,10-tetramethyl-3,11-dioxo-1H-benzo[8,8a][1]benzopyrano[2,3-e]isoindole (302) (1R*, 6a R, 7S, 9a S, 12 R*, 13a S)-2, 3, 6, 6a, 7, 8, 9, 9a, 10, 11, 12, 13-dodecahydro-6a,7,10,10-tetramethyl-12-methylamino-3-oxo-4-trifluoromethyl-1H-benzo[8,8a][1]benzopyrano[2,3-e]isoindole (303) (1R*, 6a R, 7S, 9a S, 12 R*, 13a S)-12-bromo-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (304) (6a R, 7S, 9a S, 13a S)-2, 3, 6, 6a, 7, 8, 9, 9a, 10, 11, 12, 13-dodecahydro-6a,7,10,10-tetramethyl-4-nitro-3,11-dioxo-1H-benzo[8,8a][1]benzopyrano[2,3-e]isoindole (305) (6a R, 7S, 9a S, 11 R*, 12 R*, 13a S)-5-cyano-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3-e]isoindole (306) (6a R, 7S, 9a S, 11 R*, 12 R*, 13a S)-11-bromo-4-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (307) (6a R, 7S, 9a S, 12 R*, 13a S)-4,12-dichloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (308) (6a R, 7S, 9a S, 12 R*, 13a S)-5,12-dibromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (309) (6a R, 7S, 9a S, 11 R*, 12 R*, 13a S)-12-acetylamino-11-chloro-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (310) (6a R, 7S, 9a S, 11 R*, 12 R*, 13a S)-12-chloro-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (311) (6a R, 7S, 9a S, 12 R*, 13a S)-4-cyano-2, 3, 6, 6a, 7, 8, 9, 9a, 10, 11, 12, 13-dodecahydro-12-hydroxy-6a,7,10,10-tetramethyl-3,11-dioxo-1H-benzo[8,8a][1]benzopyrano[2,3-e]isoindole (312) (1R*, 6a R, 7S, 9a S, 12 R*, 13a S)-12-chloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (313) (6a R, 7S, 9a S, 12 R*, 13a S)-12-acetylamino-5-carboxy-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (314) (6a R, 7S, 9a S, 11 R*, 12 R*, 13a S)-2, 3, 6, 6a, 7, 8, 9, 9a, 10, 11, 12, 13-dodecahydro-11-hydroxy-12-methoxy-6a,7,10,10-tetramethyl-5-nitro-3-oxo-1H-benzo[8,8a][1]benzopyrano[2,3-e]isoindole (315) (6a R, 7S, 9a S, 11 R*, 12 R*, 13a S)-11,12-dichloro-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (316) (6a R, 7S, 9a S, 11 R*, 12 R*, 13a S)-5-bromo-11,12-epoxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (317) (6a R, 7S, 9a S, 12 R*, 13a S)-5,12-dichloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (318) (6a R, 7S, 9a S, 12 R*, 13a S)-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (319) (6a R, 7S, 9a S, 12 R*, 13a S)-2, 3, 6, 6a, 7, 8, 9, 9a, 10, 11, 12, 13-dodecahydro-12-hydroxy-5-methoxycarbonyl-6a,7,10,10-tetramethyl-3,11-dioxo-1H-benzo[8,8a][1]benzopyrano[2,3-e]isoindole (320) (1R*, 6a R, 7S, 9a S, 13a S)-4-bromo-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (321) (6a R, 7S, 9a S, 13a S)-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (322) (1R*, 6a R, 7S, 9a S, 12 R*, 13a S)-12-bromo-4-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (323) (1R*, 6a R, 7S, 9a S, 12 R*, 13a S)-5-carbamoyl-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (324) (6a R, 7S, 9a S, 11 R*, 12 R*, 13a S)-11-bromo-2, 3, 6, 6a, 7, 8, 9, 9a, 10, 11, 12, 13-dodecahydro-4-methoxy-6a,7,10,10-tetramethyl-12-methylamino-3-oxo-1H-benzo[8,8a][1]benzopyrano[2,3-e]isoindole (325) (1R*, 6a R, 7S, 9a S, 12 R*, 13a S)-12-bromo-2, 3, 6, 6a, 7, 8, 9, 9a, 10, 11, 12, 13-dodecahydro-1-methoxyphenyl-6a,7,10,10-tetramethyl-5-nitro-3,11dioxo-1H-benzo[8,8a][1]benzopyrano[2,3-e]isoindole (326) (6a R, 7S, 9a S, 11 R*, 12 R*, 13a S)-5-carbamoyl-2, 3, 6, 6a, 7, 8, 9, 9a, 10, 11, 12, 13-dodecahydro-11-hydroxy-12-methoxy-6a,7,10,10-tetramethyl-3-oxo-1H-benzo[8,8a][1]benzopyrano[2,3-e]isoindole (327) (6a R, 7S, 9a S, 11 R*, 12 R*, 13a S)-12-acetylamino-4-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (328) (6a R, 7S, 9a S, 11 R*, 12 R*, 13a S)-11,12-dichloro-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (329) (6a R, 7S, 9a S, 11 R*, 12 R*, 13a S)-12chloro-2, 3, 6, 6a, 7, 8, 9, 9a, 10, 11, 12, 13-dodecahydro-11-hydroxy-5-methoxycarbonyl-6a,7,10,10-tetramethyl-3-oxo-1H-benzo[8,8a][1]benzopyrano[2,3-e]isoindole (330) (6a R, 7S, 9a S, 11 R*, 12 R*, 13a S)-11-hydroxy-5-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (331) (6a R, 7S, 9a S, 11 R*, 12 R*, 13a S)-12-chloro-2, 3, 6, 6a, 7, 8, 9, 9a, 10, 11, 12, 13-dodecahydro-11-hydroxy-6a,7,10,10-tetramethyl-5-nitro-3-oxo-1H-benzo[8,8a][1]benzopyrano[2,3-e]isoindole (332) (6a R, 7S, 9a S, 11 R*, 12 R*, 13a S)-12-acetylamino-5-cyano-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (333) (1R*, 6a R, 7S, 9a S, 12 R*, 13a S)-4,12-dibromo-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (334) (6a R, 7S, 9a S, 13a S)-2, 3, 6, 6a, 7, 8, 9, 9a, 10, 11, 12, 13-dodecahydro-6a,7,10,10-tetramethyl-3,11-dioxo-5-trifluoromethyl-1H-benzo[8,8a][1]benzopyrano[2,3-e]isoindole (335) (1R*, 6a R, 7S, 9a S, 12 R*, 13a S)-2, 3, 6, 6a, 7, 8, 9, 9a, 10, 11, 12, 13-dodecahydro-6a,7,10,10-tetramethyl-5-nitro-3,11-dioxo-1H-benzo[8,8a][1]benzopyrano[2,3-e]isoindole (336) (1R*, 6a R, 7S, 9a S, 12 R*, 13a S)-4,12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (337) (1R*, 6a R, 7S, 9a S, 12 R*, 13a S)-4-cyano-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (338) (6a R, 7S, 9a S, 12 R*, 13a S)-2, 3, 6, 6a, 7, 8, 9, 9a, 10, 11, 12, 13-dodecahydro-12-methoxy-6a,7,10,10-tetramethyl-3,11-dioxo-4-trifluoromethyl-1H-benzo[8,8a][1]benzopyrano[2,3-e]isoindole (339) (6a R, 7S, 9a S, 11 R*, 12 R*, 13a S)-12-chloro-2, 3, 6, 6a, 7, 8, 9, 9a, 10, 11, 12, 13-dodecahydro-11-hydroxy-4-methoxy-6a,7,10,10-tetramethyl-3-oxo-1H-benzo[8,8a][1]benzopyrano[2,3-e]isoindole (340) (6a R, 7S, 9a S, 12 R*, 13a S)-12-amino-4-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (341) (1R*, 6a R, 7S, 9a S, 12 R*, 13a S)-4-chloro-2, 3, 6, 6a, 7, 8, 9, 9a, 10, 11, 12, 13-dodecahydro-12-hydroxy-1-methoxyphenyl-6a,7,10,10-tetramethyl-3,11-dioxo-1H-benzo[8,8a][1]benzopyrano[2,3-e]isoindole (342) (6a R, 7S, 9a S, 12 R*, 13a S)-11-chloro-2, 3, 6, 6a, 7, 8, 9, 9a, 10, 11, 12, 13-dodecahydro-6a,7,10,10-tetramethyl-12-methylamino-3-oxo-5-trifluoromethyl-1H-benzo[8,8a][1]benzopyrano[2,3-e]isoindole (343) (6a R, 7S, 9a S, 11R*, 12 R*, 13a S)-12-acetylamino-11-bromo-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (344) (6a R, 7S, 9a S, 11R*, 12 R*, 13a S)-12-acetylamino-2, 3, 6, 6a, 7, 8, 9, 9a, 10, 11, 12, 13-dodecahydro-11-hydroxy-6a,7,10,10-tetramethyl-3-oxo-4-trifluoromethyl-1H-benzo[8,8a][1]benzopyrano[2,3-e]isoindole (345) (1R*, 6a R, 7S, 9a S, 12 R*, 13a S)-12-acetylamino-4-chloro-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (346) (1R*, 6a R, 7S, 9a S, 12 R*, 13a S)-5-carbamoyl-12-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (347) (6a R, 7S, 9a S, 12 R*, 13a S)-12-amino-5-carboxy-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (348) (6a R, 7S, 9a S, 11R*, 12 R*, 13a S)-5-bromo-11-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (349) (6a R, 7S, 9a S, 11R*, 13a S)-5,12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (350) (1R*, 6a R, 7S, 9a S, 12 R*, 13a S)-12-amino-5-bromo-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (351) (1R*, 6a R, 7S, 9a S, 12 R*, 13a S)-2, 3, 6, 6a, 7, 8, 9, 9a, 10, 11, 12, 13-dodecahydro-6a,7,10,10-tetramethyl-12-methylamino-4-nitro-3,11-dioxo-1H-benzo[8,8a][1]benzopyrano[2,3-e]isoindole (352) (6a R, 7S, 9a S, 11R*, 12 R*, 13a S)-12-amino-5-carbamoyl-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (353) (6a R, 7S, 9a S, 11 R*, 12 R*, 13a S)-12-acetylamino-4-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (354) (1R*, 6a R, 7S, 9a S, 12 R*, 13a S)-5-bromo-2, 3, 6, 6a, 7, 8, 9, 9a, 10, 11, 12, 13-dodecahydro-1-hydroxyphenyl-6a,7,10,10-tetramethyl-12-methylamino-3,11-dioxo-1H-benzo[8,8a][1]benzopyrano[2,3-e]isoindole (355) (1R*, 6a R, 7S, 9a S, 12 R*, 13a S)-5-chloro-2, 3, 6, 6a, 7, 8, 9, 9a, 10, 11, 12, 13-dodecahydro-12-hydroxy-1-methoxy-6a,7,10,10-tetramethyl-3,11-dioxo-1H-benzo[8,8a][1]benzopyrano[2,3-e]isoindole (356) (1R*, 6a R, 7S, 9a S, 12 R*, 13a S)-11-bromo-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (357) (6a R, 7S, 9a S, 12 R*, 13a S)-4-chloro-2, 3, 6, 6a, 7, 8, 9, 9a, 10, 11, 12, 13-dodecahydro-12-hydroxy-6a,7,10,10-tetramethyl-3,11-dioxo-1H-benzo[8,8a][1]benzopyrano[2,3-e]isoindole (358) (6a R, 7S, 9a S, 12 R*, 13a S)-12-amino-2, 3, 6, 6a, 7, 8, 9, 9a, 10, 11, 12, 13-dodecahydro-6a,7,10,10-tetramethyl-3,11-dioxo-4-trifluoromethyl-1H-benzo[8,8a][1]benzopyrano[2,3-e]isoindole (359) (1R*, 6a R, 7S, 9a S, 13a S)-4-bromo-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (360) (6a R, 7S, 9a S, 13a S)-4-bromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (361) (6a R, 7S, 9a S, 11 R*, 13a S)-5-chloro-2, 3, 6, 6a, 7, 8, 9, 9a, 10, 11, 12, 13-dodecahydro-11-hydroxy-12-methoxy-6a,7,10,10-tetramethyl-3,11-dioxo-1H-benzo[8,8a][1]benzopyrano[2,3-e]isoindole (362) (6a R, 7S, 9a S, 11R*, 12 R*, 13a S)-11,12-dichloro-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (363) (6a R, 7S, 9a S, 11 R*, 12 R*, 13a S)-11-bromo-5-carbamoyl-12-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (364) (6a R, 7S, 9a S, 11 R*, 12 R*, 13a S)-11-bromo-5-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (365) (6a R, 7S, 9a S, 11R*, 12 R*, 13a S)-12-amino-2, 3, 6, 6a, 7, 8, 9, 9a, 10, 11, 12, 13-dodecahydro-11-hydroxy-6a,7,10,10-tetramethyl-4-nitro-3-oxo-1H-benzo[8,8a][1]benzopyrano[2,3-e]isoindole (366) (6a R, 7S, 9a S, 12 R*, 13a S)-12-bromo-4-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (367) (6a R, 7S, 9a S, 11R*, 12 R*, 13a S)-11-chloro-2, 3, 6, 6a, 7, 8, 9, 9a, 10, 11, 12, 13-dodecahydro-12-methoxy-4-methoxycarbonyl-6a,7,10,10-tetramethyl-3-oxo-1H-benzo[8,8a][1]benzopyrano[2,3-e]isoindole (368) (6a R, 7S, 9a S, 11 R*, 12 R*, 13a S)-12-amino-11-bromo-5-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (369) (1R*, 6a R, 7S, 9a S, 12 R*, 13a S)-5-bromo-2, 3, 6, 6a, 7, 8, 9, 9a, 10, 11, 12, 13-dodecahydro-1-hydroxy-12-methoxy-6a,7,10,10-tetramethyl-3,11-dioxo-1H-benzo[8,8a][1]benzopyrano[2,3-e]isoindole (370) (6a R, 7S, 9a S, 11 R*, 12 R*, 13a S)-12-amino-11-bromo-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole (371) (1R*, 6a R, 7S, 9a S, 12 R*, 13a S)-4-bromo-2, 3, 6, 6a, 7, 8, 9, 9a, 10, 11, 12, 13-dodecahydro-1,12-dihydroxy-6a,7,10,10-tetramethyl-3,11-dioxo-1H-benzo[8,8a][1]benzopyrano[2,3-e]isoindole (372) (1R*, 6a R, 7S, 9a S, 13a S)-2, 3, 6, 6a, 7, 8, 9, 9a, 10, 11, 12, 13-dodecahydro-6a,7,10,10-tetramethyl-4-nitro-3,11-dioxo-1H-benzo[8,8a][1]benzopyrano[2,3-e]isoindole (373) (1R*, 6a R, 7S, 9a S, 12 R*, 13a S)-12-acetylamino-2, 3, 6, 6a, 7, 8, 9, 9a, 10, 11, 12, 13-dodecahydro-1-methoxyphenyl-6a,7,10,10-tetramethyl-4-nitro-3,11-dioxo-1H-benzo[8,8a][1]benzopyrano[2,3-e]isoindole (374) (1R*, 6a R, 7S, 9a S, 12 R*, 13a S)-12-amino-5-bromo-2, 3, 6, 6a, 7, 8, 9, 9a, 10, 11, 12, 13-dodecahydro- 1-hydroxyphenyl-6a,7,10,10-tetramethyl-3,11-dioxo-1H-benzo[8,8a][1]benzopyrano[2,3-e]isoindole (375) (1R*, 6a R, 7S, 9a S, 12 R*, 13a S)-12-amino-5-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (376) (6a R, 7S, 9a S, 11 R*, 12 R*, 13a S)-11-bromo-2, 3, 6, 6a, 7, 8, 9, 9a, 10, 11, 12, 13-dodecahydro-4-methoxycarbonyl-6a,7,10,10-tetramethyl-12-methylamino-3-oxo-1H-benzo[8,8a][1]benzopyrano[2,3-e]isoindole (377) (6a R, 7S, 9a S, 11 R*, 12 R*, 13a S)-5-carboxy-11-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (378) (6a R, 7S, 9a S, 11R*, 12 R*, 13a S)-2, 3, 6, 6a, 7, 8, 9, 9a, 10, 11, 12, 13-dodecahydro-11-hydroxy-12-methoxy-4-methoxycarbonyl-6a,7,10,10-tetramethyl-3,11-dioxo-1H-benzo[8,8a][1]benzopyrano[2,3-e]isoindole (379) (6a R, 7S, 9a S, 12 R*, 13a S)-12-bromo-2, 3, 6, 6a, 7, 8, 9, 9a, 10, 11, 12, 13-dodecahydro-6a,7,10,10-tetramethyl-3,11-dioxo-5-trifluoromethyl-1H-benzo[8,8a][1]benzopyrano[2,3-e]isoindole (380) (6a R, 7S, 9a S, 11 R*, 12 R*, 13a S)-11-chloro-5-cyano-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (381) (6a R, 7S, 9a S, 11 R*, 12 R*, 13a S)-12-amino-11-chloro-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (382) (6a R, 7S, 9a S, 12 R*, 13a S)-4-chloro-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole (383) (1R*, 6a R, 7S, 9a S, 12 R*, 13a S)-12-chloro-2, 3, 6, 6a, 7, 8, 9, 9a, 10, 11, 12, 13-dodecahydro-1-hydroxyphenyl-6a,7,10,10-tetramethyl-4-nitro-3,11-dioxo-1H-benzo[8,8a][1]benzopyrano[2,3-e]isoindole (384) (6a R, 7S, 9a S, 11 R*, 12 R*, 13a S)-12-amino-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (385) (6a R, 7S, 9a S, 11 R*, 12 R*, 13a S)-11-bromo-2, 3, 6, 6a, 7, 8, 9, 9a, 10, 11, 12, 13-dodecahydro-12-methoxy-4-methoxycarbonyl-6a,7,10,10-tetramethyl-3-oxo-1H-benzo[8,8a][1]benzopyrano[2,3-e]isoindole (386) (6a R, 7S, 9a S, 11 R*, 12 R*, 13a S)-2, 3, 6, 6a, 7, 8, 9, 9a, 10, 11, 12, 13-dodecahydro-11-hydroxy-5-methoxycarbonyl-6a,7,10,10-tetramethyl-3-oxo-1H-benzo[8,8a][1]benzopyrano[2,3-e]isoindole (387) (6a R, 7S, 9a S, 12 R*, 13a S)-12-acetylamino-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (388) (6a R, 7S, 9a S, 13a S)-4-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (389) (1R*, 6a R, 7S, 9a S, 12 R*, 13a S)-12-amino-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (390) (6a R, 7S, 9a S, 11 R*, 12 R*, 13a S)-11-chloro-2, 3, 6, 6a, 7, 8, 9, 9a, 10, 11, 12, 13-dodecahydro-4-methoxycarbonyl-6a,7,10,10-tetramethyl-12-methylamino-3-oxo-1H-benzo[8,8a][1]benzopyrano[2,3-e]isoindole (391) (6a R, 7S, 9a S, 11 R*, 12 R*, 13a S)-12-acetylamino-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (392) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (393) (6a R, 7S, 9a S, 11 R*, 12 R*, 13a S)-11-bromo-4-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (394) (6a R, 7S, 9a S, 11 R*, 12 R*, 13a S)-12-acetylamino-4-carboxy-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (395) (6a R, 7S, 9a S, 11 R*, 12 R*, 13a S)-12-acetylamino-5-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (396) (6a R, 7S, 9a S, 11 R*, 12 R*, 13a S)-11-chloro-2, 3, 6, 6a, 7, 8, 9, 9a, 10, 11, 12, 13-dodecahydro-12-hydroxy-6a,7,10,10-tetramethyl-4-nitro-3-oxo-1H-benzo[8,8a][1]benzopyrano[2,3-e]isoindole (397) (6a R, 7S, 9a S, 12 R*, 13a S)-4-carboxy-2, 3, 6, 6a, 7, 8, 9, 9a, 10, 11, 12, 13-dodecahydro-12-hydroxy-6a,7,10,10-tetramethyl-3,11-dioxo-1H-benzo[8,8a][1]benzopyrano[2,3-e]isoindole (398) (6a R, 7S, 9a S, 11 R*, 12 R*, 13a S)-11-bromo-12-chloro-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (399) (6a R, 7S, 9a S, 11 R*, 12 R*, 13a S)-5-cyano-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (400) (1R*, 6a R, 7S, 9a S, 12 R*, 13a S)-5,12-dichloro-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (401) (6a R, 7S, 9a S, 13a S)-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (402) (6a R, 7S, 9a S, 12 R*, 13a S)-12-amino-2, 3, 6, 6a, 7, 8, 9, 9a, 10, 11, 12, 13-dodecahydro-4-hydroxy-6a,7,10,10-tetramethyl-3,11-dioxo-1H-benzo[8,8a][1]benzopyrano[2,3-e]isoindole (403) (1R*, 6a R, 7S, 9a S, 12 R*, 13a S)-2, 3, 6, 6a, 7, 8, 9, 9a, 10, 11, 12, 13-dodecahydro-12-hydroxy-1-hydroxyphenyl-6a,7,10,10-tetramethyl-4-nitro-3,11-dioxo-1H-benzo[8,8a][1]benzopyrano[2,3-e]isoindole (404) (6a R, 7S, 9a S, 13a S)-5-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (405) (6a R, 7S, 9a S, 13a S)-11-bromo-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (406) (6a R, 7S, 9a S, 12 R*, 13a S)-12-acetylamino-4-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (407) (6a R, 7S, 9a S, 11 R*, 12 R*, 13a S)-12-bromo-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (408) (1R*, 6a R, 7S, 9a S, 12 R*, 13a S)-5,12dibromo-2, 3, 6, 6a, 7, 8, 9, 9a, 10, 11, 12, 13-dodecahydro-1,12- dimethoxy-6a,7,10,10-tetramethyl-3,11-dioxo-1H-benzo [8,8a][1]benzopyrano[2,3-e]isoindole (409) (1R*, 6a R, 7S, 9a S, 12 R*, 13a S)-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e] isoindole (410) (1R*, 6a R, 7S, 9a S, 12 R*, 13a S)-4-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1] benzopyrano[2,3-e]isoindole (411) (1R*, 6a R, 7S, 9a S, 12 R*, 13a S)-12-acetylamino-5-chloro-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano [2,3-e]isoindole (412) (1R*, 6a R, 7S, 9a S, 12 R*, 13a S)-2, 3, 6, 6a, 7, 8, 9, 9a, 10, 11, 12, 13-dodecahydro-11-hydroxy-6a,7,10,10-tetramethyl-5-nitro-3-oxo-1H-benzo[8,8a][1] benzopyrano[2,3-e]isoindole (413) (6a R, 7S, 9a S, 13a S)-2, 3, 6, 6a, 7, 8, 9, 9a, 10, 13-dodecahydro-6a,7,10,10-tetramethyl-3-oxo-1H-benzo [8,8a][1]benzopyrano[2,3-e]isoindole (414) (1R*, 6a R, 7S, 9a S, 12 R*, 13a S)-12-acetylamino-2, 3, 6, 6a, 7, 8, 9, 9a, 10, 11, 12, 13-dodecahydro-1-methoxy-6a,7,10,10-tetramethyl-5-nitro-3,11-dioxo-1H-benzo[8,8a][1]benzopyrano[2,3-e]isoindole (415) (6a R, 7S, 9a S, 13a S)-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (416) (6a R, 7S, 9a S, 11 R*, 12 R*, 13a S)-11,12-dichloro-2, 3, 6, 6a, 7, 8, 9, 9a, 10, 11, 12, 13-dodecahydro-6a,7, 10,10-tetramethyl-3-oxo-5-trifluoromethyl-1H-benzo[8, 8a][1]benzopyrano[2,3-e]isoindole (417) (6a R, 7S, 9a S, 13a S)-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e] isoindole (418) (6a R, 7S, 9a S, 11 R*, 12 R*, 13a S)-12-bromo-2, 3, 6, 6a, 7, 8, 9, 9a, 10, 11, 12, 13-dodecahydro-11-hydroxy-6a,7,10,10-tetramethyl-5-nitro-3-oxo-1H-benzo[8,8a][1] benzopyrano[2,3-e]isoindole (419) (6a R, 7S, 9a S, 13a S)-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (420) (6a R, 7S, 9a S, 11 R*, 12 R*, 13a S)-12-amino-4, 11-dibromo-2, 3, 6, 6a, 7, 8, 9, 9a, 10, 11, 12, 13-dodecahydro-6a,7,10,10-tetramethyl-3-oxo-1H-benzo [8,8a][1]benzopyrano[2,3-e]isoindole (421) (1R*, 6a R, 7S, 9a S, 12 R*, 13a S)-4-bromo-2, 3, 6, 6a, 7, 8, 9, 9a, 10, 11, 12, 13-dodecahydro-1-hydroxyphenyl-6a,7,10,10-tetramethyl-12-methylamino-3,11-dioxo-1H-benzo[8,8a][1]benzopyrano[2,3-e] isoindole (422) (6a R, 7S, 9a S, 11 R*, 12 R*, 13a S)-11-bromo-5-carboxy-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (423) (6a R, 7S, 9a S, 12 R*, 13a S)-12-amino-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano [2,3-e]isoindole (424) (6a R, 7S, 9a S, 12 R*, 13a S)-12-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano [2,3-e]isoindole (425) (6a R, 7S, 9a S, 12 R*, 13a S)-11-chloro-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1] benzopyrano[2,3-e]isoindole (426) (6a R, 7S, 9a S, 12 R*, 13a S)-12-bromo-5-cyano-2, 3, 6, 6a, 7, 8, 9, 9a, 10, 11, 12, 13-dodecahydro-6a,7,10, 10-tetramethyl-3,11-dioxo-1H-benzo[8,8a][1] benzopyrano[2,3-e]isoindole (427) (1R*, 6a R, 7S, 9a S, 13a S)-2, 3, 6, 6a, 7, 8, 9, 9a, 10, 11, 12, 13-dodecahydro-1-methoxyphenyl-6a,7,10,10-tetramethyl-5-nitro-3,11-dioxo-1H-benzo[8,8a][1] benzopyrano[2,3-e]isoindole (428) (1R*, 6a R, 7S, 9a S, 12 R*, 13a S)-4-chloro-2, 3, 6, 6a, 7, 8, 9, 9a, 10, 11, 12, 13-dodecahydro-1-hydroxy-12-methoxy-6a,7,10,10-tetramethyl-3,11-dioxo-1H-benzo[8,8a][1]benzopyrano[2,3-e]isoindole (429) (6a R, 7S, 9a S, 11 R*, 12 R*, 13a S)-5-cyano-2, 3, 6, 6a, 7, 8, 9, 9a, 10, 11, 12, 13-dodecahydro-1-hydroxy-12-methoxy-6a,7,10,10-tetramethyl-3,11-dioxo-1H-benzo[8,8a][1]benzopyrano[2,3-e]isoindole (430) (6a R, 7S, 9a S, 11 R*, 12 R*, 13a S)-11-bromo-4-carboxy-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (431) (6a R, 7S, 9a S, 11 R*, 12 R*, 13a S)-12-bromo-5-carbamoyl-11-chloro-2, 3, 6, 6a, 7, 8, 9, 9a, 10, 11, 12, 13-dodecahydro-6a,7,10,10-tetramethyl-3-oxo-1H-benzo [8,8a][1]benzopyrano[2,3-e]isoindole (432) (6a R, 7S, 9a S, 11 R*, 12 R*, 13a S)-12-bromo-2, 3, 6, 6a, 7, 8, 9, 9a, 10, 11, 12, 13-dodecahydro-11-hydroxy-4-methoxy-6a,7,10,10-tetramethyl-3,11-dioxo-1H-benzo [8,8a][1]benzopyrano[2,3-e]isoindole (433) (6a R, 7S, 9a S, 11 R*, 12 R*, 13a S)-12-bromo-2, 3, 6, 6a, 7, 8, 9, 9a, 10, 11, 12, 13-dodecahydro-11-hydroxy-6a,7,10,10-tetramethyl-4-nitro-3-oxo-1H-benzo[8,8a][1] benzopyrano[2,3-e]isoindole (434) (1R*, 6a R, 7S, 9a S, 12 R*, 13a S)-5-bromo-2, 3, 6, 6a, 7, 8, 9, 9a, 10, 11, 12, 13-dodecahydro-12-hydroxy-1-hydroxyphenyl-6a,7,10,10-tetramethyl-3,11-dioxo-1H-benzo[8,8a][1]benzopyrano[2,3-e]isoindole (435) (6a R, 7S, 9a S, 11 R*, 12 R*, 13a S)-12-acetylamino-5-chloro-2, 3, 6, 6a, 7, 8, 9, 9a, 10, 11, 12, 13-dodecahydro-4,11-dihydroxy-6a,7,10,10-tetramethyl-3-oxo-1H-benzo[8,8a][1]benzopyrano[2,3-e]isoindole (436) (6a R, 7S, 9a S, 11 R*, 12 R*, 13a S)-11-chloro-2, 3, 6, 6a, 7, 8, 9, 9a, 10, 11, 12, 13-dodecahydro-4-methoxy-6a,7,10,10-tetramethyl-12-methylamino-3-oxo-1H-benzo [8,8a][1]benzopyrano[2,3-e]isoindole (437) (6a R, 7S, 9a S, 11 R*, 12 R*, 13a S)-4,11,12-trichloro-2, 3, 6, 6a, 7, 8, 9, 9a, 10, 11, 12, 13-dodecahydro-6a,7,10,10-tetramethyl-3-oxo-1H-benzo [8,8a][1]benzopyrano[2,3-e]isoindole (438) (6a R, 7S, 9a S, 11 R*, 12 R*, 13a S)-11-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1] benzopyrano[2,3-e]isoindole (439) (1R*, 6a R, 7S, 9a S, 12 R*, 13a S)-2, 3, 6, 6a, 7, 8, 9, 9a, 10, 11, 12, 13-dodecahydro-1-methoxy-6a,7,10,10-tetramethyl-12-methylamino-5-nitro-3,11-dioxo-1H-benzo[8,8a][1]benzopyrano[2,3-e]isoindole (440) (6a R, 7S, 9a S, 12 R*, 13a S)-12-bromo-2, 3, 6, 6a, 7, 8, 9, 9a, 10, 11, 12, 13-dodecahydro-4-hydroxy-6a,7, 10,10-tetramethyl-3,11-dioxo-1H-benzo[8,8a][1] benzopyrano[2,3-e]isoindole (441) (1R*, 6a R, 7S, 9a S, 12 R*, 13a S)-2, 3, 6, 6a, 7, 8, 9, 9a, 10, 11, 12, 13-dodecahydro-1-methoxyphenyl-6a, 7,10,10-tetramethyl-12-methylamino-3,11-dioxo-1H-benzo[8,8a][1]benzopyrano[2,3-e]isoindole (442) (6a R, 7S, 9a S, 11 R*, 12 R*, 13a S)-5-chloro-2, 3, 6, 6a, 7, 8, 9, 9a, 10, 11, 12, 13-dodecahydro-11,12- dihydroxy-6a,7,10,10-tetramethyl-3-oxo-1H-benzo[8,8a][1]benzopyrano[2,3-e]isoindole (443) (6a R, 7S, 9a S, 12 R*, 13a S)-11-bromo-12-chloro-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (444) (6a R, 7S, 9a S, 11 R*, 12 R*, 13a S)-2, 3, 6, 6a, 7, 8, 9, 9a, 10, 11, 12, 13-dodecahydro-12-methoxy-6a,7,10,10-tetramethyl-3-oxo-5-trifluoromethyl-1H-benzo[8,8a][1]benzopyrano[2,3-e]isoindole (445) (1R*, 6a R, 7S, 9a S, 12 R*, 13a S)-12-amino-4-bromo-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (446) (1R*, 6a R, 7S, 9a S, 12 R*, 13a S)-4-bromo-2, 3, 6, 6a, 7, 8, 9, 9a, 10, 11, 12, 13-dodecahydro-12-methoxy-1-methoxyphenyl-6a,7,10,10-tetramethyl-3,11-dioxo-1H-benzo[8,8a][1]benzopyrano[2,3-e]isoindole (447) (6a R, 7S, 9a S, 11 R*, 12 R*, 13a S)-5-bromo-12-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (448) (6a R, 7S, 9a S, 11 R*, 12 R*, 13a S)-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (449) (1R*, 6a R, 7S, 9a S, 13a S)-2, 3, 6, 6a, 7, 8, 9, 9a, 10, 11, 12, 13-dodecahydro-1-methoxyphenyl-6a,7,10,10-tetramethyl-5-nitro-3,11-dioxo-1H-benzo[8,8a][1]benzopyrano[2,3-e]isoindole (450) (6a R, 7S, 9a S, 11 R*, 12 R*, 13a S)-12-amino-11-bromo-5-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (451) (6a R, 7S, 9a S, 11 R*, 12 R*, 13a S)-11-chloro-2, 3, 6, 6a, 7, 8, 9, 9a, 10, 11, 12, 13-dodecahydro-12-methoxy-6a,7,10,10-tetramethyl-4-nitro-3-oxo-1H-benzo[8,8a][1]benzopyrano[2,3-e]isoindole (452) (6a R, 7S, 9a S, 12 R*, 13a S)-5-carbamoyl-12-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (453) (6a R, 7S, 9a S, 11 R*, 12 R*, 13a S)-2, 3, 6, 6a, 7, 8, 9, 9a, 10, 11, 12, 13-dodecahydro-4,11,12-trihydroxy-6a,7,10,10-tetramethyl-3-oxo-1H-benzo[8,8a][1]benzopyrano[2,3-e]isoindole (454) (6a R, 7S, 9a S, 11 R*, 12 R*, 13a S)-4-carbamoyl-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (455) (6a R, 7S, 9a S, 11 R*, 12 R*, 13a S)-4,11-dichloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (456) (6a R, 7S, 9a S, 11 R*, 12 R*, 13a S)-11-bromo-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (457) (6a R, 7S, 9a S, 11 R*, 12 R*, 13a S)-12-amino-11-chloro-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (458) (6a R, 7S, 9a S, 11 R*, 12 R*, 13a S)-11-bromo-5-cyano-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (459) (6a R, 7S, 9a S, 11 R*, 12 R*, 13a S)-11-bromo-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (460) (6a R, 7S, 9a S, 11 R*, 12 R*, 13a S)-5-bromo-11-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (461) (6a R, 7S, 9a S, 11 R*, 12 R*, 13a S)-11-bromo-12-chloro-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (462) (6a R, 7S, 9a S, 11 R*, 12 R*, 13a S)-4-carboxy-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3-e]isoindole (463) (6a R, 7S, 9a S, 11 R*, 12 R*, 13a S)-12-bromo-4-carbamoyl-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (464) (1R*, 6a R, 7S, 9a S, 12 R*, 13a S)-2, 3, 6, 6a, 7, 8, 9, 9a, 10, 11, 12, 13-dodecahydro-12-hydroxy-1-methoxyphenyl-6a,7,10,10-tetramethyl-4-nitro-3,11-dioxo-1H-benzo[8,8a][1]benzopyrano[2,3-e]isoindole (465) (1R*, 6a R, 7S, 9a S, 12 R*, 13a S)-12-bromo-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (466) (1R*, 6a R, 7S, 9a S, 12 R*, 13a S)-12-acetylamino-4-chloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (467) (6a R, 7S, 9a S, 11 R*, 12 R*, 13a S)-11-bromo-2, 3, 6, 6a, 7, 8, 9, 9a, 10, 11, 12, 13-dodecahydro-12-methoxy-6a,7,10,10-tetramethyl-4-nitro-3-oxo-1H-benzo[8,8a][1]benzopyrano[2,3-e]isoindole (468) (6a R, 7S, 9a S, 11 R*, 12 R*, 13a S)-11-bromo-2, 3, 6, 6a, 7, 8, 9, 9a, 10, 11, 12, 13-dodecahydro-6a,7,10,10-tetramethyl-12-methylamino-3-oxo-5-trifluoromethyl-1H-benzo[8,8a][1]benzopyrano[2,3-e]isoindole (469) (6a R, 7S, 9a S, 12 R*, 13a S)-12-acetylamino-4-carboxy-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (470) (6a R, 7S, 9a S, 12 R*, 13a S)-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (471) (1R*, 6a R, 7S, 9a S, 13a S)-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (472) (6a R, 7S, 9a S, 12 R*, 13a S)-12-amino-5,11-dibromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (473) (6a R, 7S, 9a S, 11 R*, 12 R*, 13a S)-2, 3, 6, 6a, 7, 8, 9, 9a, 10, 11, 12, 13-dodecahydro-12-hydroxy-5-methoxycarbonyl-6a,7,10,10-tetramethyl-3-oxo-1H-benzo[8,8a][1]benzopyrano[2,3-e]isoindole (474) (6a R, 7S, 9a S, 11 R*, 12 R*, 13a S)-12-chloro-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (475) (6a R, 7S, 9a S, 11 R*, 12 R*, 13a S)-12-amino-2, 3, 6, 6a, 7, 8, 9, 9a, 10, 11, 12, 13-dodecahydro-11-hydroxy-6a,7,10,10-tetramethyl-3-oxo-5-trifluoromethyl-1H-benzo[8,8a][1]benzopyrano[2,3-e]isoindole (476) (6a R, 7S, 9a S, 11 R*, 12 R*, 13a S)-12-acetylamino-11-bromo-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (477) (1R*, 6a R, 7S, 9a S, 12 R*, 13a S)-12-amino-4-chloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (478) (1R*, 6a R, 7S, 9a S, 12 R*, 13a S)-11-bromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (479) (1R*, 6a R, 7S, 9a S, 12 R*, 13a S)-12-bromo-2, 3, 6, 6a, 7, 8, 9, 9a, 10, 11, 12, 13-dodecahydro-1-hydroxy-6a,7,10,10-tetramethyl-5-nitro-3,11-dioxo-1H-benzo[8,8a][1]benzopyrano[2,3-e]isoindole (480) (6a R, 7S, 9a S, 12 R*, 13a S)-2, 3, 6, 6a, 7, 8, 9, 9a, 10, 11, 12, 13-dodecahydro-6a,7,10,10-tetramethyl-4-nitro-3,11-dioxo-1H-benzo[8,8a][1]benzopyrano[2,3-e]isoindole (481) (6a R, 7S, 9a S, 12 R*, 13a S)-12-amino-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (482) (6a R, 7S, 9a S, 11 R*, 12 R*, 13a S)-11-bromo-2, 3, 6, 6a, 7, 8, 9, 9a, 10, 11, 12, 13-dodecahydro-12-methoxy-6a,7,10,10-tetramethyl-3-oxo-5-trifluoromethyl-1H-benzo[8,8a][1]benzopyrano[2,3-e]isoindole (483) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (484) (6a R, 7S, 9a S, 12 R*, 13a S)-4-bromo-12-chloro-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (485) (6a R, 7S, 9a S, 13a S)-5-cyano-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (486) (1R*, 6a R, 7S, 9a S, 12 R*, 13a S)-4,12-dichloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (487) (6a R, 7S, 9a S, 11 R*, 12 R*, 13a S)-4-bromo-11-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (488) (6a R, 7S, 9a S, 11 R*, 12 R*, 13a S)-5-bromo-12-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (489) (6a R, 7S, 9a S, 11 R*, 12 R*, 13a S)-4-cyano-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (490) (1R*, 6a R, 7S, 9a S, 12 R*, 13a S)-12-amino-2, 3, 6, 6a, 7, 8, 9, 9a, 10, 11, 12, 13-dodecahydro-1-hydroxyphenyl-6a,7,10,10-tetramethyl-4-nitro-3,11-dioxo-1H-benzo[8,8a][1]benzopyrano[2,3-e]isoindole (491) (1R*, 6a R, 7S, 9a S, 12 R*, 13a S)-4-carboxy-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (492) (6a R, 7S, 9a S, 11 R*, 12 R*, 13a S)-4-carbamoyl-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (493) (6a R, 7S, 9a S, 11 R*, 12 R*, 13a S)-12-acetylamino-11-chloro-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (494) (6a R, 7S, 9a S, 12 R*, 13a S)-5-chloro-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (495) (6a R, 7S, 9a S, 12 R*, 13a S)-12-amino-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (496) (6a R, 7S, 9a S, 11 R*, 12 R*, 13a S)-11,12-dichloro-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole (497) (6a R, 7S, 9a S, 11 R*, 12 R*, 13a S)-5-bromo-11-chloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (498) (6a R, 7S, 9a S, 11 R*, 12 R*, 13a S)-12-bromo-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (499) (6a R, 7S, 9a S, 12 R*, 13a S)-12-amino-2, 3, 6, 6a, 7, 8, 9, 9a, 10, 11, 12, 13-dodecahydro-6a,7,10,10-tetramethyl-4-nitro-3,11-dioxo-1H-benzo[8,8a][1]benzopyrano[2,3-e]isoindole (500) (6a R, 7S, 9a S, 12 R*, 13a S)-4-cyano-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (501) (6a R, 7S, 9a S, 11 R*, 12 R*, 13a S)-12-acetylamino-2, 3, 6, 6a, 7, 8, 9, 9a, 10, 11, 12, 13-dodecahydro-11-hydroxy-5-methoxycarbonyl-6a,7,10,10-tetramethyl-3-oxo-1H-benzo[8,8a][1]benzopyrano[2,3-e]isoindole (502) (1R*, 6a R, 7S, 9a S, 12 R*, 13a S)-4-bromo-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (503) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (504) (6a R, 7S, 9a S, 11 R*, 12 R*, 13a S)-12-acetylamino-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (505) (6a R, 7S, 9a S, 11 R*, 12 R*, 13a S)-5-chloro-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3-e]isoindole (506) (1R*, 6a R, 7S, 9a S, 12 R*, 13a S)-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (507) (6a R, 7S, 9a S, 11 R*, 12 R*, 13a S)-11-bromo-12-chloro-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (508) (6a R, 7S, 9a S, 11 R*, 12 R*, 13a S)-5-chloro-11, 12-epoxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (509) (6a R, 7S, 9a S, 11 R*, 12 R*, 13a S)-11-chloro-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (510) (6a R, 7S, 9a S, 12 R*, 13a S)-2, 3, 6, 6a, 7, 8, 9, 9a, 10, 11, 12, 13-dodecahydro-4hydroxy-6a,7,10,10-tetramethyl-12-methylamino-3,11-dioxo-1H-benzo[8,8a][1]benzopyrano[2,3-e]isoindole (511) (6a R, 7S, 9a S, 12 R*, 13a S)-12-acetylamino-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (512) (6a R, 7S, 9a S, 12 R*, 13a S)-11-bromo-5-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (513) (6a R, 7S, 9a S, 11 R*, 12 R*, 13a S)-12-acetylamino-5-bromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (514) (6a R, 7S, 9a S, 11 R*, 12 R*, 13a S)-11-bromo-4-cyano-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (515) (6a R, 7S, 9a S, 11 R*, 12 R*, 13a S)-4-bromo-12-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (516) (6a R, 7S, 9a S, 11 R*, 12 R*, 13a S)-4-cyano-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3-e]isoindole (517) (6a R, 7S, 9a S, 11 R*, 12 R*, 13a S)-11-bromo-5-carboxy-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (518) (1R*, 6a R, 7S, 9a S, 12 R*, 13a S)-2, 3, 6, 6a, 7, 8, 9, 9a, 10, 11, 12, 13-dodecahydro-12-hydroxy-1-methoxy-6a,7,10,10-tetramethyl-3,11-dioxo-1H-benzo[8,8a][1]benzopyrano[2,3-e]isoindole (519) (6a R, 7S, 9a S, 11 R*, 12 R*, 13a S)-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (520) (6a R, 7S, 9a S, 11 R*, 12 R*, 13a S)-5-carbamoyl-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (521) (6a R, 7S, 9a S, 11 R*, 12 R*, 13a S)-12-bromo-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (522) (6a R, 7S, 9a S, 12 R*, 13a S)-12-chloro-2, 3, 6, 6a, 7, 8, 9, 9a, 10, 11, 12, 13-dodecahydro-4-hydroxy-6a,7,10,10-tetramethyl-3,11-dioxo-1H-benzo[8,8a][1]benzopyrano[2,3-e]isoindole (523) (6a R, 7S, 9a S, 12 R*, 13a S)-12-amino-5-carbamoyl-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (524) (1R*, 6a R, 7S, 9a S, 12 R*, 13a S)-4,12-dibromo-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (525) (6a R, 7S, 9a S, 11 R*, 12 R*, 13a S)-12-bromo-11-chloro-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (526) (1R*, 6a R, 7S, 9a S, 13a S)-5-bromo-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (527) (1R*, 6a R, 7S, 9a S, 12 R*, 13a S)-5,12-dichloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (528) (1R*, 6a R, 7S, 9a S, R*, 12 R*, 13a S)-12-acetylamino-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (529) (1R*, 6a R, 7S, 9a S, 12 R*, 13a S)-5-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (530) (1R*, 6a R, 7S, 9a S, 12 R*, 13a S)-4,12-dibromo-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (531) (6a R, 7S, 9a S, 11 R*, 12 R*, 13a S)-4-carboxy-11-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (532) (6a R, 7S, 9a S, 11 R*, 12 R*, 13a S)-5-chloro-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (533) (6a R, 7S, 9a S, 11 R*, 12 R*, 13a S)-11-chloro-4-cyano-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (534) (6a R, 7S, 9a S, 11 R*, 12 R*, 13a S)-5,11-dibromo-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (535) (6a R, 7S, 9a S, 12 R*, 13a S)-12-amino-2, 3, 6, 6a, 7, 8, 9, 9a, 10, 11, 12, 13-dodecahydro-4-methoxy-6a,7,10,10-tetramethyl-3,11-dioxo-1H-benzo[8,8a][1]benzopyrano[2,3-e]isoindole (536) (6a R, 7S, 9a S, 11 R*, 12 R*, 13a S)-11,12-dichloro-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (537) (6a R, 7S, 9a S, 12 R*, 13a S)-12-amino-5-bromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (538) (6a R, 7S, 9a S, 11 R*, 12 R*, 13a S)-12-acetylamino-4-carbamoyl-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (539) (6a R, 7S, 9a S, 11 R*, 12 R*, 13a S)-12-amino-5-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (540) (6a R, 7S, 9a S, 11 R*, 12 R*, 13a S)-12-amino-4-bromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (541) (6a R, 7S, 9a S, 12 R*, 13a S)-2, 3, 6, 6a, 7, 8, 9, 9a, 10, 11, 12, 13-dodecahydro-6a,7,10,10-tetramethyl-12-methylamino-3,11-dioxo-4-trifluoromethyl-1H-benzo[8,8a][1]benzopyrano[2,3-e]isoindole (542) (6a R, 7S, 9a S, 12 R*, 13a S)-12-acetylamino-5-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (543) (6a R, 7S, 9a S, 12 R*, 13a S)-2, 3, 6, 6a, 7, 8, 9, 9a, 10, 11, 12, 13-dodecahydro-4,12-dihydroxy-6a,7,10,10-tetramethyl-3-oxo-1H-benzo[8,8a][1]benzopyrano[2,3-e]isoindole (544) (1R*, 6a R, 7S, 9a S, 12 R*, 13a S)-12-amino-5-bromo-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (545) (6a R, 7S, 9a S, 11 R*, 12 R*, 13a S)-5-carboxy-12-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (546) (6a R, 7S, 9a S, 11 R*, 12 R*, 13a S)-12-bromo-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (547) (6a R, 7S, 9a S, 11 R*, 12 R*, 13a S)-5-carboxy-11-chloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (548) (1R*, 6a R, 7S, 9a S, 12 R*, 13a S)-4-bromo-2, 3, 6, 6a, 7, 8, 9, 9a, 10, 11, 12, 13-dodecahydro-1-methoxy-6a,7,10,10-tetramethyl-12-methylamino-3,11-dioxo-1H-benzo[8,8a][1]benzopyrano[2,3-e]isoindole (549) (6a R, 7S, 9a S, 11 R*, 12 R*, 13a S)-12-bromo-11-chloro-2, 3, 6, 6a, 7, 8, 9, 9a, 10, 11, 12, 13-dodecahydro-4-methoxycarbonyl-6a,7,10,10-tetramethyl-12-methylamino-3-oxo-1H-benzo[8,8a][1]benzopyrano[2,3-e]isoindole (550) (6a R, 7S, 9a S, 11 R*, 12 R*, 13a S)-12-bromo-2, 3, 6, 6a, 7, 8, 9, 9a, 10, 11, 12, 13-dodecahydro-4-methoxycarbonyl-6a,7,10,10-tetramethyl-3-oxo-1H-benzo[8,8a][1]benzopyrano[2,3-e]isoindole (551) (1R*, 6a R, 7S, 9a S, 12 R*, 13a S)-12-amino-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (552) (6a R, 7S, 9a S, 11 R*, 12 R*, 13a S)-11-chloro-4-cyano-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (553) (6a R, 7S, 9a S, 12 R*, 13a S)-11-chloro-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (554) (6a R, 7S, 9a S, 11 R*, 12 R*, 13a S)-5-bromo-11, 12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (555) (1R*, 6a R, 7S, 9a S, 12 R*, 13a S)-12-amino-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (556) (6a R, 7S, 9a S, 11 R*, 12 R*, 13a S)-12-amino-11-bromo-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (557) (6a R, 7S, 9a S, 11 R*, 12 R*, 13a S)-2, 3, 6, 6a, 7, 8, 9, 9a, 10, 11, 12, 13-dodecahydro-11-hydroxy-6a,7,10,10-tetramethyl-12-methylamino-4-nitro-3-oxo-1H-benzo[8,8a][1]benzopyrano[2,3-e]isoindole (558) (6a R, 7S, 9a S, 11 R*, 12 R*, 13a S)-12-acetylamino-5-carbamoyl-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (559) (6a R, 7S, 9a S, 12 R*, 13a S)-11-hydroxy-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (560) (6a R, 7S, 9a S, 11 R*, 12 R*, 13a S)-12-bromo-4-carbamoyl-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (561) (6a R, 7S, 9a S, 12 R*, 13a S)-4-cyano-2, 3, 6, 6a, 7, 8, 9, 9a, 10, 11, 12, 13-dodecahydro-11,12-dihydroxy-6a,7,10,10-tetramethyl-3-oxo-1H-benzo[8,8a][1]benzopyrano[2,3-e]isoindole (562) (6a R, 7S, 9a S, 11 R*, 12 R*, 13a S)-11-bromo-5-cyano-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (563) (6a R, 7S, 9a S, 11 R*, 12 R*, 13a S)-12-amino-5-carboxy-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (564) (6a R, 7S, 9a S, 11 R*, 12 R*, 13a S)-12-acetylamino-2, 3, 6, 6a, 7, 8, 9, 9a, 10, 11, 12, 13-dodecahydro-11-hydroxy-6a,7,10,10-tetramethyl-5-nitro-3-oxo-1H-benzo[8,8a][1]benzopyrano[2,3-e]isoindole (565) (6a R, 7S, 9a S, 12 R*, 13a S)-12-bromo-5-carbamoyl-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (566) (6a R, 7S, 9a S, 11 R*, 12 R*, 13a S)-4-bromo-11-chloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (567) (1R*, 6a R, 7S, 9a S, 12 R*, 13a S)-2, 3, 6, 6a, 7, 8, 9, 9a, 10, 11, 12, 13-dodecahydro-6a,7,10,10-tetramethyl-12-methylamino-5-nitro-3,11-dioxo-1H-benzo[8,8a][1]benzopyrano[2,3-e]isoindole (568) (1R*, 6a R, 7S, 9a S, 12 R*, 13a S)-12-chloro-2, 3, 6, 6a, 7, 8, 9, 9a, 10, 11, 12, 13-dodecahydro-1-methoxy-6a,7,10,10-tetramethyl-5-nitro-3,11-dioxo-1H-benzo[8,8a][1]benzopyrano[2,3-e]isoindole (569) (1R*, 6a R, 7S, 9a S, 13a S)-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (570) (6a R, 7S, 9a S, 11 R*, 12 R*, 13a S)-12-acetylamino-11-chloro-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (571) (6a R, 7S, 9a S, 12 R*, 13a S)-12-acetylamino-5-bromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (572) (6a R, 7S, 9a S, 11 R*, 12 R*, 13a S)-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (573) (6a R, 7S, 9a S, 11 R*, 12 R*, 13a S)-4-bromo-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (574) (1R*, 6a R, 7S, 9a S, 12 R*, 13a S)-12-bromo-2, 3, 6, 6a, 7, 8, 9, 9a, 10, 11, 12, 13-dodecahydro-1-methoxyphenyl-6a,7,10,10-tetramethyl-4-nitro-3,11-oxo-1H-benzo[8,8a][1]benzopyrano[2,3-e]isoindole (575) (6a R, 7S, 9a S, 11 R*, 12 R*, 13a S)-12-acetylamino-11-bromo-2, 3, 6, 6a, 7, 8, 9, 9a, 10, 11, 12, 13-dodecahydro-5-methoxycarbonyl-6a,7,10,10-tetramethyl-3-oxo-1H-benzo[8,8a][1]benzopyrano[2,3-e]isoindole (576) (6a R, 7S, 9a S, 12 R*, 13a S)-5,11,12-trichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (577) (6a R, 7S, 9a S, 11 R*, 12 R*, 13a S)-4-bromo-12-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (578) (6a R, 7S, 9a S, 11 R*, 12 R*, 13a S)-4-cyano-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (579) (6a R, 7S, 9a S, 11 R*, 12 R*, 13a S)-2, 3, 6, 6a, 7, 8, 9, 9a, 10, 11, 12, 13-dodecahydro-11-hydroxy-6a,7,10,10-tetramethyl-12-methylamino-3-oxo-5-trifluoromethyl-1H-benzo[8,8a][1]benzopyrano[2,3-e]isoindole (580) (1R*, 6a R, 7S, 9a S, 12 R*, 13a S)-12-amino-4-chloro-2, 3, 6, 6a, 7, 8, 9, 9a, 10, 11, 12, 13-dodecahydro-1-hydroxyphenyl-6a,7,10,10-tetramethyl-3,11-1H-benzo[8,8a][1]benzopyrano[2,3-e]isoindole (581) (6a R, 7S, 9a S, 11 R*, 12 R*, 13a S)-2, 3, 6, 6a, 7, 8, 9, 9a, 10, 11, 12, 13-dodecahydro-11-hydroxy-6a,7,10,10-tetramethyl-12-methylamino-5-nitro-3-oxo-5-trifluoromethyl-1H-benzo[8,8a][1]benzopyrano[2,3-e]isoindole (582) (6a R, 7S, 9a S, 11 R*, 12 R*, 13a S)-11-bromo-5-carbamoyl-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (583) (6a R, 7S, 9a S, 11 R*, 12 R*, 13a S)-12-amino-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (584) (6a R, 7S, 9a S, 11 R*, 12 R*, 13a S)-12-bromo-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (585) (6a R, 7S, 9a S, 11 R*, 12 R*, 13a S)-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (586) (6a R, 7S, 9a S, 11 R*, 12 R*, 13a S)-12-amino-4-cyano-2, 3, 6, 6a, 7, 8, 9, 9a, 10, 11, 12, 13-dodecahydro-6a,7,10,10-tetramethyl-3-oxo-5-trifluoromethyl-1H-benzo[8,8a][1]benzopyrano[2,3-e]isoindole (587) (6a R, 7S, 9a S, 11 R*, 12 R*, 13a S)-11-chloro-2, 3, 6, 6a, 7, 8, 9, 9a, 10, 11, 12, 13-dodecahydro-12-hydroxy-5-methoxycarbonyl-6a,7,10,10-tetramethyl-3-oxo-1H-benzo[8,8a][1]benzopyrano[2,3-e]isoindole (588) (6a R, 7S, 9a S, 11 R*, 12 R*, 13a S)-12-acetylamino-11-bromo-5-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (589) (6a R, 7S, 9a S, 11 R*, 12 R*, 13a S)-12-acetylamino-4-cyano-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (590) (6a R, 7S, 9a S, 12 R*, 13a S)-12-chloro-2, 3, 6, 6a, 7, 8, 9, 9a, 10, 11, 12, 13-dodecahydro-5-methoxycarbonyl-6a,7,10,10-tetramethyl-3,11-dioxo-1H-benzo[8,8a][1]benzopyrano[2,3-e]isoindole (591) (6a R, 7S, 9a S, 11 R*, 12 R*, 13a S)-5-cyano-2, 3, 6, 6a, 7, 8, 9, 9a, 10, 11, 12, 13-dodecahydro-11,12-dihydroxy-6a,7,10,10-tetramethyl-3-oxo-1H-benzo[8,8a][1]benzopyrano[2,3-e]isoindole (592) (6a R, 7S, 9a S, 11 R*, 12 R*, 13a S)-5-cyano-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (593) (1R*, 6a R, 7S, 9a S, 12 R*, 13a S)-12-chloro-2, 3, 6, 6a, 7, 8, 9, 9a, 10, 11, 12, 13-dodecahydro-1-hydroxyphenyl-6a,7,10,10-tetramethyl-5-nitro-3,11-dioxo-1H-benzo[8,8a][1]benzopyrano[2,3-e]isoindole (594) (6a R, 7S, 9a S, 12 R*, 13a S)-4-carbamoyl-2, 3, 6, 6a, 7, 8, 9, 9a, 10, 11, 12, 13-dodecahydro-12-methoxy-6a,7,10,10-tetramethyl-3,11-dioxo-1H-benzo[8,8a][1]benzopyrano[2,3-e]isoindole (595) (6a R, 7S, 9a S, 11 R*, 12 R*, 13a S)-11-bromo-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (596) (6a R, 7S, 9a S, 11 R*, 12 R*, 13a S)-12-acetylamino-2, 3, 6, 6a, 7, 8, 9, 9a, 10, 11, 12, 13-dodecahydro-11-hydroxy-6a,7,10,10-tetramethyl-4-nitro-3-oxo-1H-benzo[8,8a][1]benzopyrano[2,3-e]isoindole (597) (6a R, 7S, 9a S, 12 R*, 13a S)-12-acetylamino-11-chloro-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (598) (6a R, 7S, 9a S, 12 R*, 13a S)-12-bromo-4-carbamoyl-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (599) (6a R, 7S, 9a S, 11 R*, 12 R*, 13a S)-11-bromo-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (600) (6a R, 7S, 9a S, 11 R*, 12 R*, 13a S)-11-bromo-5-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (601) (6a R, 7S, 9a S, 12 R*, 13a S)-12-chloro-2, 3, 6, 6a, 7, 8, 9, 9a, 10, 11, 12, 13-dodecahydro-6a,7,10,10-tetramethyl-5-nitro-3,11-dioxo-1H-benzo[8,8a][1]benzopyrano[2,3-e]isoindole (602) (6a R, 7S, 9a S, 12 R*, 13a S)-5-carboxy-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (603) (6a R, 7S, 9a S, 12 R*, 13a S)-5,11-dibromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (604) (6a R, 7S, 9a S, 12 R*, 13a S)-4-carboxy-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (605) (6a R, 7S, 9a S, 11 R*, 12 R*, 13a S)-4,11-dibromo-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (606) (6a R, 7S, 9a S, 11 R*, 12 R*, 13a S)-12-amino-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (607) (1R*, 6a R, 7S, 9a S, 12 R*, 13a S)-4-dibromo-12-chloro-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (608) (6a R, 7S, 9a S, 11R*, 12 R*, 13a S)-11-chloro-2, 3, 6, 6a, 7, 8, 9, 9a, 10, 11, 12, 13-dodecahydro-4-hydroxy-6a,7,10,10-tetramethyl-12-methylamino-3-oxo-1H-benzo[8,8a][1]benzopyrano[2,3-e]isoindole (609) (1R*, 6a R, 7S, 9a S, 12 R*, 13a S)-12-amino-2, 3, 6, 6a, 7, 8, 9, 9a, 10, 11, 12, 13-dodecahydro-1-hydroxy-6a,7,10,10-tetramethyl-5-nitro-3,11-dioxo-1H-benzo[8,8a][1]benzopyrano[2,3-e]isoindole (610) (1R*, 6a R, 7S, 9a S, 12 R*, 13a S)-4-bromo-12-chloro-2, 3, 6, 6a, 7, 8, 9, 9a, 10, 11, 12, 13-dodecahydro- 1-hydroxy-6a,7,10,10-tetramethyl-3,11-dioxo-1H-benzo[8,8a][1]benzopyrano[2,3-e]isoindole (611) (6a R, 7S, 9a S, 11 R*, 12 R*, 13a S)-12-acetylamino-4-bromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (612) (6a R, 7S, 9a S, 11 R*, 12 R*, 13a S)-12-amino-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (613) (6a R, 7S, 9a S, 11 R*, 12 R*, 13a S)-12-chloro-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (614) (6a R, 7S, 9a S, 11 R*, 12 R*, 13a S)-2, 3, 6, 6a, 7, 8, 9, 9a, 10, 11, 12, 13-dodecahydro-11,12-dihydroxy-5-methoxycarbonyl-6a,7,10,10-tetramethyl-3-oxo-1H-benzo[8,8a][1]benzopyrano[2,3-e]isoindole (615) (6a R, 7S, 9a S, 12 R*, 13a S)-12-acetylamino-2, 3, 6, 6a, 7, 8, 9, 9a, 10, 11, 12, 13-dodecahydro-4-methoxy-6a,7,10,10-tetramethyl-3,11-dioxo-1H-benzo[8,8a][1]benzopyrano[2,3-e]isoindole (616) (6a R, 7S, 9a S, 11 R*, 12 R*, 13a S)-4-chloro-2, 3, 6, 6a, 7, 8, 9, 9a, 10, 11, 12, 13-dodecahydro-11-hydroxy-12-methoxy-6a,7,10,10-tetramethyl-3-oxo-1H-benzo[8,8a][1]benzopyrano[2,3-e]isoindole (617) (6a R, 7S, 9a S, 11 R*, 12 R*, 13a S)-11-dibromo-4-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (618) (1R*, 6a R, 7S, 9a S, 12 R*, 13a S)-5,12-dibromo-4-bromo-2, 3, 6, 6a, 7, 8, 9, 9a, 10, 11, 12, 13-dodecahydro-1,12-dimethoxy-6a,7,10,10-tetramethyl-3,11-dioxo-1H-benzo[8,8a][1]benzopyrano[2,3-e]isoindole (619) (6a R, 7S, 9a S, 11 R*, 12 R*, 13a S)-12-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3- e]isoindole (620) (6a R,7S,9a S,11R*,12R*,13aS)-11-hydroxy-2,3,6,6a,7,8,9,9a,10,11,12,13-dodecahydro-4-methoxycarbonyl-6a,7,10,10-tetramethyl-3-oxo-1H-benzo[8,8a][1]benzopyrano[2,3-e]isoindole (621) (6aR,7S,9aS,11R*,12R*,13aS)-11-bromo-2,3,6,6a,7,8,9,9a,10,11,12,13-dodecahydro-12-methoxy-5-methoxycarbonyl-6a,7,10,10-tetramethyl-3-oxo-1H-benzo[8,8a][1]benzopyrano[2,3-e]isoindole (622) (1R*,6aR,7S,9aS,13aS)-2,3,6,6a,7,8,9,9a,10,11,12,13-dodecahydro-1-hydroxy-6a,7,10,10-tetramethyl-3,11-dioxo-1H-benzo[8,8a][1]benzopyrano[2,3-e]isoindole (623) (6aR,7S,9aS,12R*,13aS)-12-chloro-2,3,6,6a,7,8,9,9a,10,11,12,13-dodecahydro-6a,7,10,10-tetramethyl-4-nitro-3,11-dioxo-1H-benzo[8,8a][1]benzopyrano[2,3-e]isoindole (624) (6aR,7S,9aS,12R*,13aS)-12-bromo2,3,6,6a,7,8,9,9a,10,11,12,13-dodecahydro-6a,7,10,10-tetramethyl-3-oxo-5-trifluoromethyl-1H-benzo[8,8a][1]benzopyrano[2,3-e]isoindole (625) (1R*,6aR,7S,9aS,12R*,13aS)-5-chloro-2,3,6,6a,7,8,9,9a,10,11,12,13-dodecahydro-1,12-dihydroxy-6a,7,10,10-tetramethyl-3,11-dioxo-1H-benzo[8,8a][1]benzopyrano[2,3-e]isoindole (626) (6aR,7S,9aS,11R*,12*R,13aS)-12-amino-4bromo-11-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (627) (6aR,7S,9aS,12R*,13aS)-12-amino-2,3,6,6a,7,8,9,9a,10,11,12,13-dodecahydro-6a,7,10,10-tetramethyl-3,11-dioxo-5-trifluoromethyl-1H-benzo[8,8a][1]benzopyrano[2,3-e]isoindole (628) (6aR,7S,9aS,11R*,12R*,13aS)-11-bromo-2,3,6,6a,7,8,9,9a,10,11,12,13-dodecahydro-12-hydroxy-6a,7,10,10-tetramethyl-3-oxo-5-trifluoromethyl-1H-benzo[8,8a][1]benzopyrano[2,3-e]isoindole (629) (1R*,6aR,7S,9aS,12R*,13aS)-12-amino-4-chloro-2,3,6,6a,7,8,9,9a,10,11,12,13-dodecahydro-1-methoxyphenyl-6a,7,10,10-tetramethyl-3,11-dioxo-1H-benzo[8,8a][1]benzopyrano[2,3-e]isoindole (630) (1R*,6aR,7S,9aS,13aS)-2,3,6,6a,7,8,9,9a,10,11,12,13-dodecahydro-1-methoxyphenyl-6a,7,10,10-tetramethyl-4-nitro-3,11-dioxo-1H-benzo[8,8a][1]benzopyrano[2,3-e]isoindole (631) (1R*,6aR,7S,9aS,13aS)-2,3,6,6a,7,8,9,9a,10,11,12,13-dodecahydro-12-hydroxy-6a,7,10,10-tetramethyl-3-oxo-4-trifluoromethyl-1H-benzo[8,8a][1]benzopyrano[2,3-e]isoindole (632) (1R*,6aR,7S,9aS,13aS)-12-bromo-5-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (633) (6aR,7S,9aS,11R*,12R*,13aS)-12-bromo-4-cyano-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (634) (6aR,7S,9aS,11R*,12R*,13aS)-4-chloro-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (635) (6aR,7S,9aS,12R*,13aS)-4-carbamoyl-2,3,6,6a,7,8,9,9a,10,11,12,13-dodecahydro-12-hydroxy-6a,7,10,10-tetramethyl-3,11-dioxo-1H-benzo[8,8a][1]benzopyrano[2,3-e]isoindole (636) (6aR,7S,9aS,11R*,12R*,13aS)-11-bromo-5-chloro-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (637) (6aR,7S,9aS,11R*,12R*,13aS)-11,12-dichloro-2,3,6,6a,7,8,9,9a,10,11,12,13-dodecahydro-4-methoxy-6a,7,10,10-tetramethyl-3-oxo-1H-benzo[8,8a][1]benzopyrano[2,3-e]isoindole (638) (6aR,7S,9aS,11R*,12R*,13aS)-11-chloro-2,3,6,6a,7,8,9,9a,10,11,12,13-dodecahydro-4,12-dihydroxy-6a,7,10,10-tetramethyl-3-oxo-1H-benzo[8,8a][1]benzopyrano[2,3-e]isoindole (639) (6aR,7S,9aS,11R*,12R*,13aS)-12-amino-4-carbamoyl-11-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (640) (6aR,7S,9aS,11R*,12R*,13aS)-11-bromo-12-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (641) (6aR,7S,9aS,11R*,12R*,13aS)-12-acetylamino-4,11-dibromo-4-cyano-2,3,6,6a,7,8,9,9a,10,11,12,13-dodecahydro-6a,7,10,10-tetramethyl-3-oxo-1H-benzo[8,8a][1]benzopyrano[2,3-e]isoindole (642) (6aR,7S,9aS,11R*,12R*,13aS)-12-acetylamino-5-carboxy-11-chloro-2,3,6,6a, 7,8,9,9a,10,11,12,13-dodecahydro-6a,7,10,10-tetramethyl-3-oxo-1H-benzo[8,8a][1]benzopyrano[2,3-e]isoindole (643) (6aR,7S,9aS,11R*,12R*,13aS)-11-bromo-2,3,6,6a,7,8,9,9a,10,11,12,13-dodecahydro-6a,7,10,10-tetramethyl-5-nitro-3-oxo-1H-benzo[8,8a][1]benzopyrano[2,3-e]isoindole (644) (6aR,7S,9aS,11R*,12R*,13aS)-11-bromo-12-chloro-2,3,6,6a,7,8,9,9a,10,11,12,13-dodecahydro-4- methoxycarbonyl-6a,7,10,10-tetramethyl-3-oxo-1H-benzo[8,8a][1]benzopyrano[2,3-e]isoindole (645) (1R*,6aR,7S,9aS,12R*,13aS)-4-bromo-2,3,6,6a,7,8,9,9a,10,11,12,13-dodecahydro-12-hydroxy-1-methoxy-6a,7,10,10-tetramethyl-3,11-dioxo-1H-benzo[8,8a][1]benzopyrano[2,3-e]isoindole (646) (6aR,7S,9aS,12R*,13aS)-12-bromo-4-carboxy-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (647) (6aR,7S,9aS,12R*,13aS)-2,3,6,6a,7,8,9,9a,10,11,12,13-dodecahydro-12-hydroxy-6a,7,10,10-tetramethyl-4-nitro-3-oxo-1H-benzo[8,8a][1]benzopyrano[2,3-e]isoindole (648) (6aR,7S,9aS,11R*,12R*,13aS)-12-acetylamino-5,11-dichloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (649) (6aR,7S,9aS,11R*,12R*,13aS)-11-bromo-4-cyano-2,3,6,6a,7,8,9,9a,10,11,12,13-dodecahydro-12-methoxy-6a,7,10,10-tetramethyl-3-oxo-1H-benzo[8,8a][1]benzopyrano[2,3-e]isoindole (650) (1R*,6aR,7S,9aS,12R*,13aS)-2,3,6,6a,7,8,9,9a,10,11,12,13-dodecahydro-1-hydroxyphenyl-6a,7,10,10-tetramethyl-12-methylamino-3,11-dioxo-1H-benzo[8,8a][1]benzopyrano[2,3-e]isoindole (651) (6aR,7S,9aS,11R*,12R*,13aS)-2,3,6,6a,7,8,9,9a,10,11,12,13-dodecahydro-6a,7,10,10-tetramethyl-4-nitro-3-oxo-1H-benzo[8,8a][1]benzopyrano[2,3-e]isoindole (652) (6aR,7S,9aS,11R*,12R*,13aS)-4-bromo-11-chloro-2,3,6,6a,7,8,9,9a,10,11,12,13-dodecahydro-12-methoxy-6a,7,10,10-tetramethyl-3-oxo-1H-benzo[8,8a][1]benzopyrano[2,3-e]isoindole (653) (1R*,6aR,7S,9aS,12R*,13aS)-12-amino-2,3,6,6a,7,8,9,9a,10,11,12,13-dodecahydro-1-methoxyphenyl-6a,7,10,10-tetramethyl-4-nitro-3,11-dioxo-1H-benzo[8,8a][1]benzopyrano[2,3-e]isoindole (654) (6aR,7S,9aS,11R*,12R*,13aS)-12-bromo-2,3,6,6a,7,8,9,9a,10,11,12,13-dodecahydro-11-hydroxy-6a,7,10,10-tetramethyl-3-oxo-5-trifluoromethyl-1H-benzo[8,8a][1]benzopyrano[2,3-e]isoindole (655) (6aR,7S,9aS,11R*,12R*,13aS)-12-amino-11-bromo-5-cyano-2,3,6,6a,7,8,9,9a,10,11,12,13-dodecahydro-6a,7,10,10-tetramethyl-3-oxo-1H-benzo[8,8a][1]benzopyrano[2,3-e]isoindole (656) (1R*,6aR,7S,9aS,12R*,13aS)-12-amino-5-chloro-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole (657) (1R*,6aR,7S,9aS,12R*,13aS)-12-bromo-4-chloro-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole (658) (1R*,6aR,7S,9aS,12R*,13aS)-5,12-dibromo-2,3,6,6a,7,8,9,9a,10,11,12,13-dodecahydro-1-methoxyphenyl-6a,7,10,10-tetramethyl-3,11-dioxo-1H-benzo[8,8a][1]benzopyrano[2,3-e]isoindole (659) (6aR,7S,9aS,11R*,12R*,13aS)-12-amino-11-bromo-2,3,6,6a,7,8,9,9a,10,11,12,13-dodecahydro-4-hydroxy-6a,7,10,10-tetramethyl-3-oxo-1H-benzo[8,8a][1]benzopyrano[2,3-e]isoindole (660) (6aR,7S,9aS,11R*,12R*,13aS)-11,12-epoxy-2,3,6,6a,7,8,9,9a,10,11,12,13-dodecahydro-4-hydroxy-6a,7,10,10-tetramethyl-3-oxo-1H-benzo[8,8a][1]benzopyrano[2,3-e]isoindole (661) (6aR,7S,9aS,11R*,12R*,13aS)-12-chloro-4-cyano-2,3,6,6a,7,8,9,9a,10,11,12,13-dodecahydro-11-hydroxy-7,10,10-tetramethyl-3-oxo-1H-benzo[8,8a][1]benzopyrano[2,3-e]isoindole (662) (6aR,7S,9aS,11R*,12R*,13aS)-4,11-dibromo-2,3,6,6a,7,8,9,9a,10,11,12,13-dodecahydro-6a,7,10,10-tetramethyl-12-methylamino-3-oxo-1H-benzo[8,8a][1]benzopyrano[2,3-e]isoindole (663) (6aR,7S,9aS,11R*,12R*,13aS)-5,11-dichloro-2,3,6,6a,7,8,9,9a,10,11,12,13-dodecahydro-6a,7,10,10-tetramethyl-12-methylamino-3-oxo-1H-benzo[8,8a][1]benzopyrano[2,3-e]isoindole (664) (1R*,6aR,7S,9aS,12R*,13aS)-12-acetylamino-5-bromo-2,3,6,6a,7,8,9,9a,10,11,12,13-dodecahydro-1-methoxy-6a,7,10,10-tetramethyl-3,11-dioxo-1H-benzo[8,8a][1]benzopyrano[2,3-e]isoindole (665) (1R*,6aR,7S,9aS,12R*,13aS)-12-amino-5-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (666) (6aR,7S,9aS,13aS)-4-carboxy-2,3,6,6a,7,8,9,9a,10,11,12,13-dodecahydro-6a,7,10,10-tetramethyl-3-oxo-1H-benzo[8,8a][1]benzopyrano[2,3-e]isoindole (667) (1R*,6aR,7S,9aS,12R*,13aS)-5-chloro-2,3,6,6a,7,8,9,9a,10,11,12,13-dodecahydro-12-methoxy-1-methoxyphenyl-6a,7,10,10-tetramethyl-3,11-dioxo-1H-benzo[8,8a][1]benzopyrano[2,3-e]isoindole (668) (6aR,7S,9aS,11R*,12R*,13aS)-12-amino-4,11-dichloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (669) (6aR,7S,9aS,11R*,12R*,13aS)-11-chloro-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (670) (6aR,7S,9aS,11R*,12R*,13aS)-12-bromo-4-chloro-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (671) (1R*,6aR,7S,9aS,12R*,13aS)-2,3,6,6a,7,8,9,9a,10,11,12,13-dodecahydro-12-hydroxy-1-hydroxyphenyl-6a,7,10,10-tetramethyl-5-nitro-3,11-dioxo-1H-benzo[8,8a][1]benzopyrano[2,3-e]isoindole (672) (1R*,6aR,7S,9aS,12R*,13aS)-2,3,6,6a,7,8,9,9a,10,11,12,13-dodecahydro-12-methoxy-5-methoxycarbonyl-6a,7,10,10-tetramethyl-3-oxo-1H-benzo[8,8a][1]benzopyrano[2,3-e]isoindole (673) (6aR,7S,9aS,11R*,12R*,13aS)-4,11-dibromo-2,3,6,6a,7,8,9,9a,10,11,12,13-dodecahydro-12-methoxy-6a,7,10,10-tetramethyl-3-oxo-1H-benzo[8,8a][1]benzopyrano[2,3-e]isoindole (674) (6aR,7S,9aS,12R*,13aS)-2,3,6,6a,7,8,9,9a,10,11,12,13-dodecahydro-6a,7,10,10-tetramethyl-12-methylamino-3,11-dioxo-5-trifluoromethyl-1H-benzo[8,8a][1]benzopyrano[2,3-e]isoindole (675) (6aR,7S,9aS,11R*,12R*,13aS)-2,3,6,6a,7,8,9,9a,10,11,12,13-dodecahydro-11,12-dihydroxy-4-methoxy-6a,7,10,10-tetramethyl-3-oxo-1H-benzo[8,8a][1]benzopyrano[2,3-e]isoindole (676) (1R*,6aR,7S,9aS,12R*,13aS)-12-chloro-2,3,6,6a,7,8,9,9a,10,11,12,13-dodecahydro-1-hydroxy-6a,7,10,10-tetramethyl-5-nitro-3,11-dioxo-1H-benzo[8,8a][1]benzopyrano[2,3-e]isoindole (677) (6aR,7S,9aS,11R*,12R*,13aS)-12-bromo-5-carboxy-11-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (678) (6aR,7S,9aS,11R*,13aS)-12-amino-11-chloro-2,3,6,6a,7,8,9,9a,10,11,12,13-dodecahydro-5- methoxycarbonyl-6a,7,10,10-tetramethyl-3-oxo-1H-benzo[8,8a][1]benzopyrano[2,3-e]isoindole
(679) (1R*,6aR,7S,9aS,12R*,13aS)-4-chloro-2,3,6,6a,7,8,9,9a,10,11,12,13-dodecahydro-12-methoxy-1-methoxyphenyl-6a,7,10,10-tetramethyl-3,11-dioxo-1H-benzo[8,8a][1]benozpyrano[2,3-e]isoindole
(680) (1R*,6aR,7S,9aS,12R*,13aS)-4-chloro-2,3,6,6a,7,8,9,9a,10,11,12,13-dodecahydro-1-methoxyphenyl-6a,7,10,10-tetramethyl-12-methylamino-3,11-dioxo-1H-benzo[8,8a][1]benzopyrano[2,3-e]isoindole
(681) (1R*,6aR,7S,9aS,12R*,13aS)-12-bromo-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole
(682) (6aR,7S,9aS,11R*,12R*,13aS)-11-chloro-2,3,6,6a,7,8,9,9a,10,11,12,13-dodecahydro-12-hdyroxy-6a,7,10,10-tetramethyl-3-oxo-4-trifluoromethyl-1H-benzo[8,8a][1]benozpyrano[2,3-e]isoindole
(683) (6aR,7S,9aS,12R*,13aS)-5-cyano-2,3,6,6a,7,8,9,9a,10,11,12,13-dodecahydro-12-hydroxy-6a,7,10,10-tetramethyl-3,11-dioxo-1H-benoz[8,8a][1]benzopyrano[2,3-e]isoindole
(684) (6a,7S,11R*,12R*,13aS)-4-carbamoyl-2,3,6,6a,7,8,9,9a,10,11,12,13-dodecahydro-11-hydroxy-12-methoxy-6a,7,10,10-tetramethyl-3-oxo-1H-benzo[8,8a][1]benzopyrano[2,3-e]isoindole
(685) (6aR,7S,9aS,11R*,12R*,13aS)-4,12-dichloro-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole
(686) (6aR,7S,9aS,11R*,12R*,13aS)-11-bromo-2,3,6,6a,7,8,9,9a,10,11,12,13-dodecahydro-6a,7,10,10-tetramethyl-12-methylamino-4-nitro-3-oxo-1H-benzo[8,8a][1]benozpyrano[2,3-e]isoindole
(687) (6aR,7S,9aS,11R*,12R*,13aS)-4,11-dichloro-2,3,6,6a,7,8,9,9a,10,11,12,12-dodecahydro-12-methoxy-6a,7,10,10-tetramethyl-3-oxo-1H-benzo[8,8a][1]benzoypyrano[2,3-e]isoindole
(688) (6aR,7S,9aS,11R*,12R*,13aS)-11-bromo-2,3,6,6a,7,8,9,9a,10,11,12,13-dodecahydro-6a,7,10,10-tetramethyl-3-oxo-5-trifluoromethyl-1H-benzo[8,8a][1]benzopyrano[2,3-e]isoindole
(689) (6aR,7S,9aS,11R*,12R*,13aS)-4,12-dibromo-2,3,6,6aR,7,8,9,9a,10,11,12,13-dodecahydro-6a,7,10,10-tetramethyl-3-oxo-1H-benzo[8,8a][1]benzopyrano[2,3-e]isoindole
(690) (6aR,7S,9aS,11R*,12R*,13aS)-5-carboxy-2,3,6,6a,7,8,9,9a,10,11,12,13-dodecahydro-11,12-dihydroxy-6a,7,10,10-tetramethyl-3-oxo-1H-benzo[8,8a][1]benzopyrano[2,3-e]isoindole
(691) (6aR,7S,9aS,12R*,13aS)-12-bromo-4-cyano-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole
(692) (6aR,7S,9aS,11R*,12R*,13aS)-12-acetylamino-5-carbamoyl-11-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole
(693) (6a,R,7S,9aS,11R*,12R*,13aS)-5-bromo-2,3,6,6a,7,8,9,9a,10,11,12,13-dodecahydro-6a,7,10,10-tetramethyl-12-methylamino-3-oxo-1H-benzo[8,8a][1]benzopyrano[2,3-e]isoindole
(694) (6aR,7S,9aS,11R*,12R*,13aS)-12-amino-4-carboxy-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole
(695) (6aR,7S,9aS,11R*,12R*,13aS)-2,3,6,6a,7,8,9,9a10,11,12,13-dodecahydro-4,11-dihydroxy-6a,7,10,10-tetramethyl-3-oxo-1H-benzo[8,8a][1]benzopyrano[2,3-e]isoindole
(696) (6aR,7S,9aS,11R*,12R*,13aS)-2,3,6,6a,7,8,9,9a,10,11,12,13-dodecahydro-11-hydroxy-12-methoxy-6a,7,10,10-tetramethyl-3-oxo-4-trifluoromethyl-1H-benzo[8,8a][1]benzopyrano[2,3-e]isoindole
(697) (6aR,7S,9aS,11R*,12R*,13aS)-11-bromo-12-chloro-2,3,6,6a,7,8,9,9a,10,11,12,13-dodecahydro-6a,7,10,10-tetramethyl-3-oxo-4-trifluoromethyl-1H-benzo[8,8a][1]benzopyrano[2,3-e]isoindole
(698) (1R*,6aR,7S,9aS,12R*,13aS)-2,3,6,6a,7,8,9,9a,10,11,12,13-dodecahydro-1-hydroxyphenyl12-methoxy-6a,7,10,10-tetramethyl-3,11-dioxo-1H-benzo[8,8a][1]benzopyrano[2,3-e]isoindole
(699) (1R*,6aR,7S,9aS,12R*,13aS)-2,3,6,6a,7,8,9,9a,10,11,12,13-dodecahydro-1-methoxyphenyl-6a,7,10,10-tetramethyl-12-methylamino-4-nitro-3,11-dioxo-1H-benzo[8,8a][1]benzopyrano[2,3-e]isoindole
(700) (1R*,6aR,7S,9aS,12R*,13aS)-12-amino-4-carboxy-2,3,6,6a,7,8,9,9a,10,11,12,13-dodecahydro-6a,7,10,10-tetramethyl-3-oxo-1H-benzo[8,8a][1]benzopyrano[2,3-e]isoindole
(701) (1R*,6aR,7S,9aS,12R*,13aS)-2,3,6,6a,7,8,9,9a,10,11,12,13-dodecahydro-4-hydroxy-12-methoxy-6a,7,10,10-tetramethyl-3-oxo-1H-benzo[8,8a][1]benzopyrano[2,3-e]isoindole
(702) (6a,7S,9aS,11R*,12R*,13aS)-12-amino-5-carboxy-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole
(703) (1R*,6aR,7S,9aS,12R*,13aS)-2,3,6,6a,7,8,9,9a,10,11,12,13-dodecahydro-1,12-dihydroxy-6a,7,10,10-tetramethyl-4-nitro-3,11-dioxo-1H-benzo[8,8a][1]benzopyrano[2,3-e]isoindole
(704) (1R*,6aR,7S,9aS,12R*,13aS)-11-bromo-2,3,6,6a,7,8,9,9a,10,11,12,13-dodecahydro-6a,7,10,10-tetramethyl-4-nitro-3-oxo-1H-benzo[8,8a][1]benzopyrano[2,3-e]isoindole
(705) (1R*,6aR,7S,9aS,13aS)-5-chloro-2,3,6,6a,7,8,9,9a,10,11,12,13-dodecahydro-1-methoxy-6a,7,10,10-tetramethyl-3,11-dioxo-1H-benzo[8,8a][1]benzopyrano[2,3-e]isoindole
(706) (1R*,6aR,7S,9aS,13aS)-12-amino-5-carboxy-2,3,6,6a,7,8,9,9a,10,11,12,13-dodecahydro-6a,7,10,10-tetramethyl-3-oxo-1H-benzo[8,8a][1]benzopyrano[2,3-e]isoindole
(707) (6aR,7S,9aS,11R*,12R*,13aS)-12-acetylamino-4-carbamoyl-11-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole
(608) (6aR,7S,9aS,13aS)-4-chloro-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole
(709) (6aR,7S,9aS,13aS)-12-bromo-2,3,6,6a,7,8,9,9a,10,11,12,13-dodecahydro-5-methoxycarbonyl- 6a ,7,10,10-tetramethyl-3-oxo-1H-benzo[8,8a][1]benzopyrano[2,3-e]isoindole
(710) (6aR,7S,9aS,11R*,12R*,13aS)-11-bromo-2,3,6,6a,7,8,9,9a,10,11,12,13-dodecahydro-12-methoxy-6a,7,10,10-tetramethyl-3-oxo-1H-benzo[8,8a][1]benzopyrano[2,3-e]isoindole
(711) (6aR,7S,9aS,11R*,12R*,13aS)-11-bromo-4-carboxy-2,3,6,6a,7,8,9,9a,10,11,12,13-dodecahydro-6a,7,10,10-tetramethyl-12-methylamino-3-oxo-1H-benzo[8,8a][1-benzopyrano[2,3-e]isoindole
(712) (6aR,7S,9aS,11R*,12R*,13aS)-4-carbamoyl-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (713) (6aR,7S,9aS,11R*,12R*,13aS)-12-acetylamino-2,3,6a,7,8,9,9a,10,11,12,13-dodecahydro-4-methoxycarbonyl-6a,7,10,10-tetramethyl-3-oxo-1H-benzo[8,8a][1]benzopyrano[2,3-e]isoindole (714) (6aR,7S,9aS,11R*,12R*,13aS)-5-carbamoyl-2,3,6,6a,7,8,9,9a,10,11,12,13-dodecahydro-11-hydroxy-6a,7,10,10-tetramethyl-3-oxo-1H-benzo[8,8a][1]benzopyrano[2,3-]isoindole (715) (6a,7S,9aS,12R*,13aS)-12-chloro-2,3,6,6a,7,8,9,9a,10,11,12,13-dodecahydro-6a,7,10,10-tetramethyl-3,11-dioxo-4-trifluoromethyl-1H-benzo[8,8a][1]benzopyrano[2,3-e]isoindole (716) (6aR,7S,9aS,12R*,13aS)-12-amino-5-carbamoyl-2,3,6,6a,7,8,9,9a,10,11,12,13-dodecahydro-6a,7,10,10-tetramethyl-3-oxo-1H-benzo[8,8a][1]benzopyrano[2,3-e]isoindole (717) (6aR,7S,9aS,13aS)-2,3,6,6a,7,8,9,9a,10,11,12,13-dodecahydro-6a,7,10,10-tetramethyl-3,11-dioxo-4-trifluoromethyl-1H-benzo[8,8a][1]benzopyrano[2,3-e]isoindole (718) (6aR,7S,9aS,12R*,13aS)-12-bromo-2,3,6,6a,7,8,9,9a,10,11,12,13dodecahydro-6a,7,10,10-tetramethyl-4-nitro-3,11-dioxo-1H-benzo[8,8a][1]benzopyrano[2,3-e]isoindole (719) (6aR,7S,9aS,12R*,13aS)-12-bromo-2,3,6,6a,7,8,9,9a,10,11,12,13-dodecahydro-4-methoxy-6a,7,10,10-tetramethyl-3,11-dioxo-1H-benzo[8,8a][1]benzopyrano[2,3-e]isoindole (720) (6aR,7S,9aS,11R*,12R*,13aS)-12-amino-11-bromo-2,3,6,6a,7,8,9,9a,10,11,12,13dodecahydro-6a,7,10,10-tetramethyl-4-nitro-3-oxo-1H-benzo[8,8a][1]benzopyrano[2,3-e]isoindole (721) (1R*,6aR,7S,9aS,12R*,13aS)-12-acetylamino-2,3,6,6a,7,8,9,9a,10,11,12,13-dodecahydro-1-hydroxyphenyl-6a,7,10,10-tetramethyl-3,11-dioxo-1H-benzo[8,8a][1]benozpyrano[2,3-e]isoindole (722) (1R*,6aR,7S,9aS,12R*,13aS)-12-acetylamino-2,3,6,6a,7,8,9,9a,10,11,12,13-dodecahydro-1-methoxy-6a,7,10,10-tetramethyl-3,11-dioxo-1H-benzo[8,8a][1]benzopyrano[2,3-a]isoindole (723) (6a,7S,9aS,12R*,13aS)-2,3,6,6a,7,8,9,9a,10,11,12,13-dodecahydro-6a,7,10,10-tetramethyl-12-methylamino-5-nitro-3,11-dioxo-1H-benzo[8,8a][1]benzopyrano[2,3-e]isoindole (724) (6aR,7S,9aS,12R*,13aS)-4-bromo-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (725) (6aR,7S,9aS,11R*,12R*,13aS)-11-chloro-2,3,6,6a,7,8,9,9a,10,11,12,13-dodecahydro-12-methoxy-6a,7,10,10-tetramethyl-3-oxo-1H-benzo[8,8a][1]benzopyrano[2,3-e]isoindole (726) (6aR,7S,9aS,11R*,12R*,13aS)-4-chloro-11,12-epoxy-2,3,6,6a,7,8,9,9a,10,11,12,13-dodecahydro-6a,7,10,10-tetramethyl-3-oxo-1H-benzo[8,8a,][1]benzopyrano[2,3-e]isoindole (727) (6aR,7S,9aS,11R*,12R*,13aS)-2,3,6,6a,7,8,9,9a,10,11,12,13-dodecahydro-4-hydroxy-6a,7,10,10-tetramethyl-12-methylamino-3-oxo-1H-benzo[8,8a,][1]benzopyrano[2,3-e]isoindole (728) (6aR,7S,9aS,11R*,12R*,13aS)-12-chloro-2,3,6,6a,7,8,9,9a,10,11,12,13-dodecahydro-6a,7,10,10-tetramethyl-3-oxo-1H-benzo[8,8a][1]benozpyrano[2,3-e]isoindole (729) (6aR,7S,9aS,11R*,12R*,13aS)-12-amino-4-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (730) (1R*,6aR,7S,12R*,13aS)-4-bromo-2,3,6,6a,7,8,9,9a,10,11,12,13-dodecahydro-12-hydroxy-1-hydroxyphenyl-6a,7,10,10-tetramethyl-3,11-dioxo-1H-benzo[8,8a][1]benzopyrano[2,3-e]isoindole (731) (1R*,6aR,7S,9aS,12R*,13aS)-2,3,6,6a,7,8,9,9a,10,11,12,13-dodecahydro-12-hydroxy-1-methoxy-6a,7,10,10-tetramethyl-4-nitro-3,11-dioxo-1H-benzo[8,8a][1]benozpyrano[2,3-e]isoindole (732) (6aR,7S,9aS,11R*,12R*,13aS)-11-bromo-4-carboxy-2,3,6,6a,7,8,9,9a,10,11,12,13-dodecahydro-12-methoxy-6a,7,10,10-tetramethyl-3-oxo-1H-benzo[8,8a][1]benzopyrano[2,3-e]isoindole (733) (6aR,7S,9aS,11R*,12R*,13aS)-4-carboxy-2,3,6,6a,7,8,9,9a,10,11,12,13-dodecahydro-11-hydroxy-12-methoxy-6a,7,10,10-tetramethyl-3-oxo-1H-benzo[8,8a][1]benzopyrano[2,3-e]isoindole (734) (1R*,6aR,7S,9aS,12R*,13aS)-12-bromo-4-chloro-2,3,6,6a,7,8,9,9a,10,11,12,13-dodecahydro-1-hydroxy-6a,7,10,10-tetramethyl-3,11-dioxo-1H-benzo[8,8a][1]benzopyrano[2,3-e]isoindole (735) (1R*,6aR,7S,9aS,12R*,13aS)-4-bromo-2,3,6,6a,7,8,9,9a,10,11,12,13-dodecahydro-1-methoxyphenyl-6a,7,10,10-tetramethyl-12-methylamino-3,11-dioxo-1H-benzo[8,8a][1]benzopyrano[2,3-e]isoindole (736) (6aR,7S,9aS,11R*,12R*,13aS)-11-bromo-2,3,6,6a,7,8,9,9a,10,11,12,13-dodecahydro-5-methoxycarbonyl-6a,7,10,10-tetramethyl-12-methylamino-3-oxo-1H-benzo[8,8a][1]benzopyrano[2,3-]isoindole (737) (6aR,7S,9aS,11R*,12R*,13aS)-11-chloro-2,3,6,6a,7,8,9,9a,10,11,12,13-dodecahydro-12-methoxy-6a,7,10,10-tetramethyl-5-nitro-3-oxo-1H-benzo[8,8a][1]benzopyrano[2,3-e]isoindole (738) (6aR,7S,9aS,11R*,12R*,13aS)-12-chloro-2,3,6,6a,7,8,9,9a,10,11,12,13-dodecahydro-11-hydroxy-6a,7,10,10-tetramethyl-4-nitro-3-oxo-1H-benzo[8,8a][1]benzopyrano[2,3-e]isoindole (739) (6aR,7S,9aS,11R*,12R*,13aS)-11-bromo-5-carboxy-12-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (740) (1R*,6aR,7S,9aS,12R*,13aS)-12-bromo-2,3,6,6a,7,8,9,9a,10,11,12,13-dodecahydro-1-methoxy-6a,7,10,10-tetramethyl-3,11-dioxo-1H-benzo[8,8a][1]benzopyrano[2,3-e]isoindole (741) (1R*,6aR,7S,9aS,12R*,13aS)-12-bromo-2,3,6,6a,7,8,9,9a,10,11,12,13-dodecahydro-6a,7,10,10-tetramethyl-3-oxo-1H-benzo[8,8a][1]benzopyrano[2,3-e]isoindole (742) (6aR,7S,9aS,12R*,13aS)-12-amino-2,3,6,6a,7,8,9,9a,10,11,12,13-dodecahydro-5-methoxycarbonyl-6a,7,10,10-tetramethyl-3,11-dioxo-1H-benzo[8,8a][1]benzopyrano[2,3-e]isoindole (743) (6aR,7S,9aS,12R*,13aS)-5-bromo-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (744) (6aR,7S,9aS,11R*,12R*,13aS)-12-bromo-5-carboxy-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (745) (1R*,6aR,7S,9aS,12R*,13aS)-2,3,6,6a,7,8,9,9a,10,11,12,13-dodecahydro-1-hydroxy-12-methoxy-6a,7,10,10-tetramethyl-3,11-dioxo-1H-benzo[8,8a][1]benzopyrano[2,3-e]isoindole (746) (1R*,6aR,7S,9aS,12R*,13aS)-4-chloro-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (747) (6aR,7S,9aS,11R*,12R*,13aS)-11-bromo-4-carboxy-12-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (748) (6aR,7S,9aS,12R*,13aS)-12-amino-4-bromo-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (749) (6aR,7S,9aS,12R*,13aS)-4-carbamoyl-12-chloro-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (750) (6aR,7S,9aS,12R*,13aS)-2,3,6,6a,7,8,9,9a,10,11,12,13-dodecahydro-12-methoxy-6a,7,10,10-tetramethyl-5-nitro-3-oxo-1H-benzo[8,8a][1]benzopyrano[2,3-e]isoindole (751) (1R*,6aR,7S,9aS,12R*,13aS)-12-bromo-2,3,6,6a,7,8,9,9a,10,11,12,13-dodecahydro-1-methoxy-6a,7,10,10-tetramethyl-4-nitro-3,11-dioxo-1H-benzo[8,8a][1]benzopyrano[2,3-e]isoindole (752) (6aR,7S,9aS,13aS)-5-bromo-2,3,6,6a,7,8,9,9a,10,11,12,13-dodecahydro-6a,7,10,10-tetramethyl-3-oxo-1H-benzo[8,8a][1]benzopyrano[2,3-e]isoindole (753) (1R*,6aR,7S,9aS,12R*,13aS)-12-acetylamino-4-bromo-2,3,6,6a,7,8,9,9a,10,11,12,13-dodecahydro-1-methoxyphenyl-6a,7,10,10-tetramethyl-3,11-dioxo-1H-benzo[8,8a][1]benzopyrano[2,3-e]isoindole (754) (6aR,7S,9aS,11R*,12R*,13aS)-11-bromo-4-chloro-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (755) (6aR,7S,9aS,11R*,12R*,13aS)-12-amino-5-bromo-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (756) (1R*,6aR,7S,9aS,12R*,13aS)-12-acetylamino-4-bromo-2,3,6,6a,7,8,9,9a,10,11,12,13-dodecahydro-1-hydroxy-6a,7,10,10-tetramethyl-3,11-dioxo-1H-benzo[8,8a][1]benzopyrano[2,3-e]isoindole (757) (6aR,7S,9aS,11R*,12R*,13aS)-11-bromo-12-chloro-2,3,6,6a,7,8,9,9a,10,11,12,13-dodecahydro-4-hydroxy-6a,7,10,10-tetramethyl-3-oxo-1H-benzo[8,8a][1]benzopyrano[2,3-e]isoindole (758) (6aR,7S,9aS,11R*,12R*,13aS)-11-bromo-2,3,6,6a,7,8,9,9a,10,11,12,13-dodecahydro-4-hydroxy-6a,7,10,10-tetramethyl-12-methylamino-3-oxo-1H-benzo[8,8a][1]benzopyrano[2,3-e]isoindole (759) (1R*,6aR,7S,9aS,12R*,13aS)-2,3,6,6a,7,8,9,9a,10,11,12,13-dodecahydro-1-hydroxy-12-methoxy-6a,7,10,10-tetramethyl-4-nitro-3,11-dioxo-1H-benzo[8,8a][1]benzopyrano[2,3-e]isoindole (760) (1R*,6aR,7S,9aS,13aS)-2,3,6,6a,7,8,9,9a,10,11,12,13-dodecahydro-1-methoxy-6a,7,10,10-tetramethyl-5-nitro-3,11-dioxo-1H-benzo[8,8a][1]benzopyrano[2,3-e]isoindole (761) (6aR,7S,9aS,11R*,12R*,13aS)-12-amino-5,11-dichloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (762) (1R*,6aR,7S,9aS,12R*,13aS)-2,3,6,6a,7,8,9,9a,10,11,12,13-dodecahydro-1,12-dihydroxy-6a,7,10,10-tetramethyl-3,11-dioxo-1H-benzo[8,8a][1]benzopyrano[2,3-e]isoindole (763) (6aR,7S,9aS,11R*,12R*,13aS)-4-carbamoyl-2,3,6,6a,7,8,9,9a,10,11,12,13-dodecahydro-11-hydroxy-6a,7,10,10-tetramethyl-12-methylamino-3-oxo-1H-benzo[8,8a][1]benzopyrano[2,3-e]isoindole (764) (6aR,7S,9aS,11R*,12R*,13aS)-11-hydroxy-2,3,6,6a,7,8,9,9a,10,11,12,13-dodecahydro-6a,7,10,10-tetramethyl-3-oxo-1H-benzo[8,8a][1]benzopyrano[2,3-e]isoindole (765) (6aR,7S,9aS,12R*,13aS)-2,3,6,6a,7,8,9,9a,10,11,12,13-dodecahydro-4-methoxycarbonyl-6a,7,10,10-tetramethyl-12-methylamino-3,11-dioxo-1H-benzo[8,8a][1]benzopyrano[2,3-e]isoindole (766) (6aR,7S,9aS,12R*,13aS)-2,3,6,6a,7,8,9,9a,10,11,12,13-dodecahydro-12-methoxy-6a,7,10,10-tetramethyl-5-nitro-3,11-dioxo-1H-benzo[8,8a][1]benzopyrano[2,3-e]isoindole (767) (1R*,6aR,7S,9aS,12R*,13aS)-2,3,6,6a,7,8,9,9a,10,11,12,13-dodecahydro-12-hydroxy-1-methoxyphenyl-6a,7,10,10-tetramethyl-3,11-dioxo-1H-benzo[8,8a][1]benzopyrano[2,3-e]isoindole (768) (1R*,6aR,7S,9aS,12R*,13aS)-5-chloro-2,3,6,6a,7,8,9,9a,10,11,12,13-dodecahydro-1-hydroxyphenyl-6a,7,10,10-tetramethyl-12-methylamino-3,11-dioxo-1H-benzo[8,8a][1]benzopyrano[2,3-e]isoindole (769) (1R*,6aR,7S,9aS,12R*,13aS)-5-bromo-2,3,6,6a,7,8,9,9a,10,11,12,13-dodecahydro-1-methoxy-6a,7,10,10-tetramethyl-12-methylamino-3,11-dioxo-1H-benzo[8,8a][1]benzopyrano[2,3-e]isoindole (770) (1R*,6aR,7S,9aS,12R*,13aS)-11-bromo-5-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (771) (1R*,6aR,7S,9aS,12R*,13aS)-5-chloro-2,3,6,6a,7,8,9,9a,10,11,12,13-dodecahydro-12-hydroxy-1-hydroxphenyl-6a,7,10,10-tetramethyl-3,11-dioxo-1H-benzo[8,8a][1]benzopyrano[2,3-e]isoindole (772) (6aR,7S,9aS,13aS)-4-chloro-2,3,6,6a,7,8,9,9a,10,11,12,13-decahydro-6a,7,10,10-tetramethyl-3-oxo-1H-benzo[8,8a][1]benzopyrano[2,3-e]isoindole (773) (6aR,7S,9aS,13aS)-12-acetylamino-4-carbamoyl-2,3,6,6a,7,8,9,9a,10,11,12,13-dodecahydro-6a,7,10,10-tetramethyl-3-oxo-1H-benzo[8,8a][1]benzopyrano[2,3-e]isoindole (774) (6aR,7S,9aS,13aS)-12-acetylamino-2,3,6,6a,7,8,9,9a,10,11,12,13-decahydro-5-methoxycarbonyl-6a,7,10,10-tetramethyl-3-oxo-1H-benzo[8,8a][1]benzopyrano[2,3-e]isoindole (775) (1R*,6aR,7S,9aS,12R*,13a)-2,3,6,6a,7,8,9,9a,10,11,12,13-dodecahydro-1-methoxy-6a,7,10,10-tetramethyl-12-methylamino-3,11-1H-benzo[8,8a][1]benzopyrano[2,3-e]isoindole (776) (6aR,7S,9aS,12R*,13aS)-12-acetylamino-5-carbamoyl-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (777) (6aR,7S,9aS,12R*,13aS)-12-bromo-5-carboxy-2,3,6,6a,7,8,9,9a,10,11,12,13-dodecahydro-6a,7,10,10-tetramethyl-3-oxo-1H-benzo[8,8a][1]benzopyrano[2,3-e]isoindole (778) (6aR,7S,9aS,13aS)-2,3,6,6a,7,8,9,9a,10,11,12,13-dodecahydro-4-hydroxy-6a,7,10,10-tetramethyl-3,11-dioxo-1H-benzo[8,8a][1]benzopyrano[2,3-e]isoindole (779) (1R*,6aR,7S,9aS,12R*,13aS)-2,3,6,6a,7,8,9,9a,10,11,12,13-dodecahydro-12-hydroxy-1-methoxy-6a,7,10,10-tetramethyl-5-nitro-3,11-dioxo-1H-benzo[8,8a][1]benzopyrano[2,3-e]isoindole (780) (1R*,6aR,7S,9aS,12R*,13aS)-12-bromo-4-carbamoyl-2,3,6,6a,7,8,9,9a,10,11,12,13-dodecahydro-6a,7,10,10-tetramethyl-3-oxo-1H-benzo[8,8a][1]benzopyrano[2,3-e]isoindole (781) (1R*,6aR,7S,9aS,12R*,13aS)-5-bromo-2,3,6,6a,7,8,9,9a,10,11,12,13-dodecahydro-12-methoxy-6a,7,10,10-tetramethyl-3-oxo-1H-benzo[8,8a][1]benzopyrano[2,3-e]isoindole (782) (6aR,7S,9aS,12R*,13aS)-5-carboxy-2,3,6,6a,7,8,9,9a,10,11,12,13-dodecahydro-6a,7,10,10-tetramethyl-12-methylamino-3,11-dioxo-1H-benzo[8,8a][1]benzopyrano[2,3-e]isoindole (783) (6aR,7S,9aS,12R*,13aS)-12-amino-5-bromo-2,3,6,6a,7,8,9,9a,10,11,12,13-dodecahydro-6a,7,10,10-tetramethyl-3-oxo-1H-benzo[8,8a][1]benzopyrano[2,3-e]isoindole (784) (1R*,6aR,7S,9aS,12R*,13aS)-4-bromo-12-chloro-2,3,6,6a,7,8,9,9a,10,11,12,13-dodecahydro-1-methoxyphenyl-6a,7,10,10-tetramethyl-3,11-dioxo-1H-benzo[8,8a][1]benzopyrano[2,3-e]isoindole (785) (6aR,7S,9aS,11R*,12R*,13aS)-11-chloro-2,3,6,6a,7,8,9,9a,10,11,12,13-dodecahydro-12-hydroxy-6a,7,10,10-tetramethyl-5-nitro-3-oxo-1H-benzo[8,8a][1]benzopyrano[2,3-e]isoindole (786) (6aR,7S,9aS,11R*,12R*,13aS)-4-carbamoyl-11,12-dichloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (787) (6aR,7S,9aS,11R*,12R*,13aS)-12-chloro-2,3,6,6a,7,8,9,9a,10,11,12,13-dodecahydro-6a,7,10,10-tetramethyl-3-oxo-4-trifluoromethyl-1H-benzo[8,8a][1]benzopyrano[2,3-e]isoindole (788) (6aR,7S,9aS,12R*,13aS)-12-chloro-2,3,6,6a,7,8,9,9a,10,11,12,13-dodecahydro-4-methoxycarbonyl-6a,7,10,10-tetramethyl-3,11-dioxo-1H-benzo[

(789) (1R*, 6a R, 7S, 9a S, 12 R*, 13a S)-12-acetylamino-5-chloro-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole (790) (6a R, 7S, 9a S, 11 R*, 12 R*, 13a S)-2,3,6,6a,7,8,9,9a,10,11,12,13-dodecahydro-11,12-dihydroxy-6a,7,10,10-tetramethyl-3-oxo-5-trifluoromethyl-1H-benzo[8,8a][1]benzopyrano[2,3-e]isoindole (791) (6a R, 7S, 9a S, 11 R*, 12 R*, 13a S)-12-chloro-2,3,6,6a,7,8,9,9a,10,11,12,13-dodecahydro-11-hydroxy-4-methoxycarbonyl-6a,7,10,10-tetramethyl-3-oxo-1H-benzo[8,8a][1]benzopyrano[2,3-e]isoindole (792) (1R*, 6a R, 7S, 9a S, 12 R*, 13a S)-12-chloro-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole (793) (1R*, 6a R, 7S, 9a S, 12 R*, 13a S)-5-bromo-2,3,6,6a,7,8,9,9a,10,11,12,13-dodecahydro-12-hydroxy-1-methoxy-6a,7,10,10-tetramethyl-3,11-dioxo-1H-benzo[8,8a][1]benzopyrano[2,3-e]isoindole (794) (6a R, 7S, 9a S, 11 R*, 12 R*, 13a S)-4,11-dibromo-12-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (795) (6a R, 7S, 9a S, 11 R*, 12 R*, 13a S)-12-amino-11-chloro-4-cyano-2,3,6,6a,7,8,9,9a,10,11,12,13-dodecahydro-6a,7,10,10-tetramethyl-3-oxo-1H-benzo[8,8a][1]benzopyrano[2,3-e]isoindole (796) (1R*, 6a R, 7S, 9a S, 13a S)-5-bromo-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole (797) (6a R, 7S, 9a S, 11 R*, 12 R*, 13a S)-12-amino-11-bromo-2,3,6,6a,7,8,9,9a,10,11,12,13-dodecahydro-6a,7,10,10-tetramethyl-3-oxo-5-trifluoromethyl-1H-benzo[8,8a][1]benzopyrano[2,3-e]isoindole (798) (6a R, 7S, 9a S, 11 R*, 12 R*, 13a S)-12-bromo-5-carbamoyl-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (799) (6a R, 7S, 9a S, 11 R*, 12 R*, 13a S)-11,12-epoxy-2,3,6,6a,7,8,9,9a,10,11,12,13-dodecahydro-6a,7,10,10-tetramethyl-3-oxo-1H-benzo[8,8a][1]benzopyrano[2,3-e]isoindole (800) (6a R, 7S, 9a S, 11 R*, 12 R*, 13a S)-5,11-dibromo-12-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (801) (6a R, 7S, 9a S, 11 R*, 12 R*, 13a S)-12-acetylamino-4-bromo-2,3,6,6a,7,8,9,9a,10,11,12,13-dodecahydro-6a,7,10,10-tetramethyl-3-oxo-1H-benzo[8,8a][1]benzopyrano[2,3-e]isoindole (802) (6a R, 7S, 9a S, 12 R*, 13a S)-5-carboxy-2,3,6,6a,7,8,9,9a,10,11,12,13-dodecahydro-12-hydroxy-6a,7,10,10-tetramethyl-3,11-dioxo-1H-benzo[8,8a][1]benzopyrano[2,3-e]isoindole (803) (6a R, 7S, 9a S, 11 R*, 12 R*, 13a S)-11-chloro-2,3,6,6a,7,8,9,9a,10,11,12,13-dodecahydro-5-methoxycarbonyl-6a,7,10,10-tetramethyl-12-methylamino-3-oxo-1H-benzo[8,8a][1]benzopyrano[2,3-e]isoindole (804) (6a R, 7S, 9a S, 11 R*, 12 R*, 13a S)-12-acetylamino-11-chloro-2,3,6,6a,7,8,9,9a,10,11,12,13-dodecahydro-4-hydroxy-6a,7,10,10-tetramethyl-3-oxo-1H-benzo[8,8a][1]benzopyrano[2,3-e]isoindole (805) (6a R, 7S, 9a S, 13a S)-2,3,6,6a,7,8,9,9a,10,11,12,13-dodecahydro-5-methoxycarbonyl-6a,7,10,10-tetramethyl-3-oxo-1H-benzo[8,8a][1]benzopyrano[2,3-e]isoindole (806) (6a R, 7S, 9a S, 11 R*, 12 R*, 13a S)-2,3,6,6a,7,8,9,9a,10,11,12,13-dodecahydro-11,12-dihydroxy-6a,7,10,10-tetramethyl-3-oxo-4-trifluoromethyl-1H-benzo[8,8a][1]benzopyrano[2,3-e]isoindole (807) (6a R, 7S, 9a S, 11 R*, 12 R*, 13a S)-11-bromo-12-chloro-5-cyano-2,3,6,6a,7,8,9,9a,10,11,12,13-dodecahydro-6a,7,10,10-tetramethyl-3-oxo-1H-benzo[8,8a][1]benzopyrano[2,3-e]isoindole (808) (6a R, 7S, 9a S, 11 R*, 12 R*, 13a S)-2,3,6,6a,7,8,9,9a,10,11,12,13-dodecahydro-4-methoxy-6a,7,10,10-tetramethyl-12-methylamino-3-oxo-1H-benzo[8,8a][1]benzopyrano[2,3-e]isoindole (809) (6a R, 7S, 9a S, 11 R*, 12 R*, 13a S)-12-acetylamino-11-bromo-4-carbamoyl-2,3,6,6a,7,8,9,9a,10,11,12,13-dodecahydro-6a,7,10,10-tetramethyl-3-oxo-1H-benzo[8,8a][1]benzopyrano[2,3-e]isoindole (810) (6a R, 7S, 9a S, 11 R*, 12 R*, 13a S)-4-chloro-2,3,6,6a,7,8,9,9a,10,11,12,13-dodecahydro-11,12-dihydroxy-6a,7,10,10-tetramethyl-3-oxo-1H-benzo[8,8a][1]benzopyrano[2,3-e]isoindole (811) (6a R, 7S, 9a S, 11 R*, 12 R*, 13a S)-2,3,6,6a,7,8,9,9a,10,11,12,13-dodecahydro-11-hydroxy-12-methoxy-6a,7,10,10-tetramethyl-3-oxo-1H-benzo[8,8a][1]benzopyrano[2,3-e]isoindole (812) (1R*, 6a R, 7S, 9a S, 13a S)-5-chloro-2,3,6,6a,7,8,9,9a,10,11,12,13-dodecahydro-1-hydroxy-6a,7,10,10-tetramethyl-3,11-dioxo-1H-benzo[8,8a][1]benzopyrano[2,3-e]isoindole (813) (1R*, 6a R, 7S, 9a S, 12 R*, 13a S)-5-chloro-2,3,6,6a,7,8,9,9a,10,11,12,13-dodecahydro-1-hydroxy-12-methoxy-6a,7,10,10-tetramethyl-3,11-dioxo-1H-benzo[8,8a][1]benzopyrano[2,3-e]isoindole (814) (6a R, 7S, 9a S, 13a S)-4-cyano-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (815) (1R*, 6a R, 7S, 9a S, 12 R*, 13a S)-5,12-dibromo-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole (816) (6a R, 7S, 9a S, 11 R*, 12 R*, 13a S)-4-carbamoyl-11-chloro-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (817) (1R*, 6a R, 7S, 9a S, 12 R*, 13a S)-12-bromo-4-chloro-2,3,6,6a,7,8,9,9a,10,11,12,13-dodecahydro-1-methoxyphenyl-6a,7,10,10-tetramethyl-3,11-dioxo-1H-benzo[8,8a][1]benzopyrano[2,3-e]isoindole (818) (1R*, 6a R, 7S, 9a S, 12 R*, 13a S)-12-amino-2,3,6,6a,7,8,9,9a,10,11,12,13-dodecahydro-4-methoxycarbonyl-6a,7,10,10-tetramethyl-3-oxo-1H-benzo[8,8a][1]benzopyrano[2,3-e]isoindole (819) (6a R, 7S, 9a S, 12 R*, 13a S)-5-carboxy-12-chloro-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (820) (1R*, 6a R, 7S, 9a S, 13a S)-2,3,6,6a,7,8,9,9a,10,11,12,13-dodecahydro-1-hydroxy-6a,7,10,10-tetramethyl-5-nitro-3,11-dioxo-1H-benzo[8,8a][1]benzopyrano[2,3-e]isoindole (821) (6a R, 7S, 9a S, 13a S)-2,3,6,6a,7,8,9,9a,10,11,12,13-dodecahydro-5-methoxycarbonyl-6a,7,10,10-tetramethyl-3,11-dioxo-1H-benzo[8,8a][1]benzopyrano[2,3-e]isoindole (822) (6a R, 7S, 9a S, 11 R*, 12 R*, 13a S)-12-acetylamino-2,3,6,6a,7,8,9,9a,10,11,12,13-dodecahydro-11-hydroxy-4-methoxycarbonyl-6a,7,10,10-tetramethyl-3-oxo-1H-benzo[8,8a][1]benzopyrano[2,3-e]isoindole (823) (6a R, 7S, 9a S, 12 R*, 13a S)-12-bromo-5-chloro-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (824) (1R*, 6a R, 7S, 9a S, 12 R*, 13a S)-12-acetylamino-4-bromo-2,3,6,6a,7,8,9,9a,10,11,12,13-dodecahydro-1-methoxy-6a,7,10,10-tetramethyl-3,11-dioxo-1H-benzo[8,8a][1]benzopyrano[2,3-e]isoindole (825) (6a R, 7S, 9a S, 12 R*, 13a S)-12-bromo-2,3,6,6a,7,8,9,9a,10,11,12,13-dodecahydro-6a,7,10,10-tetramethyl-3,11-dioxo-4-trifluoromethyl-1H-benzo[8,8a][1]benzopyrano[2,3-e]isoindole (826) (6a R, 7S, 9a S, 11 R*, 12 R*, 13a S)-12-amino-5-bromo-11-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (827) (6a R, 7S, 9a S, 11 R*, 12 R*, 13a S)-12-amino-11-chloro-2,3,6,6a,7,8,9,9a,10,11,12,13-dodecahydro-4-hydroxy-6a,7,10,10-tetramethyl-3-oxo-1H-benzo[8,8a][1]benzopyrano[2,3-e]isoindole (828) (1R*, 6a R, 7S, 9a S, 12 R*, 13a S)-12-acetylamino-4-chloro-2,3,6,6a,7,8,9,9a,10,11,12,13-dodecahydro-1-hydroxyphenyl-6a,7,10,10-tetramethyl-3,11-dioxo-1H-benzo[8,8a][1]benzopyrano[2,3-e]isoindole (829) (1R*, 6a R, 7S, 9a S, 12 R*, 13a S)-4-bromo-2,3,6,6a,7,8,9,9a,10,11,12,13-dodecahydro-1-hydroxy-6a,7,10,10-tetramethyl-12-methylamino-3,11-dioxo-1H-benzo[8,8a][1]benzopyrano[2,3-e]isoindole (830) (6a R, 7S, 9a S, 12 R*, 13a S)-4-carboxy-2,3,6,6a,7,8,9,9a,10,11,12,13-dodecahydro-6a,7,10,10-tetramethyl-12-methylamino-3,11-dioxo-1H-benzo[8,8a][1]benzopyrano[2,3-e]isoindole (831) (6a R, 7S, 9a S, 11 R*, 12 R*, 13a S)-4-carbamoyl-12-chloro-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (832) (6a R, 7S, 9a S, 11 R*, 12 R*, 12 R*, 13a S)-12-bromo-4-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (833) (6a R, 7S, 9a S, 11 R*, 12 R*, 13a S)-11-bromo-2,3,6,6a,7,8,9,9a,10,11,12,13-dodecahydro-12-methoxy-6a,7,10,10-tetramethyl-3-oxo-4-trifluoromethyl-1H-benzo[8,8a][1]benzopyrano[2,3-e]isoindole (834) (6a R, 7S, 9a S, 11 R*, 12 R*, 13a S)-11-bromo-5-carboxy-2,3,6,6a,7,8,9,9a,10,11,12,13-dodecahydro-6a,7,10,10-tetramethyl-12-methylamino-3-oxo-1H-benzo[8,8a][1]benzopyrano[2,3-e]isoindole (835) (6a R, 7S, 9a S, 11 R*, 12 R*, 13a S)-2,3,6,6a,7,8,9,9a,10,11,12,13-dodecahydro-12-hydroxy-6a,7,10,10-tetramethyl-5-nitro-3-oxo-1H-benzo[8,8a][1]benzopyrano[2,3-e]isoindole (836) (6a R, 7S, 9a S, 11 R*, 12 R*, 13a S)-2,3,6,6a,7,8,9,9a,10,11,12,13-dodecahydro-11-hydroxy-4-methoxycarbonyl-6a,7,10,10-tetramethyl-3-oxo-1H-benzo[8,8a][1]benzopyrano[2,3-e]isoindole (837) (6a R, 7S, 9a S, 11 R*, 12 R*, 13a S)-2,3,6,6a,7,8,9,9a,10,11,12,13-dodecahydro-11-hydroxy-12-methoxy-5-methoxycarbonyl-6a,7,10,10-tetramethyl-3-oxo-1H-benzo[8,8a][1]benzopyrano[2,3-e]isoindole (838) (6a R, 7S, 9a S, 13a S)-2,3,6,6a,7,8,9,9a,10,11,12,13-dodecahydro-4-methoxy-6a,7,10,10-tetramethyl-3,11-dioxo-1H-benzo[8,8a][1]benzopyrano[2,3-e]isoindole (839) (6a R, 7S, 9a S, 11 R*, 12 R*, 13a S)-12-amino-2,3,6,6a,7,8,9,9a,10,11,12,13-dodecahydro-11-hydroxy-5-methoxycarbonyl-6a,7,10,10-tetramethyl-3-oxo-1H-benzo[8,8a][1]benzopyrano[2,3-e]isoindole (840) (1R*, 6a R, 7S, 9a S, 12 R*, 13a S)-4,12-dichloro-2,3,6,6a,7,8,9,9a,10,11,12,13-dodecahydro-1-methoxyphenyl-6a,7,10,10-tetramethyl-3,11-dioxo-1H-benzo[8,8a][1]benzopyrano[2,3-e]isoindole (841) (6a R, 7S, 9a S, 11 R*, 12 R*, 13a S)-2,3,6,6a,7,8,9,9a,10,11,12,13-dodecahydro-11,12-dihydroxy-6a,7,10,10-tetramethyl-3-oxo-1H-benzo[8,8a][1]benzopyrano[2,3-e]isoindole (842) (6a R, 7S, 9a S, 11 R*, 12 R*, 13a S)-11-chloro-2,3,6,6a,7,8,9,9a,10,11,12,13-dodecahydro-6a,7,10,10-tetramethyl-12-methylamino-3-oxo-4-trifluoromethyl-1H-benzo[8,8a][1]benzopyrano[2,3-e]isoindole (843) (6a R, 7S, 9a S, 11 R*, 12 R*, 13a S)-12-acetylamino-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (844) (1R*, 6a R, 7S, 9a S, 12 R*, 13a S)-4,12-dichloro-2,3,6,6a,7,8,9,9a,10,11,12,13-dodecahydro-1-hydroxy-6a,7,10,10-tetramethyl-3,11-dioxo-1H-benzo[8,8a][1]benzopyrano[2,3-e]isoindole (845) (6a R, 7S, 9a S, 11 R*, 12 R*, 13a S)-12-acetylamino-11-bromo-2,3,6,6a-7,8,9,9a,10,11,12,13-dodecahydro-4-hydroxy-6a,7,10,10-tetramethyl-3-oxo-1H-benzo[8,8a][1]benzopyrano[2,3-e]isoindole (846) (6a R, 7S, 9a S, 11 R*, 12 R*, 13a S)-12-acetylamino-11-chloro-2,3,6,6a,7,8,9,9a,10,11,12,13-dodecahydro-6a,7,10,10-tetramethyl-5-nitro-3-oxo-1H-benzo[8,8a][1]benzopyrano[2,3-e]isoindole (847) (6a R, 7S, 9a S, 11 R*, 12 R*, 13a S)-11-chloro-2,3,6,6a,7,8,9,9a,10,11,12,13-dodecahydro-12-hydroxy-6a,7,10,10-tetramethyl-3-oxo-5-trifluoromethyl-1H-benzo[8,8a][1]benzopyrano[2,3-e]isoindole (848) (6a R, 7S, 9a S, 11 R*, 12 R*, 13a S)-11-chloro-2,3,6,6a,7,8,9,9a,10,11,12,13-dodecahydro-5-methoxycarbonyl-6a,7,10,10-tetramethyl-3-oxo-1H-benzo[8,8a][1]benzopyrano[2,3-e]isoindole (849) (6a R, 7S, 9a S, 11 R*, 12 R*, 13a S)-12-acetylamino-5-bromo-11-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (850) (6a R, 7S, 9a S, 11 R*, 12 R*, 13a S)-11-bromo-2,3,6,6a,7,8,9,9a,10,11,12,13-dodecahydro-6a,7,10,10-tetramethyl-12-methylamino-5-nitro-3-oxo-1H-benzo[8,8a][1]benzopyrano[2,3-e]isoindole (851) (6a R, 7S, 9a S, 11 R*, 12 R*, 13a S)-5-carbamoyl-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (852) (6a R, 7S, 9a S, 12 R*, 13a S)-12-chloro-5-cyano-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (853) (6a R, 7S, 9a S, 12 R*, 13a S)-11-chloro-2,3,6,6a,7,8,9,9a,10,11,12,13-dodecahydro-4-methoxycarbonyl-6a,7,10,10-tetramethyl-3-oxo-1H-benzo[8,8a][1]benzopyrano[2,3-e]isoindole (854) (6a R, 7S, 9a S, 12 R*, 13a S)-4-carbamoyl-12-chloro-2,3,6,6a,7,8,9,9a,10,11,12,13-dodecahydro-6a,7,10,10-tetramethyl-3-oxo-1H-benzo[8,8a][1]benzopyrano[2,3-e]isoindole (855) (1R*, 6a R, 7S, 9a S, 12 R*, 13a S)-5-bromo-2,3,6,6a,7,8,9,9a,10,11,12,13-dodecahydro-1-methoxyphenyl-6a,7,10,10-tetramethyl-12-methylamino-3,11-dioxo-1H-benzo[8,8a][1]benzopyrano[2,3-e]isoindole (856) (1R*, 6a R, 7S, 9a S, 12 R*, 13a S)-5,12-dibromo-2, 3, 6, 6a, 7, 8, 9, 9a, 10, 11, 12, 13-dodecahydro-1,12-dimethoxy-6a,7,10,10-tetramethyl-3,11-dioxo-1H-benzo[8,8a][1]benzopyrano[2,3-e]isoindole (857) (1R*, 6a R, 7S, 9a S, 12 R*, 13a S)-5,12-dichloro-2, 3, 6, 6a, 7, 8, 9, 9a, 10, 11, 12, 13-dodecahydro-1methoxy-6a,7,10,10-tetramethyl-3,11-dioxo-1H-benzo[8,8a][1]benzopyrano[2,3-e]isoindole (858) (1R*, 6a R, 7S, 9a S, 12 R*, 13a S)-4-carbamoyl-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (859) (1R*, 6a R, 7S, 9a S, 12 R*, 13a S)-2, 3, 6, 6a, 7, 8, 9, 9a, 10, 11, 12, 13-dodecahydro-12-hydroxy-1-hydroxyphenyl-6a,7,10,10-tetramethyl-3,11-dioxo-1H-benzo[8,8a][1]benzopyrano[2,3-e]isoindole (860) (1R*, 6a R, 7S, 9a S, 12 R*, 13a S)-4-bromo-2, 3, 6, 6a, 7, 8, 9, 9a, 10, 11, 12, 13-dodecahydro-1-hydroxyphenyl12-methoxy-6a,7,10,10-tetramethyl-3,11-dioxo-1H-benzo[8,8a][1]benzopyrano[2,3-e]isoindole (861) (1R*, 6a R, 7S, 9a S, 12 R*, 13a S)-5-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (862) (1R*, 6a R, 7S, 9a S, 12 R*, 13a S)-4-chloro-2, 3, 6, 6a, 7, 8, 9, 9a, 10, 11, 12, 13-dodecahydro-12-hydroxy-1-hydroxyphenyl-6a,7,10,10-tetramethyl-3,11-dioxo-1H-benzo[8,8a][1]benzopyrano[2,3-e]isoindole (863) (6a R, 7S, 9a S, 13a S)-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (864) (6a R, 7S, 9a S, 11 R*, 12 R*, 13a S)-12-acetylamino-4-bromo-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (865) (6a R, 7S, 9a S, 11 R*, 12 R*, 13a S)-12-acetylamino-4-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (866) (6a R, 7S, 9a S, 11 R*, 12 R*, 13a S)-11-bromo-4-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (867) (6a R, 7S, 9a S, 13a S)-4-carbamoyl-2, 3, 6, 6a, 7, 8, 9, 9a, 10, 11, 12, 13-dodecahydro- 6a,7,10,10-tetramethyl-3-oxo-1H-benzo[8,8a][1]benzopyrano[2,3-e]isoindole (868) (6a R, 7S, 9a S, 12 R*, 13a S)-12-bromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (869) (1R*, 6a R, 7S, 9a S, 12 R*, 13a S)-5-bromo-2, 3, 6, 6a, 7, 8, 9, 9a, 10, 11, 12, 13-dodecahydro-12-hydroxy-1-methoxyphenyl-6a,7,10,10-tetramethyl-3,11-dioxo-1H-benzo[8,8a][1]benzopyrano[2,3-e]isoindole (870) (6a R, 7S, 9a S, 11 R*, 12 R*, 13a S)-12-acetylamino-5-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (871) (1R*, 6a R, 7S, 9a S, 12 R*, 13a S)-4,12-dibromo-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (872) (1R*, 6a R, 7S, 9a S, 12 R*, 13a S)-12-acetylamino-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (873) (1R*, 6a R, 7S, 9a S, 12 R*, 13a S)-2, 3, 6, 6a, 7, 8, 9, 9a, 10, 11, 12, 13-dodecahydro-4-methoxycarbonyl-6a,7,10,10-tetramethyl-12-methylamino-3-oxo-1H-benzo[8,8a][1]benzopyrano[2,3-e]isoindole (874) (6a R, 7S, 9a S, 11 R*, 12 R*, 13a S)-4-carboxy-2, 3, 6, 6a, 7, 8, 9, 9a, 10, 11, 12, 13-dodecahydro-11,12-dihydroxy-6a,7,10,10-tetramethyl-3-oxo-1H-benzo[8,8a][1]benzopyrano[2,3-e]isoindole (875) (6a R, 7S, 9a S, 11 R*, 12 R*, 13a S)-5-carboxy-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (876) (6a R, 7S, 9a S, 11 R*, 12 R*, 13a S)-11-bromo-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (877) (1R*, 6a R, 7S, 9a S, 12 R*, 13a S)-4-chloro-2, 3, 6, 6a, 7, 8, 9, 9a, 10, 11, 12, 13-dodecahydro-1-hydroxyphenyl12-methoxy-6a,7,10,10-tetramethyl-3,11-dioxo-1H-benzo[8,8a][1]benzopyrano[2,3-e]isoindole (878) (1R*, 6a R, 7S, 9a S, 12 R*, 13a S)-5-carboxy-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3 -e]isoindole (879) (1R*, 6a R, 7S, 9a S, 12 R*, 13a S)-5,12-dibromo-4-chloro-2, 3, 6, 6a, 7, 8, 9, 9a, 10, 11, 12, 13-dodecahydro-1,12-dimethoxy-6a,7,10,10-tetramethyl-3,11-dioxo-1H-benzo[8,8a][1]benzopyrano[2,3-e]isoindole (880) (1R*, 6a R, 7S, 9a S, 12 R*, 13a S)-2, 3, 6, 6a, 7, 8, 9, 9a, 10, 11, 12, 13-dodecahydro-12-methoxy-1-methoxyphenyl-6a,7,10,10-tetramethyl-5-nitro-3,11-dioxo-1H-benzo[8,8a][1]benzopyrano[2,3-e]isoindole (881) (1R*, 6a R, 7S, 9a S, 12 R*, 13a S)-12-chloro-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (882) (1R*, 6a R, 7S, 9a S, 12 R*, 13a S)-5-cyano-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (883) (6a R, 7S, 9a S, 11 R*, 12 R*, 13a S)-4,11-dichloro-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (884) (6a R, 7S, 9a S, 11 R*, 12 R*, 13a S)-12-amino-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (885) (6a R, 7S, 9a S, 12 R*, 13a S)-4-cyano-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole (886) (6a R, 7S, 9a S, 12 R*, 13a S)-4,11-dibromo-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (887) (6a R, 7S, 9a S, 12 R*, 13a S)-4-carboxy-12-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (888) (1R*, 6a R, 7S, 9a S, 12 R*, 13a S)-12-acetylamino-5-bromo-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (889) (6a R, 7S, 9a S, 12 R*, 13a S)-12-amino-2, 3, 6, 6a, 7, 8, 9, 9a, 10, 11, 12, 13-dodecahydro-6a,7,10,10-tetramethyl-5-nitro-3,11-dioxo-1H-benzo[8,8a][1]benzopyrano[2,3-e]isoindole (890) (6a R, 7S, 9a S, 13a S)-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (891) (1R*, 6a R, 7S, 9a S, 13a S)-4-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (892) (1R*, 6a R, 7S, 9a S, 12 R*, 13a S)-12-chloro-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (893) (1R*, 6a R, 7S, 9a S, 12 R*, 13a S)-12-acetylamino-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (894) (1R*, 6a R, 7S, 9a S, 12 R*, 13a S)-12-acetylamino-2, 3, 6, 6a, 7, 8, 9, 9a, 10, 11, 12, 13-dodecahydro-1-hydroxyphenyl-6a,7,10,10-tetramethyl-4-nitro-3,11-dioxo-1H-benzo[8,8a][1]benzopyrano[2,3-e]isoindole (895) (6a R, 7S, 9a S, 12 R*, 13a S)-4,12-dibromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (896) (6a R, 7S, 9a S, 11 R*, 12 R*, 13a S)-11-bromo-2, 3, 6, 6a, 7, 8, 9, 9a, 10, 11, 12, 13-dodecahydro-12-hydroxy-6a,7,10,10-tetramethyl-4-nitro-3-oxo-1H-benzo[8,8a][1]benzopyrano[2,3-e]isoindole (897) (6a R, 7S, 9a S, 11 R*, 12 R*, 13a S)-5-bromo-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3-e]isoindole (898) (6a R, 7S, 9a S, 12 R*, 13a S)-12-acetylamino-2, 3, 6, 6a, 7, 8, 9, 9a, 10, 11, 12, 13-dodecahydro-6a,7,10,10-tetramethyl-4-nitro-3,11-dioxo-1H-benzo[8,8a][1]benzopyrano[2,3-e]isoindole (899) (6a R, 7S, 9a S, 12 R*, 13a S)-12-chloro-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (900) (1R*, 6a R, 7S, 9a S, 13a S)-5-bromo-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (901) (6a R, 7S, 9a S, 11 R*, 12 R*, 13a S)-5-carboxy-2, 3, 6, 6a, 7, 8, 9, 9a, 10, 11, 12, 13 -dodecahydro-11-hydroxy-12-methoxy-6a,7,10,10-tetramethyl-3-oxo-1H-benzo[8,8a][1]benzopyrano[2,3-e]isoindole (902) (6a R, 7S, 9a S, 11 R*, 12 R*, 13a S)-12-bromo-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (903) (1R*, 6a R, 7S, 9a S, 12 R*, 13a S)-12-acetylamino-5-bromo-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (904) (6a R, 7S, 9a S, 12 R*, 13a S)-12-acetylamino-4-carbamoyl-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (905) (6a R, 7S, 9a S, 12 R*, 13a S)-12-amino-4-carboxy-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (906) (6a R, 7S, 9a S, 12 R*, 13a S)-12-acetylamino-5-cyano-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (907) (6a R, 7S, 9a S, 12 R*, 13a S)-12-amino-2, 3, 6, 6a, 7, 8, 9, 9a, 10, 11, 12, 13-dodecahydro-11-hydroxy-4-methoxycarbonyl-6a,7,10,10-tetramethyl-3-oxo-1H-benzo[8,8a][1]benzopyrano[2,3-e]isoindole (908) (6a R, 7S, 9a S, 11 R*, 12 R*, 13a S)-5-carboxy-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (909) (6a R, 7S, 9a S, 12 R*, 13a S)-2, 3, 6, 6a, 7, 8, 9, 9a, 10, 11, 12, 13-dodecahydro-12-hydroxy-4-methoxy-6a,7,10,10-tetramethyl-3,11-dioxo-1H-benzo[8,8a][1]benzopyrano[2,3-e]isoindole (910) (6a R, 7S, 9a S, 11 R*, 12 R*, 13a S)-12-bromo-2, 3, 6, 6a, 7, 8, 9, 9a, 10, 11, 12, 13-dodecahydro-11-hydroxy-4-methoxycarbonyl-6a,7,10,10-tetramethyl-3-oxo-1H-benzo[8,8a][1]benzopyrano[2,3-e]isoindole (911) (6a R, 7S, 9a S, 11 R*, 12 R*, 13a S)-12-acetylamino-5-carboxy-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (912) (1R*, 6a R, 7S, 9a S, 12 R*, 13a S)-5-chloro-2, 3, 6, 6a, 7, 8, 9, 9a, 10, 11, 12, 13 dodecahyro-1-hydroxy-6a,7,10,10-tetramethyl-12-methylamino-3,11-dioxo-1H-benzo[8,8a][1]benzopyrano[2,3-e]isoindole (913) (6a R, 7S, 9a S, 11 R*, 12 R*, 13a S)-5-carbamoyl-11-chloro-2, 3, 6, 6a, 7, 8, 9, 9a, 10, 11, 12, 13-dodecahyro-12-methoxy-6a,7,10,10-tetramethyl-3-oxo-1H-benzo[8,8a][1]benzopyrano[2,3-e]isoindole (914) (6a R, 7S, 9a S, 11 R*, 12 R*, 13a S)-12-amino-11-chloro-2, 3, 6, 6a, 7, 8, 9, 9a, 10, 11, 12, 13-dodecahyro-6a,7,10,10-tetramethyl-5-nitro-3-oxo-1H-benzo[8,8a][1]benzopyrano[2,3-e]isoindole (915) (6a R, 7S, 9a S, 11 R*, 12 R*, 13a S)-12-chloro-5-cyano-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,4-e]isoindole (916) (6a R, 7S, 9a S, 11 R*, 12 R*, 13a S)-11-bromo-2, 3, 6, 6a, 7, 8, 9, 9a, 10, 11, 12, 13-dodecahydro-12-hydroxy-4-methoxycarbonyl-6a,7,10,10-tetramethyl-3-oxo-1H-benzo[8,8a][1]benzopyrano[2,3-e]isoindole (917) (6a R, 7S, 9a S, 11 R*, 12 R*, 13a S)-12-bromo-4-carboxy-2, 3, 6, 6a, 7, 8, 9, 9a, 10, 11, 12, 13-dodecahyro- 11-hydroxy-6a,7,10,10-tetramethyl-3-oxo-1H-benzo[8,8a][1]benzopyrano[2,3-e]isoindole (918) (6a R, 7S, 9a S, 12 R*, 13a S)-12-amino-2, 3, 6, 6a, 7, 8, 9, 9a, 10, 11, 12, 13-dodecahydro-4-methoxycarbonyl-6a,7,10,10-tetramethyl-3,11-dioxo-1H-benzo[8,8a][1]benzopyrano[2,3-e]isoindole (919) (6a R, 7S, 9a S, 11 R*, 12 R*, 13a S)-5-bromo-2, 3, 6, 6a, 7, 8, 9, 9a, 10, 11, 12, 13-dodecahydro-11-hydroxy-12-methoxy-6a,7,10,10-tetramethyl-3-oxo-1H-benzo[8,8a][1]benzopyrano[2,3-e]isoindole (920) (6a R, 7S, 9a S, 11 R*, 12 R*, 13a S)-12-amino-11-bromo-5-carboxy-2, 3, 6, 6a, 7, 8, 9, 9a, 10, 11, 12, 13-dodecahyro-6a,7,10,10-tetramethyl-3-oxo-1H-benzo[8,8a][1]benzopyrano[2,3-e]isoindole (921) (6a, R, 7S, 9a S, 12 R*, 13a S)-12-amino-4-cyano-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (922) (6a, R, 7S, 9a S, 11 R*, 12 R*, 13a S)-2, 3, 6, 6a, 7, 8, 9, 9a, 10, 11, 12, 13-dodecahydro-11,12-dihydroxy-6a,7,10,10-tetramethyl-5-nitro-3-oxo-1H-benzo[8,8a][1]benzopyrano[2,3-e]isoindole (923) (1R*, 6a R, 7S, 9a S, 12 R*, 13a S)-12-acetylamino-2, 3, 6, 6a, 7, 8, 9, 9a, 10, 11, 12, 13-dodecahyro-1-methoxyphenyl-6a,7,10,10-tetramethyl-3,11-dioxo-1H-benzo[8,8a][1]benzopyrano[2,3-e]isoindole (924) (6a R, 7S, 9a S, 11 R*, 12 R*, 13a S)-12-bromo-4, 11-dichloro-2, 3, 6, 6a, 7, 8, 9, 9a, 10, 11, 12, 13-dodecahyro-6a,7,10,10-tetramethyl-3-oxo-1H-benzo[8,8a][1]benzopyrano[2,3-e]isoindole (925) (1R*, 6a, R, 7S, 9a S, 12 R*, 13a S)-12-amino-4-bromo-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (926) (6a R, 7S, 9a S, 11 R*, 12 R*, 13a S)-4-carboxy-11-chloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (927) (6a, R, 7S, 9a S, 11 R*, 12 R*, 13a S)-2, 3, 6, 6a, 7, 8, 9, 9a, 10, 11, 12, 13-dodecahydro-6a,7,10,10-tetramethyl-12-methylamino-5-nitro-3-oxo-1H-benzo[8,8a][1]benzopyrano[2,3-e]isoindole (928) (6a, R, 7S, 9a S, 13a S)-4-carboxy-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (929) (6a R, 7S, 9a S, 13a S)-5-chloro-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (930) (6a R, 7S, 9a S, 11 R*, 12 R*, 13a S)-2, 3, 6, 6a, 7, 8, 9, 9a, 10, 11, 12, 13-dodecahydro-11-hydroxy-6a,7,10,10,10-tetramethyl-12-methylamino-3-oxo-1H-benzo[8,8a][1]benzopyrano[2,3-e]isoindole (931) (6a R, 7S, 9a S, 11 R*, 12 R*, 13a S)-4-carboxy-11, 12-dichloro-2, 3, 6, 6a, 7, 8, 9, 9a, 10, 11, 12, 13-dodecahydro-6a,7,10,10-tetramethyl-3-oxo-1-H-benzo[8,8a][1]benzopyrano[2,3-e]isoindole (932) (6a R, 7S, 9a S, 11 R*, 12 R*, 13a S)-12-bromo-11-chloro-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (933) (6a R, 7S, 9a S, 11 R*, 12 R*, 13a S)-2, 3, 6, 6a, 7, 8, 9, 9a, 10, 11, 12, 13-dodecahydro-11-hydroxy-5-methoxycarbonyl-6a,7,10,10-tetramethyl-12-methylamino-3-oxo-1H-benzo[8,8a][1]benzopyrano[2,3-e]isoindole (934) (6a R, 7S, 9a S, 12 R*, 13a S)-5-cyano-2, 3, 6, 6a, 7, 8, 9, 9a, 10, 11, 12, 13-dodecahydro-6a,7,10,10-tetramethyl-12-methylamino-3,11-dioxo-1H-benzo[8,8a][1]benzopyrano[2,3-e]isoindole (935) (6a R, 7S, 9a S, 11 R*, 12 R*, 13a S)-2, 3, 6, 6a, 7, 8, 9, 9a, 10, 11, 12, 13-dodecahyro-11-hydroxy-4-methoxy-6a,7,10,10-tetramethyl-12-methylamino-3-oxo-1H-benzo [8,8a][1]benzopyrano[2,3-e]isoindole (936) (6a R, 7S, 9a S, 12 R*, 13a S)-12-amino-5-chloro-2, 3, 6, 6a, 7, 8, 9, 9a, 10, 11, 12, 13-dodecahyro-6a,7,10,10-tetramethyl-3,11-dioxo-1H-benzo[8,8a][1]benzopyrano[2,3-e]isoindole (937) (1R*, 6a R, 7S, 9a S, 12 R*, 13a S)-2, 3, 6, 6a, 7, 8, 9, 9a, 10, 11, 12, 13-dodecahydro-1-hydroxyphenyl12-methoxy-6a,7,10,10-tetramethyl-5-nitro-3,11-dioxo-1H-benzo[8,8a][1]benzopyrano[2,3-e]isoindole (938) (1R*, 6a, R, 7S, 9a S, 12 R*, 13a S)-5,12-dibromo-2, 3, 6, 6a, 7, 8, 9, 9a, 10, 11, 12, 13-dodecahydro-1,12-dimethoxy-6a,7,10,10-tetramethyl-4-nitro-3,11-dioxo-1H-benzo[8,8a][1]benzopyrano[2,3-e]isoindole (939) (1R*, 6a R, 7S, 9a S, 12 R*, 13a S)-11-chloro-5-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (940) (1R*, 6a R, 7S, 9a S, 12 R*, 13a S)-5-bromo-12-chloro-2, 3, 6, 6a, 7, 8, 9, 9a, 10, 11, 12, 13-dodecahydro-1-hydroxyphenyl-6a,7,10,10-tetramethyl-3,11-dioxo-1H-benzo[8,8a][1]benzopyrano[2,3-e]isoindole (941) (6a R, 7S, 9a S, 11 R*, 12 R*, 13a S)-11-bromo-2, 3, 6, 6a, 7, 8, 9, 9a, 10, 11, 12, 13-dodecahyro-4,12-dihydroxy-6a,7,10,10-tetramethyl-3-oxo-1H-benzo[8,8a][1]benzopyrano[2,3-e]isoindole (942) (6a R, 7S, 9a S, 11 R*, 12 R*, 13a S)-5-carboxy-12-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (943) (6a R, 7S, 9a S, 11 R*, 12 R*, 13a S)-11-chloro-2, 3, 6, 6a, 7, 8, 9, 9a, 10, 11, 12, 13-dodecahydro-6a,7,10,10-tetramethyl-12-methylamino-4-nitro-3-oxo-1H-benzo[8,8a][1]benzopyrano[2,3-e]isoindole (944) (6a R, 7S, 9a S, 12 R*, 13a S)-2, 3, 6, 6a, 7, 8, 9, 9a, 10, 11, 12, 13-dodecahyro-4-hydroxy-12-methoxy-6a,7,10,10-tetramethyl-3,11-dioxo-1H-benzo[8,8a][1]benzopyrano[2,3-e]isoindole (945) (6a R, 7S, 9a S, 12 R*, 13a S)-2, 3, 6, 6a, 7, 8, 9, 9a, 10, 11, 12, 13-dodecahydro-12-hydroxy-6a,7,10,10-tetramethyl-4-nitro-3,11-dioxo-1H-benzo[8,8a][1]benzopyrano[2,3-e]isoindole (946) (6a R, 7S, 9a S, 11 R*, 12 R*, 13a S)-11-bromo-5-carbamoyl-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (947) (1R*, 6a R, 7S, 9a S, 12 R*, 13a S)-2, 3, 6, 6a, 7, 8, 9, 9a, 10, 11, 12, 13-dodecahydro-1-hydroxyphenyl-6a,7,10,10-tetramethyl-12-methylamino-5-nitro-3,11-dioxo-1H-benzo[8,8a][1]benzopyrano[2,3-e]isoindole (948) (6a R, 7S, 9a S, 11 R*, 12 R*, 13a S)-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (949) (6a R, 7S, 9a S, 11 R*, 12 R*, 13a S)-11,12-dichloro-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (950) (6a R, 7S, 9a S, 12 R*, 13a S)-2, 3, 6, 6a, 7, 8, 9, 9a, 10, 11, 12, 13-dodecahydro-12-hydroxy-6a,7,10,10-tetramethyl-3,11-dioxo-1H-benzo[8,8a][1]benzopyrano[2,3-e]isoindole (951) (1R*, 6a R, 7S, 9a S, 12 R*, 13a S)-5-bromo-2, 3, 6, 6a, 7, 8, 9, 9a, 10, 11, 12, 13-dodecahydro-1-hydroxy-6a, 7,10,10-tetramethyl-12-methylamino-3,11-dioxo-1H-benzo[8,8a][1]benzopyrano[2,3-e]isoindole (952) (6a R, 7S, 9a S, 11 R*, 12 R*, 13a S)-11,12-dichloro-2, 3, 6, 6a, 7, 8, 9, 9a, 10, 11, 12, 13-dodecahydro-4-hydroxy-6a,7,10,10-tetramethyl-3-oxo-1H-benzo[8,8a][1]benzopyrano[2,3-e]isoindole (953) (1R*, 6a R, 7S, 9a S, 12 R*, 13a S)-12-bromo-5-chloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (954) (1R*, 6a R, 7S, 9a S, 12 R*, 13a S)-4-bromo-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (955) (1R*, 6a R, 7S, 9a S, 12 R*, 13a S)-2, 3, 6, 6a, 7, 8, 9, 9a, 10, 11, 12, 13-dodecahydro-5-methoxycarbonyl-6a,7,10,10-tetramethyl-12-methylamino-3-oxo-1H-benzo[8,8a][1]benzopyrano[2,3-e]isoindole (956) (6a R, 7S, 9a S, 11 R*, 12 R*, 13a S)-11-bromo-5-cyano-2, 3, 6, 6a, 7, 8, 9, 9a, 10, 11, 12, 13-dodecahydro-12-hydroxy-6a,7,10,10-tetramethyl-3-oxo-1H-benzo[8,8a][1]benzopyrano[2,3-e]isoindole (957) (6a R, 7S, 9a S, 11 R*, 12 R*, 13a S)-12-bromo-11-chloro-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (958) (6a R, 7S, 9a S, 12 R*, 13a S)-12-acetylamino-2, 3, 6, 6a, 7, 8, 9, 9a, 10, 11, 12, 13-dodecahydro-5-methoxycarbonyl-6a,7,10,10-tetramethyl-3,11-dioxo-1H-benzo[8,8a][1]benzopyrano[2,3-e]isoindole (959) (6a R, 7S, 9a S, 11 R*, 12 R*, 13a S)-5-carboxy-2, 3, 6, 6a, 7, 8, 9, 9a, 10, 11, 12, 13-dodecahydro-11-hydroxy-6a,7,10,10-tetramethyl-12-methylamino-3-oxo-1H-benzo[8,8a][1]benzopyrano[2,3e]isoindole (960) (6a R, 7S, 9a S, 11 R*, 12 R*, 13a S)-2, 3, 6, 6a, 7, 8, 9, 9a, 10, 11, 12, 13-dodecahydro-11-hydroxy-4-methoxy-6a,7,10,10-tetramethyl-3-oxo-1H-benzo[8,8a][1]benzopyrano[2,3-e]isoindole (961) (6a R, 7S, 9a S, 11 R*, 12 R*, 13a S)-4-carbamoyl-2, 3, 6, 6a, 7, 8, 9, 9a, 10, 11, 12, 13-dodecahydro-6a,7,10,10-tetramethyl-12-methylamino-3-oxo-1H-benzo[8,8a][1]benzopyrano[2,3-e]isoindole (962) (6a R, 7S, 9a S, 11 R*, 12 R*, 13a S)-12-amino-11-chloro-2, 3, 6, 6a, 7, 8, 9, 9a, 10, 11, 12, 13-dodecahydro-4-methoxy-6a,7,10,10-tetramethyl-3-oxo-1H-benzo[8,8a][1]benzopyrano[2,3-e]isoindole (963) (6a R, 7S, 9a S, 11 R*, 12 R*, 13a S)-4-carboxy-11-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (964) (1R*, 6a R, 7S, 9a S, 12 R*, 13a S)-5,12-dibromo-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (965) (1R*, 6a R, 7S, 9a S, 12 R*, 13a S)-2, 3, 6, 6a, 7, 8, 9, 9a, 10, 11, 12, 13-dodecahydro-12-methoxy-6a,7,10,10-tetramethyl-3-oxo-1H-benzo[8,8a][1]benzopyrano[2,3-e]isoindole (966) (6a R, 7S, 9a S, 11 R*, 12 R*, 13a S)-5-carboxy-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (967) (6a, R, 7S, 9a S, 11 R*, 12 R*, 13a S)-5-carboxy-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (968) (6a R, 7S, 9a S, 11 R*, 12 R*, 13a S)-11-chloro-4-cyano-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (969) (1R*, 6a R, 7S, 9a S, 12 R*, 13a S)-4-bromo-2, 3, 6, 6a, 7, 8, 9, 9a, 10, 11, 12, 13- dodecahydro-1-hydroxy-12-methoxy-6a,7,10,10-tetramethyl-3,11-dioxo-1H-benzo[8,8a][1]benzopyrano[2,3-e]isoindole (970) (6a R, 7S, 9a S, 11 R*, 12 R*, 13a S)-12-bromo-5-cyano-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (971) (6a R, 7S, 9a S, 11 R*, 12 R*, 13a S)-2, 3, 6, 6a, 7, 8, 9, 9a, 10, 11, 12, 13-dodecahydro-4,11-dihydroxy-12-methoxy-6a,7,10,10-tetramethyl-3-oxo-1H-benzo[8,8a][1]benzopyrano[2,3-e]isoindole (972) (6a R, 7S, 9a S, 11 R*, 12 R*, 13a S)-12-bromo-11-chloro-2, 3, 6, 6a, 7, 8, 9, 9a, 10, 11, 12, 13-dodecahydro-6a,7,10,10-tetramethyl-4-nitro-3-oxo-1H-benzo[8,8a][1]benzopyrano[2,3-e]isoindole (973) (1R*, 6a R, 7S, 9a S, 12 R*, 13a S)-4-chloro-2, 3, 6, 6a, 7, 8, 9, 9a, 10, 11, 12, 13-dodecahydro-1-hydroxyphenyl-6a,7,10,10-tetramethyl-12-methylamino-3,11-dioxo-1H-benzo[8,8a][1]benzopyrano[2,3-e]isoindole (974) (6a R, 7S, 9a S, 13a S)-4-carbamoyl-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (975) (6a R, 7S, 9a S, 11 R*, 12 R*, 13a S)-12-amino-11-bromo-4-chloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (976) (1R*, 6a R, 7S, 9a S, 13a S)-4-bromo-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (977) (6a R, 7S, 9a S, 13a S)-5-carbamoyl-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole (978) (1R*, 6a R, 7S, 9a S, 12 R*, 13a S)-12-bromo-2, 3, 6, 6a, 7, 8, 9, 9a, 10, 11, 12, 13-dodecahydro-1-hydroxyphenyl-6a,7,10,10-tetramethyl-4-nitro-3,11-dioxo-1H-benzo[8,8a][1]benzopyrano[2,3-e]isoindole (979) (1R*, 6a R, 7S, 9a S, 13a S)-2, 3, 6, 6a, 7, 8, 9, 9a, 10, 11, 12, 13-dodecahydro-1-methoxy-6a,7,10,10-tetramethyl-4-nitro-3,11-dioxo-1H-benzo[8,8a][1]benzopyrano[2,3-e]isoindole (980) (6a R, 7S, 9a S, 11 R*, 12 R*, 13a S)-4,12-dibromo-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (981) (1R*, 6a R, 7S, 9a S, 12 R*, 13a S)-2, 3, 6, 6a, 7, 8, 9, 9a, 10, 11, 12, 13-dodecahydro-12-methoxy-1-methoxyphenyl-6a,7,10,10-tetramethyl-4-nitro-3,11-dioxo-1H-benzo[8,8a][1]benzopyrano[2,3-e]isoindole (982) (1R*, 6a R, 7S, 9a S, 12 R*, 13a S)-4-bromo-2, 3, 6, 6a, 7, 8, 9, 9a, 10, 11, 12, 13-dodecahydro-12-hydroxy-1-methoxyphenyl-6a,7,10,10-tetramethyl-3,11-dioxo-1H-benzo[8,8a][1]benzopyrano[2,3-e]isoindole (983) (6a R, 7S, 9a S, 11 R*, 12 R*, 13a S)-2, 3, 6, 6a, 7, 8, 9, 9a, 10, 11, 12, 13-dodecahydro-11-hydroxy-4,12-dimethoxy-6a,7,10,10-tetramethyl-3-oxo-1H-benzo[8,8a][1]benzopyrano[2,3-e]isoindole (984) (6a R, 7S, 9a S, 11 R*, 12 R*, 13a S)-11-chloro-5-cyano-2, 3, 6, 6a, 7, 8, 9, 9a, 10, 11, 12, 13-dodecahydro- 6a,7,10,10-tetramethyl-12-methylamino-3-oxo-1H-benzo[8,8a][1]benzopyrano[2,3-e]isoindole (985) (1R*, 6a R, 7S, 9a S, 12 R*, 13a S)-2, 3, 6, 6a, 7, 8, 9, 9a, 10, 11, 12, 13-dodecahydro-12-hydroxy-1-methoxyphenyl-6a,7,10,10-tetramethyl-5-nitro-3,11-dioxo-1H-benzo[8,8a][1]benzopyrano[2,3-e]isoindole (986) (1R*, 6a R, 7S, 9a S, 13a S)-4-chloro-2, 3, 6, 6a, 7, 8, 9, 9a, 10, 11, 12, 13-dodecahydro-1-methoxyphenyl-6a,7,10,10-tetramethyl-3,11-dioxo-1H-benzo[8,8a][1]benzopyrano[2,3-e]isoindole (987) (6a R, 7S, 9a S, 12 R*, 13a S)-12-acetylamino-2, 3, 6, 6a, 7, 8, 9, 9a, 10, 11, 12, 13-dodecahydro-4-hydroxy-6a,7,10,10-tetramethyl-3,11-dioxo-1H-benzo[8,8a][1]benzopyrano[2,3-e]isoindole (988) (6a R, 7S, 9a S, 11 R*, 12 R*, 13a S)-5-carbamoyl-11,12-dichloro-2, 3, 6, 6a, 7, 8, 9, 9a, 10, 11, 12, 13-dodecahydro-6a,7,10,10-tetramethyl-3-oxo-1H-benzo[8,8a][1]benzopyrano[2,3-e]isoindole (989) (1R*, 6a R, 7S, 9a S, 12 R*, 13a S)-12-amino-4-bromo-2, 3, 6, 6a, 7, 8, 9, 9a, 10, 11, 12, 13-dodecahydro-1-methoxy-6a,7,10,10-tetramethyl-3,11-dioxo-1H-benzo[8,8a][1]benzopyrano[2,3-e]isoindole (990) (1R*, 6a R, 7S, 9a S, 12 R*, 13a S)-12-bromo-2, 3, 6, 6a, 7, 8, 9, 9a, 10, 11, 12, 13-dodecahydro-6a,7,10,10-tetramethyl-5-nitro-3-oxo-1H-benzo[8,8a][1]benzopyrano[2,3-e]isoindole (991) (6a R, 7S, 9a S, 11 R*, 12 R*, 13a S)-12-amino-2, 3, 6, 6a, 7, 8, 9, 9a, 10, 11, 12, 13-dodecahydro-11-hydroxy-4-methoxy-6a,7,10,10-tetramethyl-3-oxo-1H-benzo[8,8a][1]benzopyrano[2,3-e]isoindole (992) (6a R, 7S, 9a S, 11 R*, 12 R*, 13a S)-4-carboxy-12-chloro-2, 3, 6, 6a, 7, 8, 9, 9a, 10, 11, 12, 13-dodecahydro-11-hydroxy-6a,7,10,10-tetramethyl-3-oxo-1H-benzo[8,8a][1]benzopyrano[2,3-e]isoindole (993) (1R*, 6a R, 7S, 9a S, 13a S)-4-chloro-2, 3, 6, 6a, 7, 8, 9, 9a, 10, 11, 12, 13-dodecahydro-1-hydroxy-6a,7,10,10-tetramethyl-3,11-dioxo-1H-benzo[8,8a][1]benzopyrano[2,3-e]isoindole (994) (6a R, 7S, 9a S, 11 R*, 12 R*, 13a S)-11-bromo-2, 3, 6, 6a, 7, 8, 9, 9a, 10, 11, 12, 13-dodecahydro-6a,7,10,10-tetramethyl-12-methylamino-3-oxo-4-trifluoromethyl-1H-benzo[8,8a][1]benzopyrano[2,3-e]isoindole (995) (6a R, 7S, 9a S, 11 R*, 12 R*, 13a S)-12-acetylamino-11-chloro-2, 3, 6, 6a, 7, 8, 9, 9a, 10, 11, 12, 13-dodecahydro-6a,7,10,10-tetramethyl-3-oxo-4-trifluoromethyl-1H-benzo[8,8a][1]benzopyrano[2,3-e]isoindole (996) (6a R, 7S, 9a S, 12 R*, 13a S)-5,12-dibromo-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3-e]isoindole The results of pharmacological experiments are shown below.

1) Anti-Viral Activity Against Influenza A Virus

Influenza A/WSN/33 strain or Soviet-type clinical isolate (A/Sendai/N808/91(H1N1)) was propagated in growing hen's eggs, and its infection titer was determined. MDBK cells (derived from bovine kidney) or MDCK cells (derived from dog kidney) were put in each well on 96-well microtest tubes, and incubated overnight in 100 μl each of Eagle's Minimal Essential Medium (E-MEM) supplemented by 10% fetal bovine serum under 5% $CO_2$ at 37° C. Each of the samples to be tested was dissolved in dimethylsulfoxide, diluted appropriately with the above medium, and added to each of the above wells in 50 μl volume. Then, 50 μl of virus diluted with the above medium optionally containing trypsin was added (multiplicity of infection=1) to the well, followed by incubation for 3 days under 5% $CO_2$ at 37° C. To each well was added 30 μl of a dimethylthiazolyldiphenyltetrazolium bromide (MTT) solution (5 mg/ml), followed by incubation for 1 or 6 hours at 37° C. The supernatant was discarded. After addition of 150 μl of 10% Triton X-100 isopropanol solution, the mixture was shaken for 1 hour. The inhibition of cytotoxic effect of the viral infection was then determined by measuring the amount of reduced MTT on the basis of the absorbance of 560 nm with reference to that at 690 nm, and expressed as $EC_{50}$ which is defined as the concentration of the compound capable of inhibiting the cytotoxicity of the virus by 50%.

2) Cytotoxicity Test

As in the measurement of anti-viral activity, samples were added to the cells, and incubated with 50 μl of culture medium instead of the viral dilution. The results are expressed as $CC_{50}$ which is defined as the concentration of the compound at which 50% of the cells are killed due to the toxicity of the compound. The results are shown in the following Table 1.

TABLE 1

| Compound No. | A/WSN/33 | | A/Sendai/N808/91 (H1N1) | |
|---|---|---|---|---|
| | CC50 | EC50 | CC50 | EC50 |
| 4 | 25 | 0.002 | 10 | 0.1–1 |
| 12 | 25–50 | 0.001–0.002 | 10 | 0.04–0.08 |
| 15 | 25 | 0.063–0.125 | | |
| 19 | 25–50 | 0.063–0.125 | | |
| 26 | >50 | 0.008 | >100 | 1.25–2.5 |
| 27 | 12.5 | 0.063–0.125 | | |
| 28 | 1.6–3.2 | 0.0016–0.0032 | 1.6–3.2 | 0.013 |
| 29 | 3.2–6.3 | 0.001 | 3.2–6.3 | 0.025–0.05 |
| 30 | 6.3–12.5 | 0.016–0.032 | 25–50 | 0.1–0.2 |
| 31 | 12.5 | 0.004–0.008 | 25–50 | 0.0125–0.025 |
| 34 | 12.5 | 0.032–0.063 | 10–100 | 0.4–0.8 |
| 35 | 6.3–12.5 | 0.016–0.032 | 1–10 | 0.4 |
| 36 | 12.5 | 0.002 | 25–50 | 0.05–0.1 |
| 49 | >5 | 0.02 | | |
| 51 | 25–50 | 0.025–0.050 | | |
| 54 | 6.4–12.5 | 0.032 | | |
| 55 | 25 | 0.063–0.125 | | |
| 56 | 12.5–25 | 0.0125–0.025 | 25–50 | 0.1–0.2 |
| 57 | 25–50 | 0.0125–0.025 | 50–100 | 0.2–0.4 |
| 60 | 0.4–0.8 | 0.0063–0.1 | | |
| 61 | 1.6–3.2 | 0.05–0.1 | | |

What is claimed is:
1. A compound of the formula:

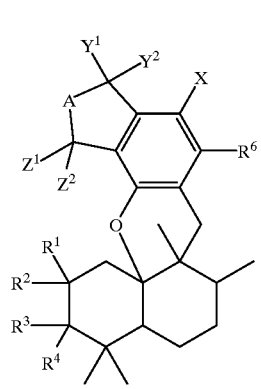

(I)

wherein
  $R^1$ is hydrogen or halogen; and $R^2$ is hydrogen, halogen, azido, an optionally substituted lower alkyl, an optionally substituted lower alkylcarbonyl, an optionally substituted arylcarbonyl, an optionally substituted heteroarylcarbonyl, —$OR^7$ (wherein $R^7$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfonyl, —$SO_3H$, an optionally substituted aryl, an optionally substituted aralkyl, an optionally substituted carbamoyl, or —$PO_3H_2$), $S(O)_nR^{13}$ (wherein $R^{13}$ is hydrogen, an optionally substituted lower alkyl, or an optionally substituted aryl, and n is 0, 1, or 2), or —$NHR^8$ (wherein $R^8$ is hydrogen, an optionally substituted lower alkyl, an optionally substituted lower alkylcarbonyl, an optionally substituted lower alkylsulfonyl, an optionally substituted arylcarbonyl, an optionally substituted aralkyloxycarbonyl, an optionally substituted arylsulfonyl, an optionally substituted heteroarylsulfonyl, or an optionally substituted carbamoyl); or $R^1$ and $R^2$ taken together may form oxo or =$NR^9$ (wherein $R^9$ is hydroxy, a lower alkoxy, an optionally substituted aralkyl, an optionally substituted arylsulfonylamino, or —$NHCONH_2$);

$R^3$ is hydrogen or halogen; and $R^4$ is hydrogen, halogen, —$OR^{10}$ (wherein $R^{10}$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfonyl, —$SO_3H$, or —$PO_3H_2$), $SR^{14}$ (wherein $R^{14}$ is hydrogen, an optionally substituted lower alkyl, or an optionally substituted aryl), or —$NHR^{11}$ (wherein $R^{11}$ is hydrogen, an optionally substituted lower alkyl, an optionally substituted lower alkylcarbonyl, an optionally substituted lower alkylsulfonyl, an optionally substituted arylsulfonyl, an optionally substituted heteroarylsulfonyl, or an optionally substituted carbamoyl); or $R^3$ and $R^4$ taken together may form oxo or =$NR^{12}$ (wherein $R^{12}$ is hydroxy, cyano, amino, an optionally substituted lower alkoxy, an optionally substituted aralkyl, an optionally substituted arylsulfonylamino, an optionally substituted aliphatic heterocyclic group, or —$NHCONH_2$); or $R^2$ and $R^4$ taken together may form an unsaturated bond or —O—;

A is =$NR^5$ (wherein $R^5$ is hydrogen, lower alkyl, lower alkylcarbonyl, or lower alkylsulfonyl; or $R^5$ and $Z^1$ taken together may form an unsaturated bond);

$R^6$ is hydrogen, cyano, nitro, amino, halogen, an optionally substituted carboxy, or an optionally substituted carbamoyl;

X is hydrogen, cyano, nitro, amino, halogen, hydroxy, lower alkoxy, an optionally substituted carboxy, an optionally substituted carbamoyl;

$Y^1$ and $Y^2$ are both hydrogens, or taken together may form oxo;

$Z^1$ and $Z^2$ are both hydrogens, or taken together may form oxo, or $Z^1$ is hydrogen and $Z^2$ is hydroxy, an optionally substituted lower alkyl, or an optionally substituted lower alkoxy, or an optionally substituted aryl), the pharmaceutically acceptable salt, or the hydrate thereof.

2. The compound of claim 1, wherein A is =NH; $Z^1$ and $Z^2$ are both hydrogens; $Y^1$ and $Y^2$ taken together form oxo.

3. The compound of claim 1, wherein $R^1$ is hydrogen; $R^2$ is hydrogen, halogen, amino, azido, or —$OR^7$ ($R^7$ is referred to as the same above); $R^3$ is hydrogen, $R^4$ is —OH.

4. The compound of claim 1, wherein $R^1$ is hydrogen; $R^2$ is hydrogen, halogen, amino, azido, or —$OR^7$ ($R^7$ is referred to as the same above); $R^3$ and $R^4$ is taken together form oxo.

5. The compound of claim 1, wherein $R^1$ and $R^3$ are both hydrogens; $R^2$ and $R^4$ are both hydrogens or halogens or $R^2$ and $R^4$ taken together form an unsaturated bond or —O—.

6. The compound of claim 1, wherein X is hydrogen, halogen, cyano, or methoxy.

7. The compound of claim 1, wherein $R^6$ is hydrogen or cyano.

8. The compound of claim 1, wherein A is =NH; $Y^1$ and $Y^2$ taken together form oxo; $R^1$, $R^3$, $R^6$, X, $Z^1$ and $Z^2$ are each hydrogens; $R^2$ and $R^4$ taken together form an unsaturated bond.

9. The compound of claim 1, wherein A is =NH; $Y^1$ and $Y^2$ taken together form oxo; $R^1$, $R^2$, $R^3$, $R^4$, $R^6$, X, $Z^1$ and $Z^2$ are each hydrogens.

10. A pharmaceutical composition containing the compound of claim 1.

* * * * *